US012265086B2

(12) United States Patent
Chen et al.

(10) Patent No.: US 12,265,086 B2
(45) Date of Patent: Apr. 1, 2025

(54) BIOMARKER OF GINGIVITIS DIAGNOSIS AND TREATMENT

(71) Applicant: Colgate-Palmolive Company, New York, NY (US)

(72) Inventors: Dandan Chen, Bridgewater, NJ (US); Harsh Mahendra Trivedi, Hillsborough, NJ (US); James Masters, Ringoes, NJ (US); Richard P. Darveau, Camano Island, WA (US); Jeffrey S. Mclean, Seattle, WA (US)

(73) Assignee: Colgate-Palmolive Company, New York, NY (US)

( * ) Notice: Subject to any disclaimer, the term of this patent is extended or adjusted under 35 U.S.C. 154(b) by 0 days.

(21) Appl. No.: 17/668,456

(22) Filed: Feb. 10, 2022

(65) Prior Publication Data

US 2023/0076737 A1  Mar. 9, 2023

Related U.S. Application Data

(60) Provisional application No. 63/200,022, filed on Feb. 10, 2021.

(51) Int. Cl.
*G01N 33/68* (2006.01)

(52) U.S. Cl.
CPC ... *G01N 33/6863* (2013.01); *G01N 2333/525* (2013.01); *G01N 2333/5412* (2013.01); *G01N 2333/5421* (2013.01); *G01N 2333/545* (2013.01); *G01N 2800/18* (2013.01)

(58) Field of Classification Search
None
See application file for complete search history.

(56) References Cited

FOREIGN PATENT DOCUMENTS

| CA | 2957934 | 8/2018 |
|----|---------|--------|
| WO | 1997/016159 | 5/1997 |
| WO | 2019/069312 | 4/2019 |
| WO | 2020/139620 | 7/2020 |
| WO | 2020/178148 | 9/2020 |

OTHER PUBLICATIONS

Hajishengallis George, 2014, "Immunomicrobial pathogenesis of periodontitis: keystones, pathobionts, and host response", Trends in Immunology, 35(1):3-11.
International Search Report and the Written Opinion of the International Searching Authority issued in International Application PCT/US2023/062423 mailed Jun. 29, 2023.
Kerns, 2021, "Microbially induced inflammation results", Retrieved form URL:https://www.proguest.com/docview/2592393309?pq-origsite=gscholar&fromopenview=true.
Prasad Kakarla Vv et al., 2018, "In this double The Effects of Two New Dual Zinc Plus Arginine Dentifrices in Reducing Oral Bacteria in Multiple Locations in the Mouth: 12-Hour Whole Mouth Antibacterial Protection for Whole Mouth Health", URL:https://www.colgateprofessional.com.au/content/dam/cp-sites/oral-care/professional/en-au/general/pdf/ss-dza-whole-mouth-health.pdf.
Sudhakaran S et al., 2020, "Personalized Periodontal Treatment: A New Paradigm Shift", EC Dental Science, pp. 136-141.
Bamashmous, S. 2019, Investigation of Chemokine and Microbiome Profiles in Gingival Health and Disease in Humans (Dissertation) Univ of Washington, 167 pages.
Parkinson, C.R. et al. 2020, "Gingivitis efficacy of a 0.454% w/w stannous fluoride dentifrice: a 24-week randomized controlled trial", BMC Oral Health 20:89.
Shimada, Y. et al. 2013, "Profiling biomakers in gingival crevicular fluid using multiplex bead immunoassay", Archives Oral Biology 58:724-730.
Bostanci, N. et al. 2020, "Salivary proteotypes of gingivities tolerance and resilience", J Clin Periodontol. 47:1304-1316.
Bamashmous, S. et al. 2021, "Human variation in gingival inflammation", PNAS vol. 118 No. 27.
Trombelli L, Tatakis DN, Scapoli C, Bottega S, Orlandini E, Tosi M. 2004. Modulation of clinical expression of plaque-induced gingivitis. II. Identification of "high-responder" and "low-responder" subjects. J Clin Periodontol. 31(4):239-252.
Löe et al. 1965 Experimental gingivitis in man. Journal of Periodontology 36(3):177-187.
International Search Report and the Written Opinion of the International Searching Authority issued in International Application PCT/US2022/015892 mailed May 24, 2022.

*Primary Examiner* — Elizabeth C. Kemmerer

(57) ABSTRACT

Methods of identifying an individual as being a slow gingivitis responder or a high gingivitis responder are disclosed. Some methods are based on IL-1β levels in the individual's GCF at the site of inflammation. Some methods are based on MIF and/or CCL-1 levels in the individual's GCF in healthy tissue distant from the site of inflammation. Some disclosed methods are based on temporal differences in IL-8, IL-6 and/or TNFα levels in the individual's GCF in healthy tissue distant from the site of inflammation during the development of plaque induced inflammation. Methods of treating an individual who has gingivitis and methods of preventing gingivitis are also provided. The treatment and prevention methods comprise determining if individual is a slow gingivitis responder or a high gingivitis responder and applying oral care compositions to the individual's oral cavity.

8 Claims, 48 Drawing Sheets
Specification includes a Sequence Listing.

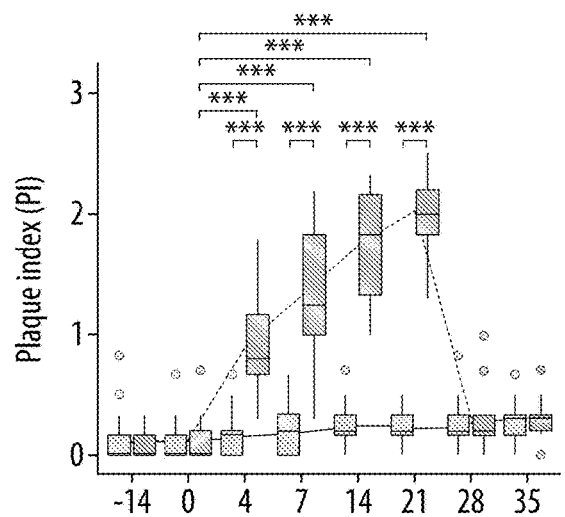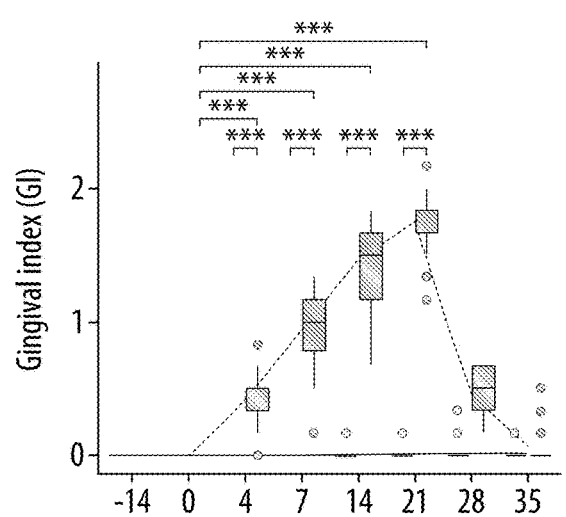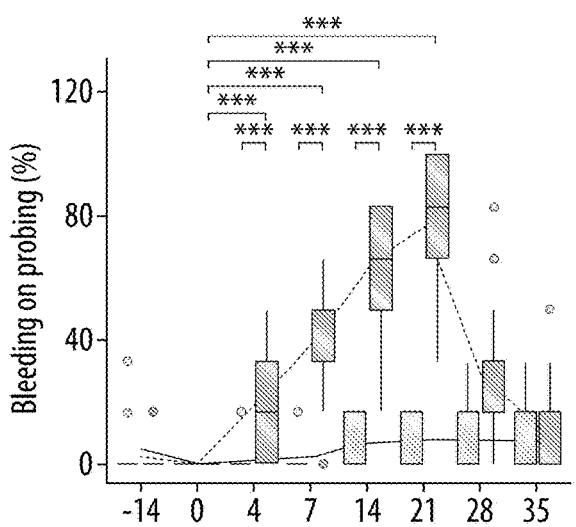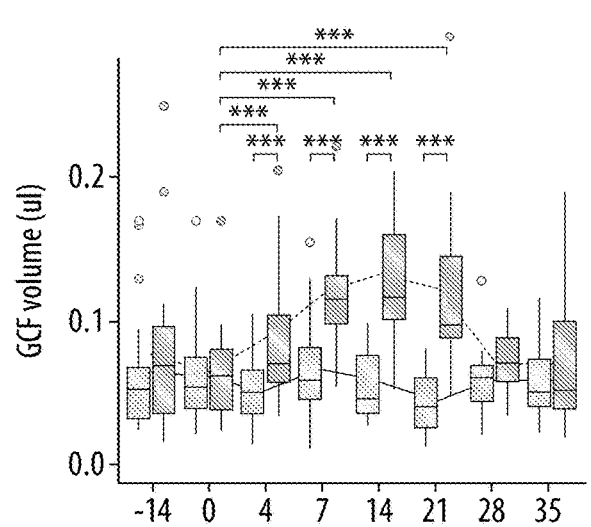

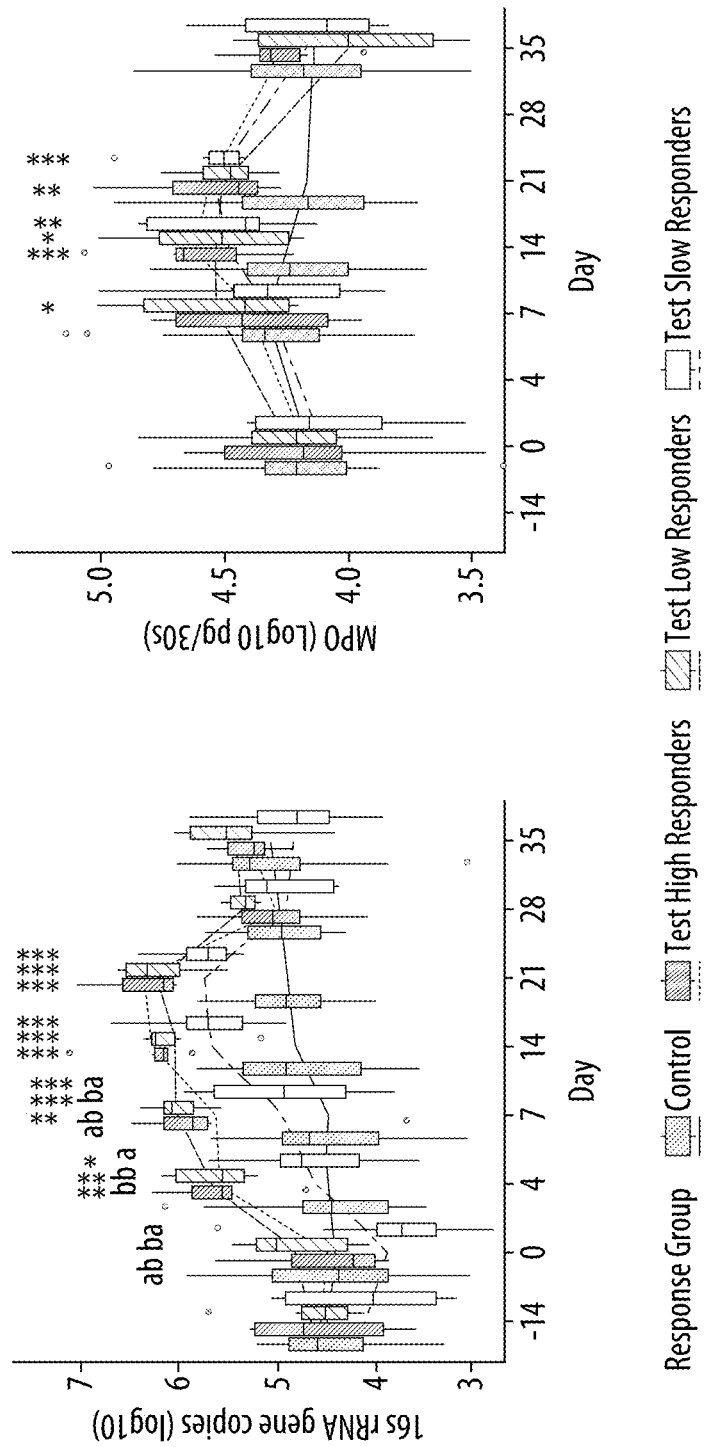

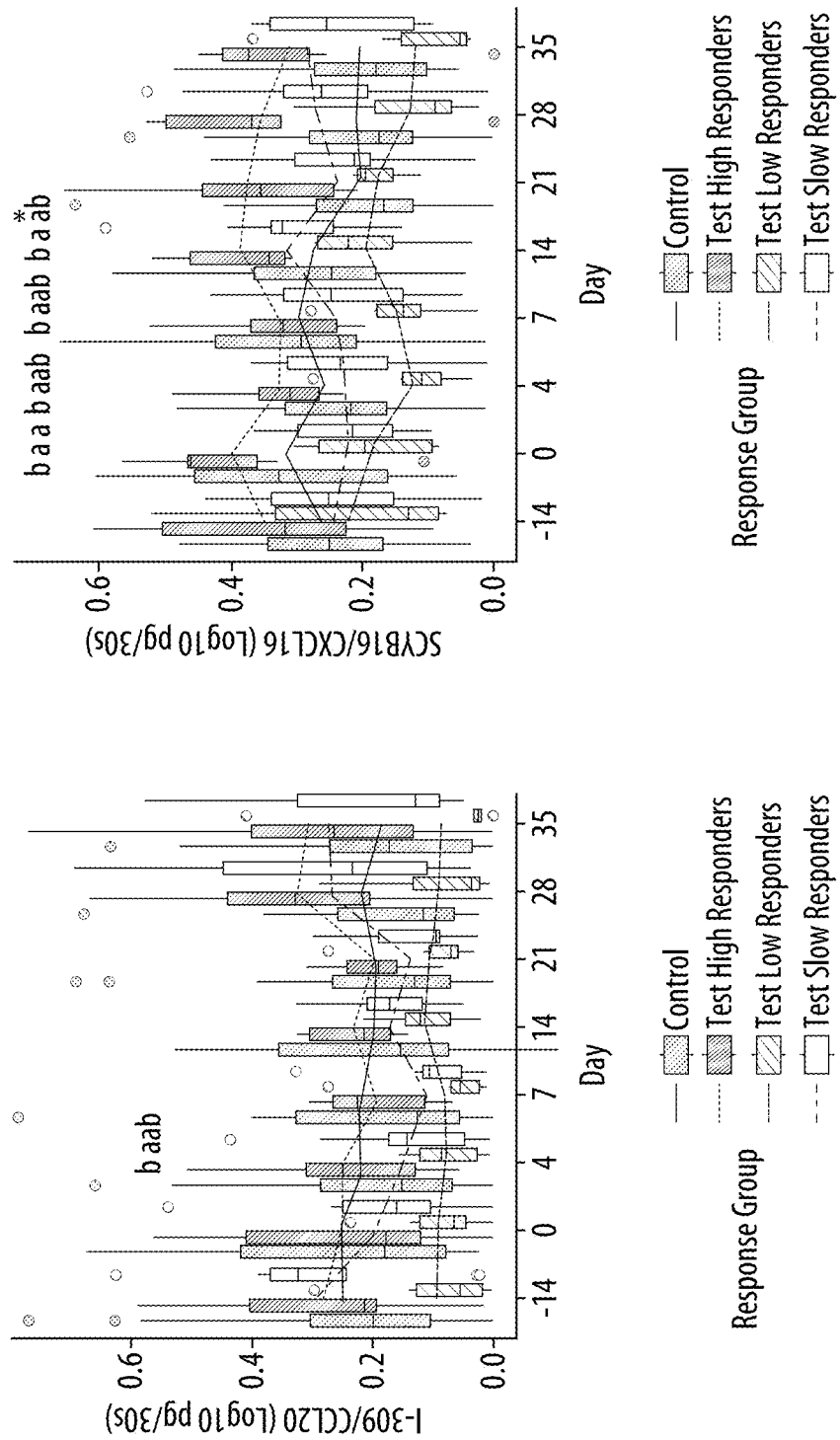

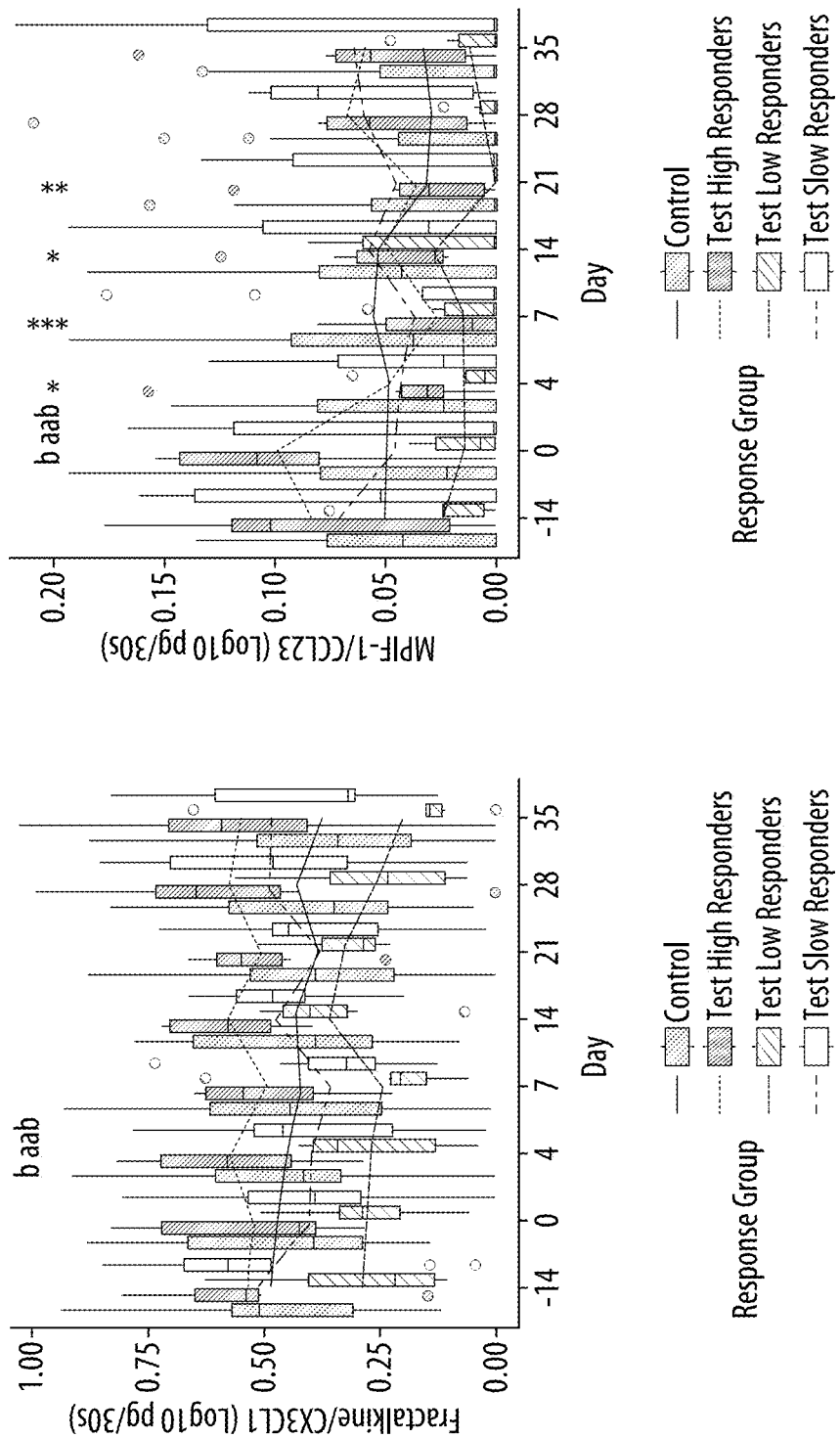

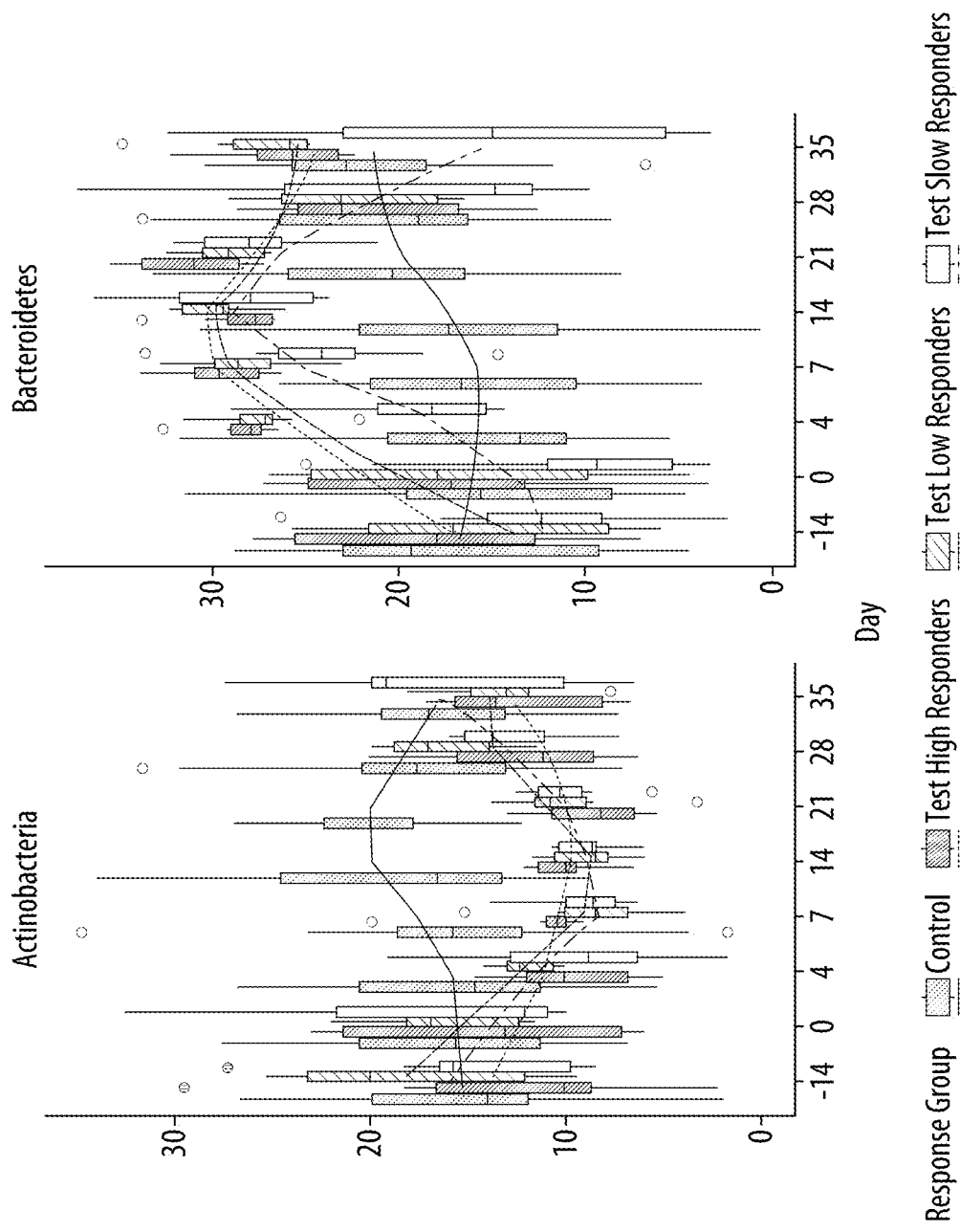

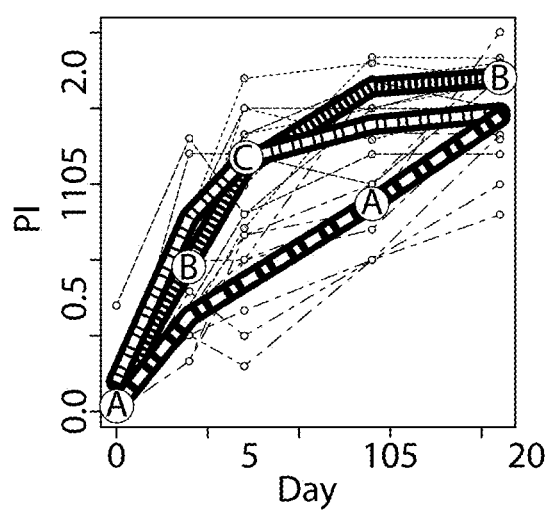
FIG. 6B
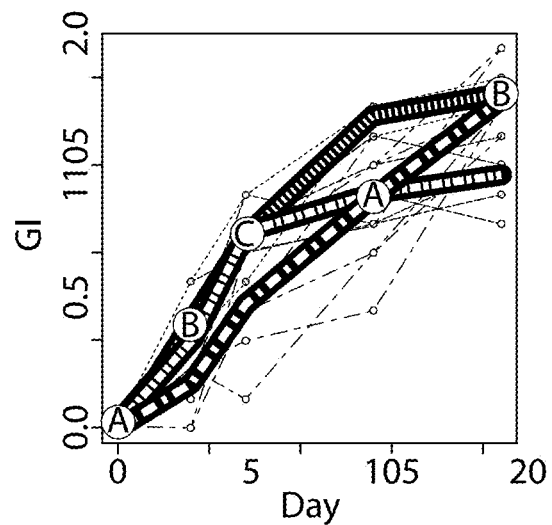
FIG. 6C
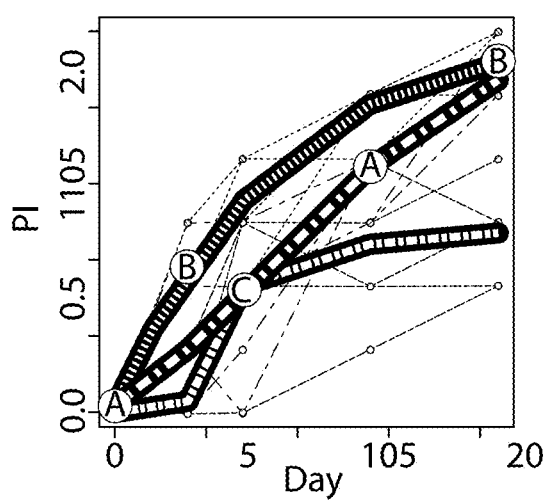
FIG. 6D
FIG. 6F
| Slow Responders | High Responders | Low Responders |
|---|---|---|
| ---Ⓐ--- | ---Ⓑ--- | ---Ⓒ--- |
| 42.9% | 28.6% | 28.6% |

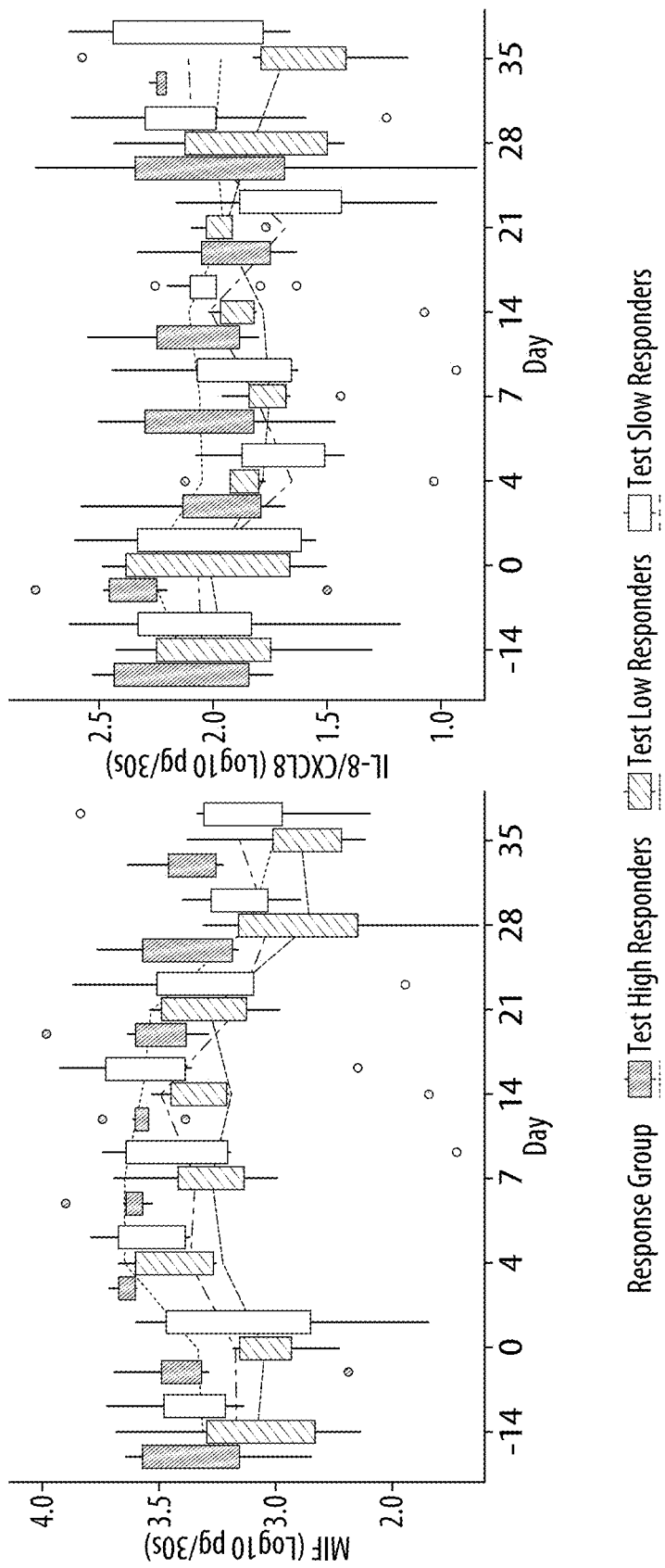

SEQUENCE LISTING

```
<160> NUMBER OF SEQ ID NOS: 5

<210> SEQ ID NO 1
<211> LENGTH: 50
<212> TYPE: DNA
<213> ORGANISM: Artificial Sequence
<220> FEATURE:
<223> OTHER INFORMATION: Synthetic sequence
```

```
<220> FEATURE:
<221> NAME/KEY: misc_feature
<222> LOCATION: (42)..(42)
<223> OTHER INFORMATION: n is a, c, g, or t

<400> SEQUENCE: 1
tcgtcggcag cgtcagatgt gtataagaga cagcctacgg gnggcwgcag            50

<210> SEQ ID NO 2
<211> LENGTH: 54
<212> TYPE: DNA
<213> ORGANISM: Artificial Sequence
<220> FEATURE:
<223> OTHER INFORMATION: Syntheric sequence

<400> SEQUENCE: 2
tctcgtgggc tcggagatgt gtataagaga caggactach vgggtatcta atcc       54

<210> SEQ ID NO 3
<211> LENGTH: 19
<212> TYPE: DNA
<213> ORGANISM: Artificial Sequence
<220> FEATURE:
<223> OTHER INFORMATION: Synthetic Sequence

<400> SEQUENCE: 3
tcctacggga ggcagcagt                                              19

<210> SEQ ID NO 4
<211> LENGTH: 26
<212> TYPE: DNA
<213> ORGANISM: Artificial Sequence
<220> FEATURE:
<223> OTHER INFORMATION: Synthetic sequence

<400> SEQUENCE: 4
ggactaccag ggtatctaat cctgtt                                      26

<210> SEQ ID NO 5
<211> LENGTH: 23
<212> TYPE: DNA
<213> ORGANISM: Artificial Sequence
<220> FEATURE:
<223> OTHER INFORMATION: Synthetic sequence

<400> SEQUENCE: 5
cgtattaccg cggctgctgg cac                                         23
```

BIOMARKER OF GINGIVITIS DIAGNOSIS AND TREATMENT

BACKGROUND

The gums, also referred to as gingiva, which are part of the soft tissue lining of the mouth, surround the teeth and provide a seal around them. The gingival margin is the interface between the sulcular epithelium and the epithelium of the oral cavity. This interface exists at the most coronal point of the gingiva, otherwise known as the crest of the marginal gingiva. The gingival crevice, also called gingival sulcus, is the space located around a tooth between the wall of the unattached gum tissue and the enamel and/or cementum of the tooth.

Healthy gums are firm and pale pink and fitted tightly around the teeth. Classic signs and symptoms of gingivitis include red, swollen, tender gums that may bleed when brushing or flossing.

Gingivitis is an inflammation of the gums that is the initial stage of gum disease. The direct cause of gingivitis is the unwanted microbial colonization by pathogenic bacteria on the teeth and gums. Pathogenic bacteria can for example produce toxins that can irritate the gum tissue, causing gingivitis. At this early stage in gum disease, damage can be reversed, since the bone and connective tissue that hold the teeth in place are not yet affected. Left untreated, however, gingivitis can become an advanced stage of gum disease, periodontitis, and cause permanent damage to teeth and jaw.

Periodontitis, a chronic and irreversible form of periodontal disease, is an age associated gingival inflammatory disease that is more prevalent than cardiovascular disease and affects more than 795 million adults globally. Periodontitis is associated with a dysbiotic dental plaque enriched in gram-negative bacteria like *Porphyromonas* and *Tannerella* species. If left untreated, periodontitis results in a dysregulated and chronic host immune response leading to irreversible structural tissue damage and bone loss. Periodontal disease has even been associated with other systemic diseases in humans, including arthritis, endocarditis, bacterial pneumonia, type-2 diabetes, and Alzheimer's. Gingivitis, a reversible and milder form of periodontal disease, is considered a precursor in the development for the majority of periodontitis cases. However, a direct connection between the etiopathogenesis leading from gingivitis to periodontitis remains unresolved. Additionally, gingivitis and periodontitis generally occur within localized tooth sites, though susceptible individuals may develop multiple diseased sites over different time periods and across their lifespan.

Gingivitis is can be treated and resolved with good oral hygiene, such as longer and more frequent brushing, flossing and the use of an antiseptic mouthwash. The earlier gingivitis is treated the less chance of permanent damage. Accordingly, methods of diagnosing gingivitis during early stages of gingivitis allow for treatment to be initiated before the condition advances. Such methods can also be adapted to monitoring oral health and treatment over time. Likewise, understanding the defenses and physical reaction, such as the nature and progression of immune responses, of an individual through the process from initial development of plaque to gingivitis and periodontal disease, as well as the status, effects and changes to oral commensal bacteria population allows for development and implementation of more effective preventative care and treatments, and products therefor.

BRIEF SUMMARY

Methods of identifying an individual as being a slow gingivitis responder or a high gingivitis responder are provided based on variations in host immune reactions and mediator levels at the site of plaque induced inflammation. The methods comprise the steps of obtaining a gingivitis-derived sample of gingival crevicular fluid from the individual who has been identified as having gingivitis and quantifying the level of IL-1β present in the gingivitis-derived sample to establish a gingivitis patient IL-1β level. The gingivitis patient IL-1β level is compared to the individual's pre-gingivitis IL-1β level that was established by obtaining a non-gingivitis-derived sample of gingival crevicular fluid from the individual prior to the development of gingivitis and quantifying IL-1β present in the non-gingivitis-derived sample. If the gingivitis patient IL-1β level is significantly unchanged compared to the pre-gingivitis IL-1β level, the individual is a slow gingivitis responder and if the gingivitis IL-1β level is significantly elevated compared to the pre-gingivitis IL-1β level, the individual is a high gingivitis responder.

In some embodiments, such methods of identifying an individual as being a slow gingivitis responder or a high gingivitis responder further comprise the steps of establishing the gingivitis patient IL-1β level by obtaining a non-gingivitis-derived sample of gingival crevicular fluid from the individual prior to the development of gingivitis and quantifying IL-1β present in the non-gingivitis-derived sample.

Methods of identifying an individual as being a slow gingivitis responder or a high gingivitis responder are provided based on variations in host immune reactions and mediator levels in heathy tissue at sites distant from the site of plaque induced inflammation. The methods comprise the steps of obtaining a distant healthy-derived sample of gingival crevicular fluid from the individual who been identified as having gingivitis and quantifying the level of MIF and/or CCL-1 present in the distant healthy-derived sample to establish a distant healthy MIF level and/or a distant healthy CCL-1 level. The distant healthy MIF level and/or distant healthy CCL-1 level is compared to the individual's pre-gingivitis MIF level and/or pre-gingivitis CCL-1 level that was established by obtaining a non-gingivitis-derived sample of gingival crevicular fluid from the individual prior to the development of gingivitis and quantifying MIF and/or CCL-1 present in the non-gingivitis-derived sample. If the distant healthy MIF level and/or distant healthy CCL-1 level is significantly elevated compared to the pre-gingivitis MIF level and/or pre-gingivitis CCL-1, the individual is a slow gingivitis responder. If the distant healthy MIF level and/or distant healthy CCL-1 level is not significantly elevated compared to the pre-gingivitis MIF level and/or pre-gingivitis CCL-1, the individual is a high gingivitis responder.

In some embodiments, such methods of identifying an individual as being a slow gingivitis responder or a high gingivitis responder further comprise the steps of establishing the gingivitis patient MIF level and/or the gingivitis patient CCL-1 level a by obtaining a non-gingivitis-derived sample of gingival crevicular fluid from the individual prior to the development of gingivitis and quantifying MIF and/or CCL-1 present in the non-gingivitis-derived sample.

In some embodiments, methods of identifying an individual as being a slow gingivitis responder or a high gingivitis responder further comprise the steps of examining the individual and determining that the individual does not have gingivitis prior to obtaining a non-gingivitis-derived sample of gingival crevicular fluid from the individual and examining the individual and determining that the individual has gingivitis prior to obtaining a gingivitis-derived sample of gingival crevicular fluid from the individual and prior to obtaining a distant healthy-derived sample of gingival crevicular fluid from the individual.

Methods of identifying an individual as being a slow gingivitis responder or a high gingivitis responder are provided based on temporal variations in host immune reactions and mediator levels in heathy tissue at sites distant from the site of plaque induced inflammation such as methods based on temporal differences in increases of IL-8 and/or IL-6 and/or TNFα in healthy tissue distant from the site of plaque induced inflammation. Methods comprise the steps of obtaining a non-gingivitis-derived sample of gingival crevicular fluid from the individual who been identified as not having gingivitis and quantifying IL-8 and/or IL-6 and/or TNFα present in the non-gingivitis-derived sample to establish a pre-gingivitis IL-8 level and/or a pre-gingivitis IL-6 level and/or a pre-gingivitis TNFα level. An early distant healthy-derived sample of gingival crevicular fluid from the individual is obtained and IL-8 and/or IL-6 and/or TNFα present in the early distant healthy-derived sample is quantified to establish an early distant healthy IL-8 level and/or an early distant healthy IL-6 level and/or an early distant healthy TNFα level. A late distant healthy-derived sample of gingival crevicular fluid from the individual is obtained and IL-8 and/or IL-6 and/or TNFα present in the late distant healthy-derived sample is quantified to establish a late distant healthy IL-8 level and/or a late distant healthy IL-6 level and/or a late distant healthy TNFα level. The early distant healthy IL-8 level and/or early distant healthy IL-6 level and/or early distant healthy TNFα level, and the late distant healthy IL-8 level and/or a late distant healthy IL-6 level and/or a late distant healthy TNFα level are compared to the pre-gingivitis IL-8 level and/or a pre-gingivitis IL-6 level and/or a pre-gingivitis TNFα level. If the early distant healthy IL-8 level and/or early distant healthy IL-6 level and/or early distant healthy TNFα level is significantly unchanged compared to the pre-gingivitis IL-8 level and/or a pre-gingivitis IL-6 level and/or a pre-gingivitis TNFα level, and the late distant healthy IL-8 level and/or late distant healthy IL-6 level and/or late distant healthy TNFα level is significantly elevated compared to the pre-gingivitis IL-8 level and/or a pre-gingivitis IL-6 level and/or a pre-gingivitis TNFα level, the individual is a slow gingivitis responder. If the early distant healthy IL-8 level and/or early distant healthy IL-6 level and/or early distant healthy TNFα level is significantly elevated compared to the pre-gingivitis IL-8 level and/or a pre-gingivitis IL-6 level and/or a pre-gingivitis TNFα level, the individual is a high gingivitis responder.

In some embodiments, such methods of identifying an individual as being a slow gingivitis responder or a high gingivitis responder further comprise the steps of examining the individual and determining that the individual does not have gingivitis prior to obtaining a non-gingivitis-derived sample of gingival crevicular fluid from the individual and examining the individual and determining that the individual has gingivitis prior to obtaining an early distant heathy-derived sample of gingival crevicular fluid from the individual and prior to obtaining a late distant healthy-derived sample of gingival crevicular fluid from the individual.

Methods of treating an individual who has been identified as having gingivitis are provided. Such methods may eliminate, ameliorate or delay or prevent progression of symptoms and disease. The methods comprise identifying the individual as being a slow gingivitis responder or a high gingivitis responder. If the individual is identified as a slow gingivitis responder, one or more oral care compositions comprising one or more ingredients having antimicrobial activity and free of additional ingredients that have anti-inflammatory activity are applied to the individual's oral cavity. If the individual is identified as a high gingivitis responder, one or more oral care compositions comprising one or more ingredients having antimicrobial activity and one or more ingredients having anti-inflammatory activity are applied to the individual's oral cavity.

Methods of preventing gingivitis and periodontal disease in an individual who has been identified as not having gingivitis are provided. Such methods may prevent, reduce the severity of or delay onset of symptoms and disease. The methods comprise identifying the individual as being a slow gingivitis responder or a high gingivitis responder. If the individual is identified as a slow gingivitis responder, one or more oral care compositions comprising one or more ingredients having antimicrobial activity and free of additional ingredients that have anti-inflammatory activity are applied to the individual's oral cavity. If the individual is identified as a high gingivitis responder, one or more oral care compositions comprising one or more ingredients having antimicrobial activity and one or more ingredients having anti-inflammatory activity are applied to the individual's oral cavity In some embodiments of the methods of treating and preventing gingivitis, the one or more ingredients having antimicrobial activity that are used in such methods of is/are selected from the group consisting of: arginine, zinc phosphate, zinc oxide, zinc citrate, triclosan, digluconate, thymol, menthol, eucalyptol, methyl salicylate, saline, antibiotics and fluoride.

In some embodiments of the methods of treating and preventing gingivitis, the one or more ingredients having anti-inflammatory activity that are used in such methods is/are selected from the group consisting of: chlorhexidine, DHA and vitamin D.

In some embodiments of the methods of treating and preventing gingivitis, the one or more oral care compositions used in such methods is/are selected from the group consisting of: a tooth paste, an oral rinse and a mouthwash.

BRIEF DESCRIPTION OF THE DRAWINGS

As shown in FIG. 1A, experimental cessation of oral hygiene leads to increased plaque biomass and induced gingivitis. Within-subject contralateral teeth with regular oral hygiene served as controls. Baseline was established from Day −14 to Day 0. Induction of experimental gingival inflammation was carried out from Day 0 through Day 21. Resolution of experimental gingivitis was observed from Day 21 until Day 35 when no residual clinical inflammatory activity was detectable. Comprehensive clinical, chemokine and microbiome analysis were conducted to obtain highly granular multiplexed analyses of changes during induction and resolution of inflammation. FIG. 1B is an illustration showing the percentages of subjects that were clustered into the three clinical response groups (high, low and slow) based on longitudinal trajectories of clinical parameters (GI, PI, BOP).

FIGS. 2A-2L show differential clinical inflammatory responses and chemokine levels in the three response groups versus controls. FIGS. 2A-2D show distributions of clinical parameters comparing test side (no-brushing) versus control side (brushed) for all subjects over time. FIGS. 2E-2H show temporal changes in inflammatory-associated clinical measures stratified by response group (high (n=6), low (n=6), slow (n=9)). Responder types in FIGS. 2E-2G may be defines as follows: High Responder—GI >1.5 at Day 21 (peak inflammation); Low Responder—GI<1.5 at Day 21, 0 based of GI at Day 21; Slow Responder had GI >1.5 at Day 21, but presented in a "delayed" response. In FIG. 2G, the Low Responder peak, which is observed at Day 14 is comparable to the Day 14 level observed for the Slow Responder but both High Responder and Slow Responder are shown to peak at Day 21. In previous studies, in which Slow Responders were unrecognized as a different responder type, Slow Responders were likely grouped in with High Responders. FIGS. 2I-2L show responses among sample-sites in each of three clinical inflammatory response groups (high, low and slow) before, during and after resolution of bacterial-induced inflammation. FIG. 2I shows bacterial load based on total 16S rRNA gene copies. Y-axis Log 10 scaled. FIG. 2J shows neutrophil marker myeloperoxidase (MPO). FIGS. 2K and 2L show pro-inflammatory cytokine IL-1β. Boxes represent data and medians±interquartile ranges; whiskers and outliers >1.5 IQR. Trend lines represent mean values across time points. Different letters above bars indicate the significant differences between groups at that time point (a, b, c) (FDR P<0.05). Differences of each group compared to baseline (Day 0) are shown above the groups and their significance level indicated by asterisks. Significance levels: *$P<0.05$, $P\le0.001$, and *$P\le5\times10-5$. (717 L) Comparison of IL-1β levels between groups at peak clinical inflammatory endpoint (21 days) show the subjects in the slow group were significantly different than the high responder group that displayed elevated IL-1β.

FIG. 3A shows normalized (row-wise Z-score) mean values for chemokine expression by responder groups and controls (all responder groups and control are combined) by day. The low responder group displays several standard deviations below the mean of all the groups in most chemokines. FIG. 3B shows temporal relationships between major neutrophil chemokines IL-8 and MIF (macrophage inhibitory factor) with myeloperoxidase (MPO, a neutrophil marker) and bacterial load. MIF demonstrated an inverted U-shape distribution during the induction-resolution human experiment that was similar to the temporal changes in microbial load (negative quadratic coefficients; p-val<0.01 for both MIF and Bacterial load). MPO changes followed the same temporal pattern as MIF (negative quadratic coefficient; p-val<0.001), while IL-8 levels demonstrated a U-shape distribution with no association to MPO levels (positive quadratic coefficient; p-val=0.09). That is, increases in MIF and MPO follow a similar pattern to each other and a similar pattern is observed when bacterial load is plotted with MIF. In contrast, IL-8 goes down when MPO goes up, and when bacterial load is plotted, IL-8 goes down when bacterial load goes up. There is a direct inverse relationship between an increase in MIF and a decrease in IL-8 during experimental gingivitis. FIGS. 3C-3H contain data showing temporal changes in major neutrophil chemokines (MIF, IL-8, and CXCL6) across responder groups compared to each of the responder groups (FIG. 3C, FIG. 3E, FIG. 3G) and between their respective control side sample in the split-mouth design (FIG. D, FIG. F, FIG. H). Boxes represents data and medians ±interquartile ranges; whiskers and outliers >1.5 IQR. Trend lines represent mean values across time points. Differences of each group compared to baseline (Day 0) are shown above the groups and their significance level indicated by asterisks. Significance levels: *$P<0.05$, $P\le0.001$, and *$P\le5\times10-5$.

FIGS. 4A-4F contain data showing changes in levels of chemokines involved in bone homeostasis following induction of reversible bone-sparing gingival inflammation. Responses among sample-sites in each of three clinical inflammatory response groups before, during, and after resolution of bacterial-induced inflammation. Boxes represents data and medians ±interquartile ranges; whiskers and outliers >1.5 IQR. Trend lines represent mean values across time points. Different letters above bars indicate the significant differences between groups at that time point (a, b, c) (FDR P<0.05). Differences of each group compared to baseline (Day 0) are shown above the groups and their significance level indicated by asterisks. Significance levels: *$P<0.05$, $P<0.001$, and *$P<5\times10-5$.

FIG. 5A shows Faith's phylogenetic diversity by responder group and controls from Day −14 to Day 35 (n=334 samples from 21 subjects). Boxplots show median and 25th/75th quartiles; whiskers show inner fences. Lines show mean richness by clinical responder group (high, low, and slow) and controls (within-subject non-inflamed gingival sites). FIG. 5B shows non-metric multidimensional scaling (NMDS) plots of Beta diversity (Unweighted Unifrac distance matrices) by responder group and controls from Day −14 to Day 35 (n=334 samples from 21 subjects). Tests for significance in Beta diversity between groups determined by Permanova. FIG. 5C shows phylum level distributions of relative abundance by responder group and controls from Day −14 to Day 3 (n=334 samples from 21 subjects). A gram positive to gram negative shift seen is gingivitis is delayed in the Slow Response group. Phylum level Firmicutes (gram +) is associated with commensalism or health and decrease with inflammation; Bacteroidetes (gram −) is associated with dysbiosis or disease and an increase with inflammation. FIGS. 5D and 5E show genus level mean relative abundance by responder group and controls from Day −14 to Day 35. Linear regression (Loess) shown with 95% confidence bound (n=334 samples from 21 subjects). FIG. 5F shows *Streptococcus* mean relative abundance by responder group and controls from Day −14 to Day 35 (n=334 samples from 21 subjects). Also shown are center log transformed (CLR) relative abundances of amplicon sequence variants (ASV's) taxonomically assigned to *Streptococcus sanguinis* and *Streptococcus oralis* species in high, slow and low inflammatory response groups from Day −14 and Day 35. Boxplots show median and lower/upper quartiles; whiskers show inner fences (see Methods) (n=84 from 21 subjects), (Wilcox test; adjusted by FDR; Table 4). Stars show FDR-corrected statistical significance levels (FDR *$P\le0.05$, $P\le0.01$, *$P\le0.001$, ****$P\le0.0001$).

FIGS. 6A-6E contains data showing that clustering algorithm applied to longitudinal clinical parameters resulted in three distinct responder groups. FIGS. 6A-6D contains data generated using a three-step computational algorithm to identify clusters of longitudinal trajectories based on convergent results of multiple criteria scores. FIG. 6A shows optimal number of clusters determined by the Calinski-Harabasz criterion supporting three distinct clusters of longitudinal trajectories as more computationally robust. FIGS. 6B-6D show longitudinal trajectories of PI, GI and BOP during the induction experiment for all subjects and the mean trajectory of each identified cluster. FIG. 6E shows canonical correspondence analysis of clinical measures of inflammation reveals longitudinal separation of responder groups consistent with the computed responder groups. FIG. 6F shows the percentage of each of slow responders, high responders and low responders that were identified.

FIGS. 7A-7F contain data showing temporal changes in cytokine levels across responder groups. FIG. 7A shows data for Macrophage Inhibition Factor, MIF. FIG. 7B shows data for IL-8. FIG. 7C shows data for CXCL1. FIG. 7D shows data for CXCL5. FIG. 7E shows data for CXCL2. FIG. 7F shows data for CXCL6. Boxes represents data and medians ±interquartile ranges; whiskers and outliers >1.5 IQR. Trend lines represent mean values across time points. Different letters above bars indicate the significant differences between groups at that time point (a, b, c) (FDR P<0.05). Differences of each group compared to baseline (Day 0) are shown above the groups and their significance level indicated by asterisks. Significance levels: *P<0.05, P≤0.001, and *P≤5×10−5.

FIG. 10A shows Plaque Index (PI) stratified by Inflammatory Responder Type (IRT) over the induction phase (Day 0-21) with respective Controls. FIG. 10B shows linear regression of mean PI by IRT Test and Control over the induction phase. FIG. 10C shows Gingival Index (GI) stratified by IRT over the induction phase with respective Controls. Red dashed line represents a GI value of 1.5 which represents significant clinical inflammation within gingiva tissues. FIG. 10D shows linear regression of mean GI by IRT Test and Control over the induction phase. FIG. 10E shows Bleeding on Probing (BOP) stratified by IRT over the induction phase with respective Controls. FIG. 10F shows linear regression of mean BOP by IRT Test and Control over the induction phase. FIG. 10G shows Gingival crevicular fluid (GCF) volume stratified by IRT over the induction phase with respective Controls. FIG. 10H shows linear regression of mean GCF volume by IRT Test and Control over the induction phase. FIG. 10I shows Bacterial Load (16S copies) stratified by IRT over the induction phase with respective Controls. FIG. 10J shows linear regression of mean Bacterial Load by IRT Test and Control over the induction phase. Boxes represents data and medians ±interquartile ranges; whiskers and outliers >1.5 IQR below (above) the 25th (75th) percentile. Trend lines represent loess regression mean values across all time points. Statistical analysis was performed using the non-parametric Wilcoxon-Rank Sum Test adjusted by FDR. Significance level indicated by asterisks. Significance levels: ns=non-significant, *P<0.05, P≤0.01, and *P≤0.001.

FIG. 11A shows Z-scored heatmap of host inflammatory mediators (41) clustered using the k-means algorithm for clinical Inflammatory Responder Type (IRT) test and control sites over the Induction phase (Day 0-21). Chemokines that change on the control side with statistical significance are highlighted in red. FIG. 11B shows Standard deviation from the mean chemokine value within respective clusters were plotted over the Induction phase (Day 0-21). FIG. 11C shows CCL1 in Slow-IRT showed similar patterns to changes occurring on the test side within the control side and 7 out of 9 individual subjects had the same negative trend in decreasing CCL1 concentrations over Induction (Day 0-21). FIG. 11D shows IL-1β in Low-IRT showed similar patterns to changes occurring on the test side within the control side and 4 out of 6 individual subjects had the same negative trend in decreasing IL-1β concentrations over Induction (Day 0-21). FIG. 11E shows MIF in Slow-IRT showed similar patterns to changes occurring on the test side within the control side and 7 out of 9 individual subjects had the same negative trend in decreasing MIF concentrations over Induction (Day 0-21). FIG. 11F shows TNF-a in Low-IRT showed similar patterns to changes occurring on the test side within the control side and 6 out of 6 individual subjects had the same negative trend in decreasing TNF-a concentrations over Induction (Day 0-21). Boxes represent data and medians ±interquartile ranges; whiskers and outliers >1.5 IQR below (above) the 25th (75th) percentile. Trend lines represent loess regression mean values across all time points. Trendlines for Chemokines by subject represent the linear regressed mean over the induction phase (Day 0-21). Statistical analysis was performed using the non-parametric Wilcoxon-Rank Sum Test adjusted by FDR. Significance level indicated by asterisks. Significance levels: ns=non-significant, *P<0.05, P≤0.01, and *P≤0.001.

FIGS. 12A-12C show Z-scored heatmap of log fold change of chemokines compared to baseline (Day 0) among different clinical Inflammatory Responder Type (IRT) control sites. Key inflammatory mediators are highlighted in red text (lighter). FIGS. 12D-12F show IL-8 (Left y-axis), IL-6, and TNF-a (Right y-axis) among IRT control sites. Red box (shaded) highlights shift in host mediators in control site.

DETAILED DESCRIPTION

Figure 1A:
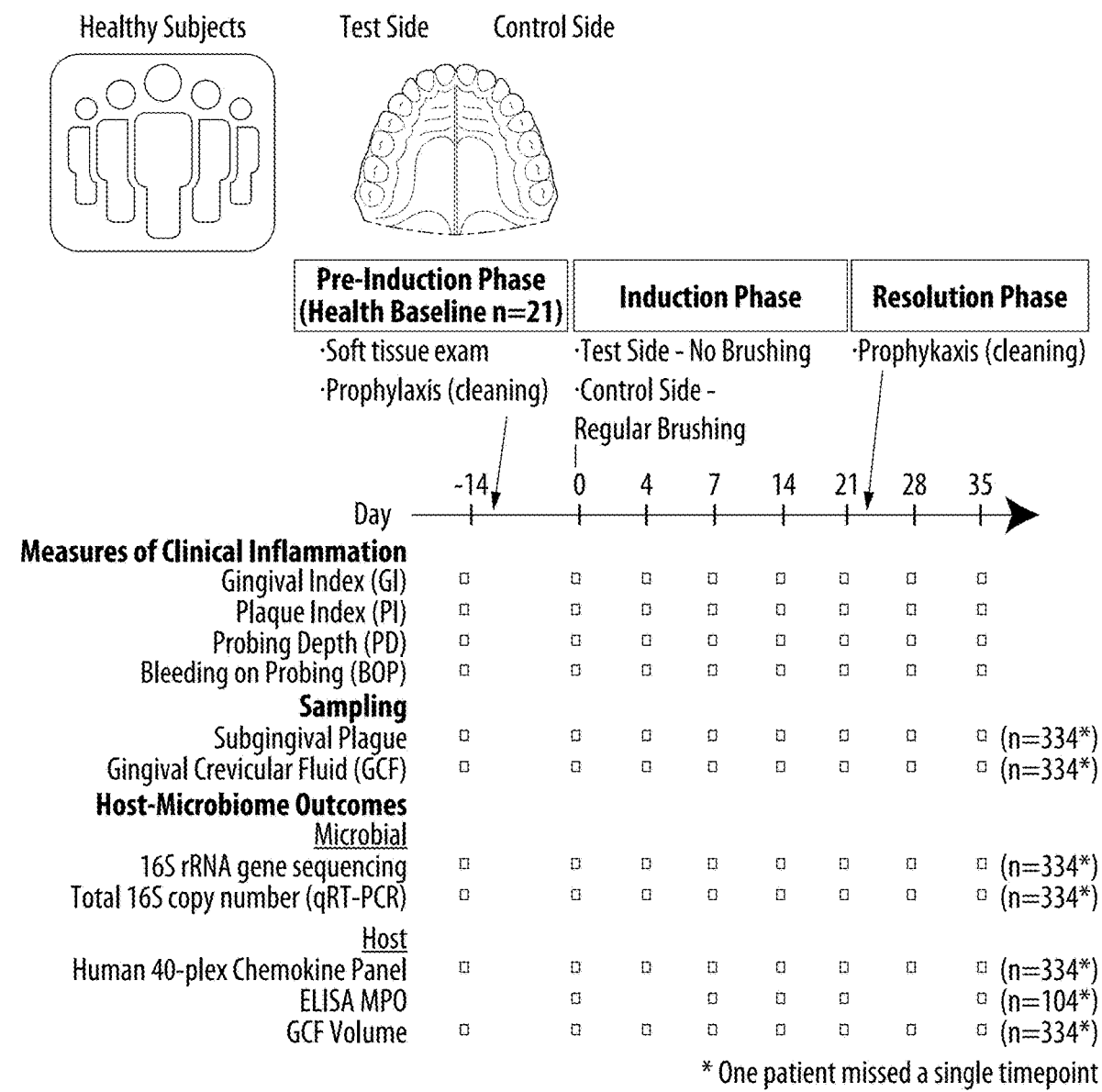
FIGS. 1A and 1B set out an overview of the experimental gingivitis study design and results of the study. Custom fitted molds were incorporated to shield test side experimental teeth from brushing.

The terms "slow gingivitis responder", "slow responder" and "Slow-IRT" are used interchangeably.

The terms "high gingivitis responder", "high responder" and "High-IRT" are used interchangeably.

The terms "low gingivitis responder", "low responder" and "Low-IRT" are used interchangeably.

A "non-gingivitis-derived sample of gingival crevicular fluid" is a GCF sample obtained from the individual when the individual has been identified as not having gingivitis. The terms "non-gingivitis-derived sample of gingival crevicular fluid", "non-gingivitis-derived GCF sample", "pre-gingivitis-derived sample of gingival crevicular fluid" and "pre-gingivitis-derived GCF sample" are used interchangeably and refer to a GCF sample obtained from the individual when the individual has been identified as not having gingivitis.

A "gingivitis-derived sample of gingival crevicular fluid" (GFC) is a GCF sample obtained at the site of inflammation from an individual when the individual has been identified as having gingivitis. The terms "gingivitis-derived sample of gingival crevicular fluid" (GFC) and "gingivitis-derived GCF sample" are used interchangeably and refer to a GCF sample obtained at the site of gingivitis, i.e., the site of localized plaque-induced inflammation from an individual that has been identified as having gingivitis.

A "distant healthy-derived sample of gingival crevicular fluid" (GFC) is a GCF sample obtained from a site of healthy tissue that is distant from the site of gingivitis, i.e., the site of localized plaque-induced inflammation, in an individual that has localized plaque-induced inflammation. The terms "distant healthy-derived sample of gingival crevicular fluid" and "distant healthy-derived sample GCF sample" are used interchangeably and refer to a GCF sample obtained at the site of healthy tissue that is distant from the site of gingivitis, i.e., the site of localized plaque-induced inflammation, from an individual that has been identified as having gingivitis. A "contralateral sample of gingival crevicular fluid" is an example of a distant healthy-derived sample of gingival crevicular fluid.

An "early distant healthy-derived sample of gingival crevicular fluid" (GFC) is a GCF sample obtained 7-14 days after the appearance of localized plaque-induced inflammation from a site of healthy tissue that is distant from the site of gingivitis, i.e., the site of localized plaque-induced inflammation, in an individual that has localized plaque-induced inflammation or if an induction procedure based on the experimental gingivitis model is employed (which includes a 14-day pre-induction period that begins with a cleaning and examination a day followed by a 21-day induction period during which time there is a cessation of brushing) a GCF sample obtained 21-28 days after the start of the pre-induction phase, which is 7-14 days after the start of the induction phase).

An "late distant healthy-derived sample of gingival crevicular fluid" (GFC) is a GCF sample obtained after 14 days after the appearance of localized plaque-induced inflammation from a site of healthy tissue that is distant from the site of gingivitis, i.e., the site of localized plaque-induced inflammation, in an individual that has localized plaque-induced inflammation or if an induction procedure based on the experimental gingivitis model is employed (which includes a 14-day pre-induction period that begins with a cleaning and examination a day followed by a 21-day induction period during which time there is a cessation of brushing) a GCF sample obtained after 28 days after the start of the pre-induction phase, which is after 14 days after the start of the induction phase).

The terms "pre-gingivitis level", "non-gingivitis level" and "baseline level" are used interchangeably and refer to a level of a measurable feature in gingival crevicular fluid in a pre-gingivitis-derived GCF sample gingivitis-derived sample of GCF sample.

The terms "gingivitis patient level" and "localized gingivitis level" are used interchangeably and refer to a level of a measurable feature in gingival crevicular fluid in a gingivitis-derived sample of GCF sample. For example, a gingivitis IL-1β level refers to the level of IL-1β in a gingivitis-derived sample. of GCF sample is the obtained at the site of gingivitis, i.e., the site of localized plaque-induced inflammation from an individual that has been identified as having gingivitis.

The terms "distant healthy-derived sample level" are used interchangeably and refer to a level of a measurable feature in gingival crevicular fluid in a distant healthy-derived GCF sample.

A "pre-gingivitis IL-1β level" is the amount of IL-1β quantified in a non-gingivitis-derived sample of GCF. The terms "pre-gingivitis level of IL-1β," "pre-gingivitis IL-1β level," "baseline level of IL-1β," "baseline IL-1β level," "non-gingivitis level of IL-1β," and "non-gingivitis IL-1β level" are used interchangeably.

A "pre-gingivitis MIF level" is the amount of MIF quantified in a non-gingivitis-derived sample of GCF. The terms "pre-gingivitis level of MIF," "pre-gingivitis MIF level," "baseline level of MIF," "baseline MIF level," "non-gingivitis level of MIF," and "non-gingivitis MIF level" are used interchangeably.

A "pre-gingivitis CCL-1 level" is the amount of CCL-1 quantified in a non-gingivitis-derived sample of GCF. The terms "pre-gingivitis level of CCL-1," "pre-gingivitis CCL-1 level," "baseline level of CCL-1," "baseline CCL-1 level," "non-gingivitis level of CCL-1," and "non-gingivitis CCL-1 level" are used interchangeably.

A "pre-gingivitis IL-8 level" is the amount of IL-8 quantified in a non-gingivitis-derived sample of GCF. The terms "pre-gingivitis level of IL-8," "pre-gingivitis IL-8 level," "baseline level of IL-8," "baseline IL-8 level," "non-gingivitis level of IL-8," and "non-gingivitis IL-8 level" are used interchangeably.

A "pre-gingivitis IL-6 level" is the amount of IL-6 quantified in a non-gingivitis-derived sample of GCF. The terms "pre-gingivitis level of IL-6," "pre-gingivitis IL-6 level," "baseline level of IL-6," "baseline IL-6 level," "non-gingivitis level of IL-6," and "non-gingivitis IL-6 level" are used interchangeably.

A "pre-gingivitis TNFα level" is the amount of TNFα quantified in a non-gingivitis-derived sample of GCF. The terms "pre-gingivitis level of TNFα," "pre-gingivitis TNFα level," "baseline level of TNFα," "baseline TNFα level," "non-gingivitis level of TNFα," and "non-gingivitis TNFα level" are used interchangeably.

A "gingivitis patient IL-1β level" is the amount of IL-1β quantified in a gingivitis-derived sample of GCF.

An "distant healthy MIF level" is the amount of MIF quantified in a distant healthy-derived sample of GCF.

An "distant healthy CCL-1 level" is the amount of CCL-1 quantified in a distant healthy-derived sample of GCF.

An "early distant healthy IL-8 level" is the amount of IL-8 quantified in an early distant healthy-derived sample of GCF.

An "early distant healthy IL-6 level" is the amount of IL-6 quantified in an early distant healthy-derived sample of GCF.

An "early distant healthy TNFα level" is the amount of TNFα quantified in an early distant healthy-derived sample of GCF.

A "late distant healthy IL-8 level" is the amount of IL-8 quantified in a late distant healthy-derived sample of GCF.

A "late distant healthy IL-6 level" is the amount of IL-6 quantified in a late distant healthy-derived sample of GCF.

A "late distant healthy TNFα level" is the amount of TNFα quantified in a late distant healthy-derived sample of GCF.

"Statistically elevated" and "significantly elevated" are used interchangeably and refer to one amount being higher than another and the difference being statistically significant.

"Unchanged" and "significantly unchanged" are used interchangeably and refer to one amount being the same or nearly the same as another and the difference not being statistically significant.

"Oral care composition" refers to a composition that is delivered to the oral surfaces. The composition may be a product which, during the normal course of usage, is not, the purpose of systemic administration of particular therapeutic agents, intentionally swallowed, but is rather retained in the oral cavity for a time sufficient to contact substantially all of the dental surfaces and/or oral tissues for the purposes of oral activity. Examples of such compositions include, but are not limited to, toothpaste or a dentifrice, a mouthwash or a mouth rinse, a topical oral gel, a denture cleanser, and the like.

The stability in host-microbial interface is essential for health across mucosal surfaces in the human body. Barrier immunity is not characterized by the absence of bacteria but by their regulated presence under healthy immune surveillance. This has also been termed the para-inflammatory state and is required for tissues to respond to insult and restore homeostasis. This is especially relevant on mucosal surfaces where there is a constant microbial challenge to the host immune system. For example, in oral mucosal surfaces, one of the main protective mechanisms of tissue and therefore, host protection from unwanted microbial colonization is the constant highly orchestrated transit of neutrophils from the local periodontal vasculature through healthy gingival tissue and into the gingival crevice. There, neutrophil surveillance is essential for maintaining the proper amount and composition of dental plaque, a highly evolved and organized bacterial consortium found on the tooth surface that actively contributes to normal periodontal tissue function.

Oral commensal bacteria actively participate with gingival tissue to maintain healthy neutrophil surveillance and normal tissue and bone turnover processes. Disruption of this homeostatic bacterial—host relationship occurs during experimental gingivitis studies where it has been clearly established that increases in the number and type of oral commensal bacteria increase clinical indices of inflammation. Studies in germ-free mice have revealed that dental plaque is essential for proper neutrophil homing and also contributes to normal alveolar bone turnover processes. Proper neutrophil monitoring of the dental plaque microbial biofilm therefore results in a process termed "healthy homeostasis" with the consequence being both colonization resistance, a microbial protection mechanism which resists infection as well as maintaining the appropriate microbial composition for normal periodontal bone and tissue function.

Model systems for studying host-microbe interaction dynamics during inflammatory events directly in humans in a well-controlled and reversible way are limited. A unique advantage of studies in the oral cavity is the availability of one such model, experimental gingivitis (EG). Deliberate cessation of oral hygiene allows for the high-resolution study of the initiation and development of gingival inflammation, as well as understanding the variation in the severity which exists across the human population. This model permits the development and maturation of normal dental plaque, a rich biofilm, along the gingival margin and within the periodontal pocket surrounding human teeth which results in a relatively rapid host response as inflammation progresses to a clinically diseased state. Furthermore, this model also allows for the investigation of the effects of localized inflammation in distant otherwise healthy tissues in the human oral cavity.

Accumulation of dental plaque in the human induced gingivitis experimental model is a convenient and reproducible model facilitating the study of the disruption of healthy tissue homeostasis. The human experimental gingivitis model offers the unique advantage of monitoring disease development in real time in order to study the change from a model have revealed rapid alterations in clinical measures of inflammation that parallel microbial plaque biomass increases and compositional changes during the development of gingivitis. Furthermore, it has been reported that in human experimental gingivitis studies the subject-based susceptibility to plaque-induced gingival inflammation is an individual trait. It has been reported that individual responses to induced gingivitis could be grouped into high and low clinical phenotypes with the high response phenotype being linked to a persistent hyper-responsive para-inflammatory state. Although nearly every human gingivitis study since 1965 has recognized there is variation in clinical parameters to bacterial dental plaque accumulation, the factors responsible for the significantly different individual host responses have not been elucidated. In this report, three different clinical response groups were identified and a granular parallel analysis of these groups revealed unique host and microbiome characteristics during induced inflammation.

As disclosed herein, experimental gingivitis studies where dental hygiene was withheld from select teeth allowed natural bacterial accumulation and provided a unique opportunity to study the reversible transition from health to inflammatory disease in humans. Longitudinal analysis of both the microbial and host changes during human experimental gingivitis, revealed a previously unknown variation in the human host response and microbial succession sequence during inflammation. The experimental gingivitis produced three unique clinical inflammatory phenotypes (high, low, and slow) and revealed that IL-1β, which has been previously recognized as a major gingivitis associated inflammatory mediator, was not associated with clinical gingival inflammation in individuals in the slow response group. Furthermore, plaque accumulation resulted in the downregulation of both neutrophil and bone activation responses in all response groups revealing a novel tissue and bone protective response during gingival inflammation. The low clinical response group was characterized by overall low concentrations of host mediators and significantly lower levels of bone and tissue remodeling mediators despite similar bacterial accumulation and compositional characteristics as the high clinical response group. Significantly higher levels of *Streptococcus* spp. defined the most common slow responses, which led to a clinically more resistant healthy homeostatic state. These alterations in chemokine and microbial composition responses during experimental gingivitis reveal a previously uncharacterized variation in the human host response to a disruption in gingival homeostasis due to bacterial overgrowth. Understanding this human variation in gingival inflammation may facilitate the identification of periodontitis susceptible individuals. In addition, this study underscores the variability in host response that leads to distinct alterations in the oral microbiome that may impact clinical outcomes in terms of chronic inflammation and bone remodeling. The significance of these findings characterizes for the first time three different clinical responses designated high, low, and slow, discerning unique host and microbial features which define each group.

In addition, previously unrecognized host protective mechanisms to prevent inflammatory bone resorption during reversible gingival inflammation has been observed.

Also provided herein is a method of distinguishing High-IRTs from Slow-IRTs based on the changes within healthy control teeth in an individual who have localized plaque induced inflammation. Microbially-induced inflammation was produced in test sites for a period of 21 Days in a well-controlled and reversible way within young generally healthy adults. By analyzing the GCF from samples taken from healthy tissue distant from the site of inflammation located contralaterally in the mouth, significant changes in macrophage migration inhibitory factor (MIF) and C-C motif ligand 1 (CCL1) were revealed at such healthy tissue distant from the site of inflammation in individuals in the slow response group. Methods are provided which entail analyzing sample from healthy tissue at sites distant from the site of plaque induced inflammation and treating an individual based upon the results of such analysis. Moreover, significant changes in host mediators IL-8, IL-6 and TNFα have been identified in both High-IRT and Slow-IRT individuals, albeit the timing of such changes differs between the two IRT types. That is, the host mediators present in GCF change in healthy tissue at sites distant from the site of plaque induced inflammation. Methods are provided which entail analyzing sample from healthy tissue at sites distant from the site of plaque induced inflammation at various time points in the development of plaque induced inflammation and treating an individual based upon the results of such analysis.

Methods of identifying and monitoring gingivitis have been developed to identify whether an individual who has gingivitis is a high responder or a slow responder. Methods of treating an individual who has gingivitis have been developed wherein the individual is first identified as being either a high responder or a slow responder. Such methods may eliminate, ameliorate or delay or prevent progression of symptoms and disease. Methods of preventing gingivitis have been developed wherein the individual is first identified as being either a high responder or a slow responder. Such methods may prevent, reduce the severity of or delay onset of symptoms and disease. High responders receive treatment that comprises administering compositions which include anti-inflammatory and anti-microbial components. Slow responders receive treatment that comprises administering compositions which anti-microbial components.

The observation that IL-1β was not associated with clinical gingival inflammation in individuals in the slow response group indicates treatment of slow responders with anti-inflammatory components may be undesirable and counter-productive to an effective anti-gingivitis treatment. In slow responders an anti-inflammatory treatment may suppress the para-inflammatory state of the oral mucosal tissue, interfere with the restoration of homeostasis. Anti-inflammatory components may disrupt the function and activity of neutrophils in the gingival crevice. In the case of high responders, anti-inflammatory components are useful to downregulate IL-1β and otherwise suppress gingival inflammation.

To identify whether an individual who has gingivitis is a high responder or a slow responder, an initial baseline measurement of local chemokine responsiveness is measured in gingival transudate, i.e., Gingival Crevicular Fluid (GCF). Samples from the GCF may be collected when an individual does not have gingivitis to establish baseline IL-1β levels, baseline MIF levels and CCL1 in the non-gingivitis state. Likewise, samples from the GCF may be collected when an individual does not have gingivitis to establish baseline IL-8 levels, baseline IL-6 levels and TNFα in the non-gingivitis state.

Accordingly, prior to sample collection, the individual is identified as not having gingivitis. Classic signs and symptoms of gingivitis include red, swollen, tender gums that may bleed when brushing or flossing. Prior to sample collection, the individual may be examined to detect the presence or absence of symptoms of gingivitis such as red, swollen or tender gums. Further, an individual may be questioned to determine if they have been experiencing pain or tenderness of their gums and/or if their gums bleed when brushing or flossing. Once the individual is identified as not having gingivitis, sample collection can be done in order to establish baseline (non-gingivitis) levels of IL-1β, and/or MIF and/or CCL1 and/or IL-8 and/or IL-6 and/or TNFα in the non-gingivitis state. After first identifying that the individual does not have gingivitis, collecting GCF samples from individuals who do not gingivitis and then analyzing such samples to determine IL-1β levels and/or MIF levels and/or CCL1 levels and/or IL-8 levels and/or IL-6 levels and/or TNFα levels is unconventional. Establishing a baseline IL-1β level and/or a baseline MIF level and/or a baseline CCL1 level and/or a baseline IL-8 level and/or a baseline IL-6 level and/or a baseline TNFα level for an individual may be useful in a method to determine whether, after the individual develops gingivitis, the individual can be identified as a high responder or slow responder. The steps of identifying the individual as not having gingivitis and then collecting a GCF sample for measurement of IL-1β and/or MIF and/or CCL1 and/or IL-8 and/or IL-6 and/or TNFα levels can occur when an individual is scheduled to undergo a cleaning or another procedure. In some embodiments, the steps of first identifying that the individual does not have gingivitis, collecting GCF samples from individuals who do not gingivitis and then analyzing such samples to determine IL-1β and/or MIF and/or CCL1 and/or IL-8 and/or IL-6 and/or TNFα levels can be done once or may be done multiple times in order to more establish the baseline IL-1β level and/or the baseline MIF level and/or the baseline CCL1 level and/or the baseline IL-8 level and/or the baseline IL-6 level and/or the baseline TNFα level.

When the individual develops gingivitis, samples from the GCF at the site of inflammation may be collected to determine IL-1β levels when the individual has gingivitis. After first identifying that the individual has gingivitis, GCF samples at the site of inflammation are collected from the individual who has gingivitis, such samples are analyzed to determine IL-1β levels which are then compared to baseline IL-1β level so the individual can be identified as a high responder or slow responder. Elevated IL-1β levels in an individual who has gingivitis compared to the baseline IL-1β levels indicated that the individual is a high responder. An individual who has gingivitis is identified as a slow responder when IL-1β levels when the individual who has gingivitis are not significantly elevated from baseline IL-1β levels. In some embodiments, plaque samples may be collected when GCF is collected and the various bacteria in the plaque samples may be identified.

When the individual develops gingivitis, samples from the GCF at healthy tissue sites distant for the site of inflammation may be collected to determine MIF and/or CCL1 and/or IL-8 and/or IL-6 and/or TNFα levels when the individual has gingivitis. After first identifying that the individual has gingivitis, GCF samples at a healthy tissue site distant from the site of inflammation are collected from the individual who has gingivitis, such samples are analyzed to determine a distant healthy MIF level and/or a distant healthy CCL1 level which are then compared to baseline MIF level and/or baseline CCL1 level, respectively, so the individual can be identified as a high responder or slow responder. A slow responder who has gingivitis will have distant healthy MIF level and/or distant healthy CCL1 level (MIF and CCL1 levels at healthy sites distant from the site of inflammation) that are elevated compared to the baseline MIF and CCL1 levels.

When the individual develops gingivitis, samples from the GCF at healthy tissue sites distant for the site of inflammation may be collected 7-14 days after the appearance of plaque induced inflammation and after 14 days after the appearance of plaque induced inflammation to determine IL-8 and/or IL-6 and/or TNFα levels. GCF samples at a healthy tissue site distant from the site of inflammation are collected from the individual 7-14 days after the appearance of plaque induced inflammation (early samples) and after 14 days after the appearance of plaque induced inflammation (late samples) to determine IL-8 and/or IL-6 and/or TNFα levels which are then compared to baseline IL-8 and/or IL-6 and/or TNFα levels, respectively, so the individual can be identified as a high responder or slow responder. A high responder who has gingivitis will have elevated IL-8, IL-6 and TNFα levels at healthy sites distant from the site of inflammation compared to the baseline IL-8, IL-6 and TNFα levels 7-14 days after the appearance of plaque induced inflammation. A slow responder who has gingivitis will have elevated IL-8, IL-6 and TNFα levels at healthy sites distant from the site of inflammation compared to the baseline IL-8, IL-6 and TNFα levels after 14 days after the appearance of plaque induced inflammation.

In some embodiments, the plaque induced inflammation associated with gingivitis may be intentionally induced as part of a procedure to determine the inflammatory response type of an individual. After a cleaning and examination to confirm the absence of gingivitis, GCF samples may be taken and used to establish baseline levels of host mediators such as IL-1β, MIF, CCL-1, IL-8, IL-6 and TNF-α. The cleaning and examination start a 14-day pre-induction period (day −14 to day 0). On day 0, the individuals begins a 21-day induction period in which the individual refrains from brushing the entire mouth or a side of the mouth as in the experimental gingivitis model during which time the plaque induced inflammation associated with gingivitis develops. GCF samples may be taken at one or more sites of inflammation that develop during this period to establish gingival patient IL-1β levels. GCF samples may be taken at one or more sites of healthy tissue distant from a site of where inflammation has developed during this period, such as healthy tissue sites contralateral to a site of inflammation, to establish distant healthy levels of host mediators such as MIF and CCL-1. GCF samples may be taken at one or more sites of healthy tissue distant from a site of where inflammation has developed on days 7-14 of the induction phase (7-14 days after cessation from brushing; 21-28 days after cleaning and baseline sample collection), such as healthy tissue sites contralateral to a site of inflammation, to establish early distant healthy levels of host mediators such as IL-8, IL-6 and TNF-α. GCF samples may be taken at one or more sites of healthy tissue distant from a site of where inflammation has developed after 14 days of the induction phase (after 14 days after cessation from brushing; after 28 days after cleaning and baseline sample collection), such as healthy tissue sites contralateral to a site of inflammation, to establish late distant healthy levels of host mediators such as IL-8, IL-6 and TNF-α.

Methods provided herein include quantifying IL-1β and/or MIF and/or CCL1 and/or IL-8 and/or IL-6 and/or TNFα levels in the gingival crevice. Chemokines in the GCF may be quantified using GCF samples obtained from the individual. There are three widely practiced methods to collect the GCF. The most used method for GCF collection is made with specifically designed absorbent filter paper as endodontic paper points or periopapers. The endodontic paper points or periopapers are inserted into the gingival crevice and left in situ for 5 to 60 seconds, usually 30 seconds, to allow the GCF to be adsorbed by the paper. The GCF is eluted from the endodontic paper points or periopapers in saline. Another GCF collection method, the gingival washing technique, consists of perfusing the GCF with an isotonic solution, as Hank's balanced solution, with fixed volume. The fluid collected represents a dilution of crevicular fluid, containing cells and soluble constituents, as plasma proteins. A third GCF collection method is inserting capillary tubes, with specific diameter, into the entrance of the gingival crevice and the fluid migrates into the tube by capillary action. The GCF that are collected may be evaluated for neutrophil chemokine deregulation indicative of gingivitis.

The collected GCF may be analyzed to measure the quantity of IL-1β and/or MIF and/or CCL1 and/or IL-8 and/or IL-6 and/or TNFα using commercially available kits. Examples of such kits FlowCytomix™ kits from eBioscience® (formerly Bender MedSystems®, flow cytometry, non-magnetic beads), the Human Cytokine panel from Invitrogen™ (Luminex®, non-magnetic beads), the Bio-Plex Pro™ X-Plex Custom Assay from Bio-Rad® (Luminex®, magnetic beads) and (iv) the MILLIPLEX® Kit from Millipore™ (Luminex®, magnetic beads). Multiplex kits with magnetic beads (Luminex®) from Invitrogen™ and BD™ Cytometric Bead Array (CBA) Human Enhanced Sensitivity kits (flow cytometry, non-magnetic beads) can be used.

Some embodiments relate to methods of treating an individual who has been identified as having gingivitis. Methods of treatment comprise identifying that the individual as being a slow responder or a high responder and then treating the individual based upon whether they are a slow responder or a high responder. Some embodiments relate to methods of preventing gingivitis. Methods of preventing gingivitis comprise identifying that the individual as being a slow responder or a high responder and then treating the individual based upon whether they are a slow responder or a high responder.

The individual may be identified as a high responder or slow responder by obtaining a sample of gingival crevicular fluid from the individual who has gingivitis at the site of inflammation, measuring the IL-1β level in it and comparing that level to baseline IL-1β level. which is established by having previously obtained a sample of gingival crevicular fluid from the individual when the individual did not have gingivitis and measuring the IL-1β level at that time.

A method of identifying an individual who has gingivitis as being a slow responder or a high responder may comprise first determining the individual's baseline or non-gingivitis IL-1β level by obtaining a sample of gingival crevicular fluid from the individual when the individual did not have gingivitis and measuring the IL-1β level at that time. Subsequently, when the individual has been identified as having gingivitis the individual's gingivitis IL-1β level is measured by obtaining a sample of gingival crevicular fluid from the individual when the individual has gingivitis and measuring the IL-1β level at that time. The gingivitis IL-1β level is compared to the baseline IL-1β level. The individual who has gingivitis is identified as a slow responder if the gingivitis IL-1β level is not significantly elevated compared to the baseline IL-1β level. The individual who has gingivitis is identified as a high responder if the gingivitis IL-1β level is significantly elevated compared to the baseline IL-1β level.

The individual may be identified as a high responder or slow responder by obtaining a sample of gingival crevicular fluid from the individual who has gingivitis at a healthy tissue site distant from the site of inflammation, such a site contralateral to the site of inflammation, measuring the MIF level and/or CCL1 level in it and comparing that level to baseline MIF level and/or baseline CCL1 level, respectively, which may be established by having previously obtained a sample of gingival crevicular fluid from the individual when the individual did not have gingivitis and measuring the MIF level and/or CCL1 level at that time.

A method of identifying an individual who has gingivitis as being a slow responder or a high responder may comprise first determining the individual's baseline or non-gingivitis MIF level and/or the individual's baseline or non-gingivitis CCL1 level by obtaining a sample of gingival crevicular fluid from the individual when the individual did not have gingivitis and measuring the MIF level and/or CCL1 level at that time. Subsequently, when the individual has been identified as having gingivitis the individual's distant healthy MIF level and/or distant healthy CCL1 level is measured by obtaining a sample of gingival crevicular fluid from the individual when the individual has gingivitis at a healthy tissue site distant from the site of inflammation, such a site contralateral to the site of inflammation, and measuring the distant healthy MIF level and/or distant healthy CCL1 level at that time. The distant healthy MIF level and/or distant healthy CCL1 level is compared to the baseline MIF level and/or baseline CCL1 level, respectively. In an individual who has gingivitis and is a slow responder, the distant healthy MIF level and/or distant healthy CCL1 level is significantly elevated compared to the baseline MIF level and/or baseline CCL1 level, respectively. In an individual who has gingivitis and is a high responder, the distant healthy MIF level and/or distant healthy CCL1 level is not significantly elevated compared to the baseline MIF level and/or baseline CCL1 level, respectively.

In some embodiments, identifying an individual as being a slow responder or a high responder may be based on the temporal difference in the increase in IL-8 and/or IL-6 and/or TNFα at a healthy tissue site distant from a site of plaque induced inflammation. A method of identifying an individual who has gingivitis as being a slow responder or a high responder may comprise first determining the individual's baseline or non-gingivitis IL-8 level and/or the individual's baseline or non-gingivitis IL-6 level and/or the individual's baseline or non-gingivitis TNFα level by obtaining a sample of gingival crevicular fluid from the individual when the individual did not have gingivitis and measuring the IL-8 level and/or IL-6 level and/or the TNFα level at that time, thereby establishing the baseline IL-8 level and/or baseline IL-6 level and/or the baseline TNFα level. Subsequently, 7-14 days after the appearance of plaque induced inflammation (or if following an induction model, 21-28 days after cleaning, examination, which is 7-14 days after cessation of brushing), the individual's early distant healthy IL-8 level and/or early distant healthy IL-6 level and/or early distant healthy TNFα level is measured by obtaining a sample of gingival crevicular fluid from the individual when the individual has gingivitis at a healthy tissue site distant from the site of inflammation, such a site contralateral to the site of inflammation, and measuring the early distant healthy IL-8 level and/or early distant healthy IL-6 level and/or early distant healthy TNFα level at that time. After 14 days after the appearance of plaque induced inflammation (or if following an induction model, after 28 days after cleaning, examination, which is after 14 days after cessation of brushing), the individual's late distant healthy IL-8 level and/or late distant healthy IL-6 level and/or late distant healthy TNFα level is measured by obtaining a sample of gingival crevicular fluid from the individual when the individual has gingivitis at a healthy tissue site distant from the site of inflammation, such a site contralateral to the site of inflammation, and measuring the late distant healthy IL-8 level and/or late distant healthy IL-6 level and/or late distant healthy TNFα level at that time. The early distant healthy IL-8 level and/or early distant healthy IL-6 level and/or early distant healthy TNFα level at that time and the late distant healthy IL-8 level and/or late distant healthy IL-6 level and/or late distant healthy TNFα level may be compared to baseline IL-8 level and/or baseline IL-6 level and/or baseline TNFα level, respectively. In an individual who is a slow responder, the early distant healthy IL-8 level and/or early distant healthy IL-6 level and/or early distant healthy TNFα level is not significantly elevated compared to the baseline IL-8 level and/or baseline IL-6 level and/or baseline TNFα level, respectively but the late distant healthy IL-8 level and/or late distant healthy IL-6 level and/or late distant healthy TNFα level is significantly elevated compared to the baseline IL-8 level and/or baseline IL-6 level and/or baseline TNFα level, respectively. In an individual who is a high responder, the early distant healthy IL-8 level and/or early distant healthy IL-6 level and/or early distant healthy TNFα level is significantly elevated compared to the baseline IL-8 level and/or baseline IL-6 level and/or baseline TNFα level, respectively. Likewise, the late distant healthy IL-8 level and/or late distant healthy IL-6 level and/or late distant healthy TNFα level is significantly elevated compared to the baseline IL-8 level and/or baseline IL-6 level and/or baseline TNFα level, respectively.

In some embodiments identifying an individual as being a slow responder or a high responder based on the temporal difference in the increase in IL-8 and/or IL-6 and/or TNFα at a healthy tissue site distant from a site of plaque induced inflammation can be done by inducing plaque induced inflammation. In such embodiments, the baseline IL-8 level and/or baseline IL-6 level and/or baseline TNFα level are established by obtaining samples of gingival crevicular fluid from the individual after a professional cleaning and examination to confirm the absence of inflammation. Plaque induced inflammation may be induced by, 14 days after the professional cleaning and examination (a 14-day pre-induction period), refraining from brushing or other preventative care, which is called an induction phase or induction period during which time plaque induced inflammation is induced. Typical induction period is 21 days. Early distant healthy samples of GCF are collected between days 7-14 of the induction period (between 21-28 days after the professional cleaning and examination at the beginning of the pre-induction phase) from healthy sites distant from a site of inflammation, such a site contralateral to the site of inflammation. IL-8 and/or IL-6 and/or TNFα quantities in the sample of early distant GCF are measured to establish early distant healthy IL-8 level and/or early distant healthy IL-6 level and/or early distant healthy TNFα level. Late distant healthy samples of GCF are collected between after 14 after the induction period starts (after 28 days after the professional cleaning and examination at the beginning of the pre-induction phase) from healthy sites distant from a site of inflammation, such a site contralateral to the site of inflammation. IL-8 and/or IL-6 and/or TNFα quantities in the sample of late distant GCF are measured to establish late distant healthy IL-8 level and/or late distant healthy IL-6 level and/or early distant healthy TNFα level.

Individuals identified as having gingivitis may be treated to resolve the gingivitis based upon whether they are a slow responder or a high responder. Methods of treating an individual who has gingivitis comprise identifying an individual who has gingivitis as being a slow responder or a high responder by a method described above and then treating such individual based upon whether the individual is identified as a slow responder or a high responder.

In some embodiments, the individual who has gingivitis and has been identified as being a slow responder may be treated by applying to the individual's oral cavity an oral care composition that is an anti-bacterial oral rinse. In some embodiments, the individual who has gingivitis and has been identified as being a slow responder may be treated by applying to the individual's oral cavity an oral care composition comprising one or more ingredients selected from the group consisting of: arginine, zinc phosphate, zinc oxide, zinc citrate, triclosan, digluconate, thymol, menthol, eucalyptol, methyl salicylate, saline, antibiotics and fluoride.

In some embodiments, the individual who has gingivitis and has been identified as being a high responder may be treated by applying to the individual's oral cavity an oral care composition comprising anti-bacterial components such as one or more ingredients selected from the group consisting of: arginine, zinc phosphate, zinc oxide, zinc citrate, triclosan, digluconate, thymol, menthol, eucalyptol, methyl salicylate, saline, antibiotics and fluoride and further comprising anti-inflammatory components such as one or more ingredients selected from the group consisting of: chlorhexidine, DHA and vitamin D. In each instance, the various components may be included in a single oral care composition or in two or more separate oral care compositions.

EXAMPLES

Example 1

Materials and Methods

Human Induced Gingivitis Experiment

The study methodology was based on the established protocol by Loe (Löe et al. 1965 Experimental gingivitis in man. Journal of periodontology 36(3):177-187.) for induction of reversible bacterial-induced inflammation via cessation of oral hygiene in humans. With approval of the applicable Human Subjects Review Committee twenty-one generally healthy adults aged 18-35 years were consented and enrolled following the principles of the declaration of Helsinki. All study participants underwent informed consent process with a thorough discussion of study participation details, prior to enrollment in the study. The inclusion and exclusion criteria were confirmed. All female participants were provided with a pregnancy test prior to enrollment.

For inclusion, subjects had gingival health with no clinical signs of gingival inflammation at >90% of sites at time of screening and had no signs of periodontal disease. To be enrolled the participant met the following inclusion criteria: 1) aged 18-35 years; 2) in good general health, ASA I; 3) no clinical signs of gingival inflammation at >90% of sites observed at time of screening; 4) probing depth (PD) ≤3.0 mm; 5) attachment loss (AL)=0 mm; 6) gingival health at baseline visit in the sites of interest (Day 0): gingival Index (GI)=0 and bleeding on probing (BOP)(−); 7) fluent in English. Exclusion criteria included: 1) medical condition which requires premedication prior to dental treatments/visits; 2) subjects unable or unwilling to sign the informed consent form; 3) history of periodontal disease; 4) history of systemic inflammatory or immune conditions; 5) use of antibiotic or anti-inflammatory drugs within 30 days of enrollment; 6) pregnant or breastfeeding at the time of screening; 7) concurrent orthodontic treatment; 8) untreated carious lesions and/or inadequate restorations on maxillary posterior teeth; 9) participation in any other clinical study or test panel within 1 week prior to enrollment into this study; 10) use of tobacco products; 11) subjects who must receive dental treatment during the study dates; 12) orthodontic bands, appliances, or crowns and bridges, or removable partial dentures affecting the maxillary posterior teeth; 13) history of allergy to common dentifrice ingredients; 14) immune-compromised individuals (HIV, AIDS, and immune-suppressive drug therapy).

Using online randomization tool (2017 GraphPad Software), in each participant, one maxillary quadrant was assigned randomly as test quadrant (experimental gingivitis) and contralateral quadrant as control. In each test and control quadrant, the following three maxillary teeth were used: first premolar, second premolar, and first molar. If a premolar was missing, the second molar replaced it. Clinical examination and sample collection were performed on the mesio-buccal and mesiopalatal surfaces of each study tooth.

The study included the following phases 1) Hygiene phase for two weeks prior to baseline (Day −14-Day 0), 2) Gingivitis induction phase lasting for three weeks (Day 0-Day 21), and 3) Resolution phase for two weeks (Day 21-Day 35) (FIG. 1A). During the experimental induction phase the subjects were given customized intraoral stents that prevented oral hygiene at the experimental sites. Fidelity monitoring of the intervention was conducted at each timepoint throughout the experiment by clinical assessment of the plaque index.

At Day −14, after obtaining informed consents and verification of inclusion/exclusion criteria, full clinical assessment and biospecimens collection were performed. After obtaining a maxillary impression for stent fabrication, full mouth prophylaxis was administered and thorough oral hygiene instructions were given. Participants returned 7 to 14 days after this initial visit and their baseline (Day 0) measurements and biospecimens collection were acquired. The acrylic stent was given to the participant with detailed instructions for use during regular brushing with the purpose of preventing accidental brushing of the experimental sites. Participants were instructed not to brush teeth on the test side (under the provided stent) and not to use any other measure of oral hygiene such as flossing or interdental aids. For the control side and rest of the mouth, participants were instructed to use the provided toothbrush (Colgate® Gum Comfort Toothbrush), toothpaste (Colgate® Cavity Protection Great Regular Flavor Fluoride Toothpaste), and dental floss (Oral B Glide), and to refrain from using mouth rinses and chewing gums during entire study period. Participants returned on Day 4 and on weekly basis afterward, clinical assessments were performed and samples collected each time using the same criteria as at the baseline visit. The course of the "no brushing" part of the experiment lasted 21 days to allow all the participants to develop gingivitis. After acquiring samples and clinical assessment on day 21, additional thorough prophylaxis was administered. Participants were given again detailed instructions in oral hygiene methods using the provided electric toothbrush (Philips Sonicare Electric Toothbrush), toothpaste (Colgate® Cavity Protection Great Regular Flavor Fluoride Toothpaste), and dental floss (Oral B Glide) beginning the same day and continued twice daily during the resolution phase. Assessment of gingival condition and biospecimens collection continued weekly during the reversal phase. Medical history and exclusion criteria were reviewed at each study visit.

The stent was fabricated to include only the occlusal surface of the study teeth and eliminate contact with the cervical margin of each tooth, thereby reducing the risk of plaque being disturbed during insertion or removal of the stent. The stent was constructed from 3-mm-thick plastic mouthguard material. Elimination of cervical contact was accomplished by blocking out around the gingival margin and proximal surfaces using a spacer made from 1-mm-thick mouthguard material. The stent was trimmed vertically on the buccal side to a length just short of the vestibule and extending 4-5 mm on the palatal side. Also, it was trimmed medially to the middle of the canine, and distally to the middle of the second molar.

Following biospecimens collection, clinical data were documented based on probing depth (PD), attachment level (AL), plaque index (PI), gingival index (GI), and bleeding on probing (BOP). All clinical measurements were conducted using a manual UNC-15 periodontal probe (Hu-Friedy, Chicago, IL, USA). BOP was recorded within 20 seconds of probing. Characterization of in vivo chemokine responses during experimental gingivitis At each timepoint, local chemokine responsiveness was measured in gingival transudate, i.e. Gingival Crevicular Fluid (GCF). For each study visit, GCF samples were collected first followed by acquiring plaque samples. Subsequent to biospecimens collection, clinical indices were recorded. GCF samples were collected from the mesiobuccal and mesiopalatal surfaces of teeth (#'s 3, 4, 5, 12, 13 and 14). The sites to be sampled were isolated with cotton rolls to avoid contamination from saliva and gently air-dried in an apico-coronal direction without disrupting supragingival plaque. Eight index teeth sites were isolated and sampled without disrupting supragingival plaque by gentle insertion of sterile paper strips (Periopaper; Oraflow Inc., Smithtown, NY, USA) into the gingival crevice until mild resistance is felt and left in place for 30 seconds. Samples from the sites were pooled and placed immediately on ice and transported to the lab for processing. Samples from contralateral control teeth were also collected. The volume of GCF samples was collected and immediately quantified with a previously calibrated measuring device (Periotron 8010; OraFlow Inc, Smithtown, NY, USA) which measures the electrical capacitance of a wet strip placed between the jaws of the device. Periotron 8010 was calibrated with known volumes of distilled water in triplicate and a standard calibration curve was generated. Gingival crevicular fluid volumes were calculated from the Periotron scores using the Periotron Professional Software V3.0 (OraFlow Inc, Smithtown, NY, USA) utilizing a 4th order polynomial regression. Paper strips visibly contaminated with saliva and blood were excluded from the study. At each study visit, a total of six periopapers were collected per study side and then pooled into a single microcentrifuge tube. Samples were placed immediately on ice and transported to the lab for processing.

To retrieve GCF proteins, GCF samples were eluted in 200 µl sample diluent (Bio-Plex Pro™ Human 40-plex Chemokine Panel, Bio-Rad Laboratories, Hercules, CA, USA) with 0.5% bovine serum albumin (Blocker™ BSA (10×) in PBS; Waltham, MA, Thermo Scientific, USA) and then continuously mixed on a tube rotator for 60 minutes at 4° C. The 1.5 mL tubes were centrifuged at 13,000 rpm for 1 min at 4° C. to extract the fluid from the paper strips. Paper strips were then removed and eluted samples were stored at −80° C. until further analysis. Samples were immediately thawed prior to performing immunoassays.

The concentrations of myeloperoxidase (MPO), which is a good marker of neutrophils infiltration, were quantified using a commercially available ELISA kit (Instant ELISA®, Affymetrix eBioscience, San Diego, CA, USA) according to manufacturer's instruction. The assay has detection range between 156 pg/ml and 10,000 pg/ml.

GCF samples were added in duplicate to the wells of precoated 96-well plates with anti-human MPO antibodies at a 1:200 dilution. Samples were incubated at room temperature for 3 hours; the biotin-conjugated detection antibodies bind to MPO captured by coating antibodies followed by Streptavidin-HRP binding to the biotinylated antihuman MPO antibodies. After the washing step, a substrate solution (TMB) was added to visualize the enzymatic reaction. The reaction was stopped with the addition of stop solution (Sulphuric acid) and absorbance was measured on a microplate reader at 450 nm (VMax microplate reader; Molecular Devices Sunnyvale, CA, USA). A standard curve was determined from seven human MPO standard dilutions. Concentrations for MPO in the samples were calculated from the standard curve with a five-parameter fit curve (Softmax Pro Software; Molecular Devices Sunnyvale, CA, USA).

Bead based multiplex analysis was performed on GCF samples (Bio-Plex Pro™ Human 40-plex Chemokine Panel; Bio-Rad Laboratories, Hercules, CA, USA) allowing for simultaneous quantification of multiple chemokines. The following list of chemokines were analyzed with the assay working range level in pg/ml shown in parenthesis ( ): 6Ckine/CCL21 (21.9-3,923), BCA-1/CXCL13 (0.7-1,200), CTACK/CCL27 (1.2-5,000), ENA-78/CXCL5 (7.3-120,000), Eotaxin/CCL11 (1.5-3,859), Eotaxin-2/CCL24 (6.2-4,073), Eotaxin-3/CCL26 (0.9-12,109), Fractalkine/CX3CL1 (4-11,463), GCP-2/CXCL6 (0.8-11,135), GM-CSF (5.3-35,000), Gro-α/CXCL1 (3.1-7,024), Gro-β/CXCL2 (4.6-13,257), I-309/CCL1 (1.8-1,015), IFN-γ (2.3-20,236), IL-1β (0.4-7,000), IL-2 (0.8-13,000), IL-4 (1.2-4,804), IL-6 (0.7-12,000), IL-8/CXCL8 (0.5-7,640), IL-1β (1.3-18,708), IL-16 (2.1-34,000), IP-10/CXCL10 (1.6-7,714), I-TAC/CXCL11 (0.1-2,298), MCP-1/CCL2 (0.3-4,812), MCP-2/CCL8 (0.3-4,056), MCP-3/CCL7 (1.9-20,133), MCP-4/CCL13 (0.2-3,368), MDC/CCL22 (0.9-14,649), MIF (23.1-377,724), MIG/CXCL9 (1.8-19,600), MIP-1α/CCL3 (0.4-1,543), MIP-1δ/CCL15 (1.7-9,100), MIP-3α/CCL20 (0.3-4,675), MIP-3β/CCL19 (3.0-48,494), MPIF-1/CCL23 (1.0-14,450), SCYB16/CXCL16 (0.5-2,867), SDF-1α+β/CXCL12 (8.3-115,730), TARC/CCL17 (1.7-430), TECK/CCL25 (20.6-114,493), and TNF-α (0.9-13,879). Samples were not diluted for the assay and mediator data are reported in total amounts per sample collected in 30 seconds (pg per 30-s sample). Briefly, different fluorescently dyed magnetic microspheres populations were covalently conjugated with capture antibodies specific for the different chemokines. In the multiplex immunoassay, the coupled beads were incubated with 50 µl of GCF samples or standards in a 96-well plate in duplicate at room temperature for one hour. After washing (Bio-Plex Pro Wash Station; Bio-Rad, Hercules, CA, USA), 25 µl of biotinylated detection antibodies was added and incubated for 30 minutes at room temperature. After incubation, wells were washed and 50 µl streptavidin-phycoerythrin as a reporter was added to each well and incubated for 10 min. After the wash cycle was completed, 125 µl of assay buffer was added to each well. The data was obtained using a flow cytometry laser detection system (Bio-Plex 200 reader; Bio-Rad Laboratories, Hercules, CA, USA) by acquiring the signal from the fluorescent dye within each bead for assay identification along with the fluorescent signal from the reporter for quantification.

The concentrations of different chemokines were calculated based on the respective standard curve for each chemokine with a five-parameter logistic (5PL) equation (Bio-Plex Manager Software V6; Bio-Rad Laboratories, Hercules, CA, USA). Mediators data are reported in total amounts per sample collected in 30 seconds (pg per 30-s sample). Mean values and standard deviations of the total amount per 30-s sample for the chemokines and MPO were computed at each study visit for both the control and test sides.

Characterization of Microbial Changes in Response to Plaque Accumulation

Subgingival plaque samples were collected at each study visit from both control and test sides. Sterile paper points (STER-I-CELL Paper Points, Size M; Coltene, Whaledent, Cuyahoga Falls, OH, USA) were inserted into the gingival sulcus of the six maxillary teeth for 30 seconds. At each study visit, a total of six samples per study side were collected and pooled and samples were transported to the lab on ice and then frozen at −80° C. until further analysis. DNA was extracted using a commercially available kit (QIAamp DNA Microbiome Kit; Qiagen, Germany) following the manufacturer's protocol, that uses both mechanical and chemical cell lysis. Sample purification and quality control were performed as previously described.

For DNA extraction negative controls were implemented by performing the DNA extraction protocol without plaque samples with either kit reagents only or kit reagents with the sterile paper points to assess for contamination. Also, to validate the efficiency of the technique, positive controls using known bacterial cultures were included. Quantitative real-time PCR was performed to determine the total bacterial load in each sequenced sample. A qPCR standard curve was generated from serially diluted *Fusobacterium nucleatum* ATCC 10953 genomic DNA.

Analysis of merged 300 bp paired-end reads (average length 450 bp) was performed using the Quantitative Insights into Microbial Ecology QIIME2 following the Divisive Amplicon Denoising Algorithm 2 (DADA2) pipeline workflow to generate amplicon sequence variants (ASV's). Taxonomic assignment to classify ASV's was performed using the Human Oral Microbiome Database (HOMD 16S rRNA RefSeq v. 15.1). Data were integrated into a single object using the "phyloseq" R package and further analyzed.

Sample purification was performed using a purification kit (the DNA Clean & Concentrator −5 kit; Zymo Research, Orange, CA, USA) to further purify and increase the DNA yield. After DNA extraction and purification, DNA concentrations in the samples were determined fluorometrically (Quanti-iT dsDNA HS Assay Kit; Invitrogen, Carlsbad, CA, USA) with Fluorometer (Qubit 2.0; Life Technologies, Carlsbad, CA, USA). Samples were stored at −20° C. until ready for sequencing.

Comprehensive microbial profiling of subgingival plaque samples was performed via high throughput sequencing of 16S rRNA gene following the standard Illumina Miseq System protocol. Briefly, amplification of DNA was performed using primers with overhang Illumina flow cell adapter sequences targeting hypervariable (V3 and V4) regions of the bacterial 16s rRNA gene. The primers used were as follows:

```
SEQ ID NO: 1 was the 16S amplicon
PCR forward primer:
5'-TCGTCGGCAGCGTCAGATGTGTATAAGAGACAGCCTACGGGNGGCWG
CAG-3'

SEQ ID NO: 2 was the 16S amplicon
PCR reverse primer:
5'-TCTCGTGGGCTCGGAGATGTGTATAAGAGACAGGACTACHVGGGTAT
CTAATCC-3').
```

Samples were amplified in singletons in a 96 well plate format. Each reaction was performed using a PCR kit (KAPA HiFi HotStart ReadyMix; KAPA Biosystems, Boston, MA, USA) in a total volume of 25 µl which included the following reagents: 2.5 µl of extracted DNA, 5 µl of both forward and reverse primers (1 µM each primer) and 12.5 µl of 2×KAPA HiFi HotStart ReadyMix. Amplicon PCR was performed on a thermocycler (C1000 Touch thermal cycler; BioRad, Hercules, CA, USA) utilizing the following program: a denaturation stage at 95° C. for 3 minutes, followed by 35-40 cycles of denaturation at 95° C. for 30 seconds, annealing at 55° C. for 30 seconds and extension at 72° C. for 30 seconds, and then a final extension stage at 72° C. for 5 minutes. The generated amplicons from the first PCR were approximately 460 bp in size which was verified visually by running each reaction on 1% agarose gel electrophoresis at 100V for 30 minutes. Amplicons were subsequently purified using magnetic beads (Agencourt AMPure XP beads; Agencourt Bioscience Corporation, Beckman Coulter Inc., Beverly, MA, USA) and indexed (Nextera XT v2 Index Kits, Set A, B, and D; Illumina, San Diego, CA, USA). The indexing PCR conditions included a denaturation stage at 95° C. for 3 min, followed by 8 cycles of denaturation at 95° C. for 30 s, annealing at 55° C. for 30 s, and extension at 72° C. for 30 s, and then a final extension stage at 72° C. for 5 min. The indexed PCR amplicons were further purified with magnetic beads (Agencourt AMPure XP beads; Agencourt Bioscience Corporation, Beckman Coulter Inc., Beverly, MA, USA), and the quality and size of the library were checked (High Sensitivity D1000 Reagents and Agilent 4200 TapeStation system; Agilent Technologies, Santa Clara, CA, USA). Subsequently, library normalization was achieved using a normalization kit (SequalPrep Normalization Plate Kit; ThermoFisher Scientific, Waltham, MA, USA). The normalized library was pooled and denaturated with sodium hydroxide (NaOH) (Fisher Scientific, Pittsburgh, PA, USA). The denatured library (20 pM) was spiked with at least 20% control DNA (PhiX Control v3 library, Illumina, San Diego, CA, USA) prior to loading to the sequencer. Paired-end sequencing was carried out on a sequencing platform (MiSeq System, Illumina, San Diego, CA, USA) using a 2×300 cycle sequencing kit (MiSeq Reagent Kits v3, Illumina, San Diego, CA, USA).

Analysis of sequencing data was performed using the Quantitative Insights into Microbial Ecology QIIME2 following the Divisive Amplicon Denoising Algorithm 2 (DADA2) pipeline workflow. A total of 16M paired-end reads were generated, average reads per sample was 41,017. Raw paired-end reads were imported to QIIME2 (v. 2018.2), following demultiplexing with Casava (v. 1.8), both forward and reverse reads were trimmed by 10 bp and truncated to 290 and 200 bp respectively. After quality filtering and denoising of sequences and removal of chimeras and singletons, a total of 2,219,156 high quality merged reads with a mean length of 452 bp were used for downstream analysis. Taxonomic assignment to classify the amplicon sequence variants (ASV's) was performed using the most up to date Human Oral Microbiome Database (HOMD 16S rRNA RefSeq v. 15.1), which is highly curated database that is specific for the human oral cavity and contains predominately full length 16S rRNA gene reference sequences. Samples were then filtered for taxonomic contaminants based on negative controls (kit reagents only or kit reagents with the sterile paper points). A phylogenetic tree was constructed using FastTree. Unrarefied data was used for the downstream analysis. The sequencing data were integrated into a single object using the "phyloseq" R package and all subsequent data analysis and plots were produced in R Studio. Alpha diversity, within sample diversity, were calculated using both richness and evenness metrics by functions estimate_richness and pd in the "phyloseq" and "picante" R packages. The plots for richness estimates were generated using the "ggplot2" package in R.

Community richness was measured by observed species: total count of unique ASV's in the sample and by the nonparametric richness estimator Chao1, which accounts for the number of singletons and doubletons. Total community diversity (richness and evenness) was measured by Simpson's inverse diversity index, Shannon index, and Faith's phylogenetic diversity (PD), which uses phylogenetic distances to calculate alpha diversity.

Beta diversity, between samples diversity, was determined using phylogenetic-based Unifrac distances, which measure phylogenetic distance between samples for both unweighted (presence\absence), weighted (relative abundance), and ASV based Bray-Curtis dissimilarity matrices that accounts for both the presence/absence and abundance of unique ASV's. Beta diversity metrics were calculated with ordinate function in "phyloseq" and were visualized by non-metric multidimensional scaling (NMDS) plots using plot ordination function in "phyloseq".

Quantitative real-time PCR was performed to determine the total bacterial load in each sequenced sample. Samples were analyzed in duplicates in a 96-well plate using a thermocycler (CFX96 Real-time system C1000 Thermocycler; BioRad Laboratories, Hercules, CA, USA). A qPCR standard curve was generated from serially diluted *Fusobacterium nucleatum* ATCC 10953 genomic DNA in a range of 108 to 101 16 s copy number. Each reaction was performed in a total volume of 20 µl consisted of 2 µl of DNA or standards added to 10 µl of the master mix (TaqMan™ Fast Advanced Master Mix; Applied Biosystems, Foster City, CA, USA). Primers set that specifically target the 16S rRNA gene were added with 900 nM final concentrations.

```
SEQ ID NO: 3 was the forward primer used:
5'-TCCTACGGGAGGCAGCAGT-3'.

SEQ ID NO: 4 was the reverse primer used:
5'-GGACTACCAGGGTATCTAATCCTGTT-3'.
```

In addition, 200 nM of TaqMan probe was used. The TaqMan probe used consisted of the fluorophore 6-carboxyfluorescein (FAM) covalently attached to the 5'-end of the oligonucleotide probe having SEQ ID NO:5 and the quencher tetramethylrhodamine (TAMRA) covalently attached to the 3'-end. Thus, the TaqMan probe had the structure, (6-FAM)-(SEQ ID NO:5)-(TAMRA). SEQ ID NO:5 is the oligonucleotide of the TaqMan probe and has the sequence:

```
5'-CGTATTACCGCGGCTGCTGGCAC-3'.
(Sigma Aldrich, St Louis, MO, USA)
```

Nuclease-free water was added to bring the total volume of the reaction to 20 µl. The negative control sample was included in the run using nuclease-free water to ensure no contamination occurred. The qPCR run consisted of the following amplification conditions: 50° C. for 2 minutes (UNG incubation); 95° C. for 20 seconds (Polymerase activation); 40 cycles of 95° C. for 3 seconds (denature) and 60° C. for 30 seconds (anneal/extend). The subgingival bacterial load was calculated (BioRad CFX software V3.1; BioRad Laboratories, Hercules, CA, USA) using regression mode (Cq determination mode).

Variation in Clinical Gingival Inflammatory Responses

Clinical data including plaque index (PI), gingival index (GI), bleeding on probing (BOP) were assessed at each timepoint as measures clinical inflammation. All measurements were performed by a single, trained examiner using the same type of graded periodontal probes during the following study phases: health (Days −14-0), induction phase (Days 4, 7, 14 and 21), and resolution phase (Days 28, 35). To identify clusters of inflammatory responses among participants we assessed joint clinical data trajectories of gingivitis severity represented by GI and BOP in response to plaque accumulation represented by PI from Day 0 to Day 21 in the test sides using an implementation of k-means specifically design to cluster joint trajectories.

Statistical Analysis

Participants were clustered into groups based on the joint clinical data trajectories of gingivitis severity represented by GI and BOP in response to plaque accumulation represented by PI between Day 0 and Day 21 in the test sides. The clustering analysis was performed using the kmeans for longitudinal data method in the "kml3d" R package and using Euclidean distances with Gower adjustments for partitioning. The optimal number of clusters was determined using Calinski-Harabasz criterion One-way ANOVA and Chi-square test were conducted to compare the responder groups age and gender, respectively.

Clinical and mediator data across test and control sites were summarized into single average score per person at each time point and were reported using boxplots showing medians and interquartile ranges. Clinical data including PI, GI, BOP and GCF volume, and immunoassay data including chemokine and MPO total amount (pg per 30-s sample) were summarized into a single average score per side at each time point. The GCF mediators data were variable and were not normally distributed, to address that, all mediators values were transformed using a Log 10 (X+1) transformation. Data were reported in means and standard deviations. All statistical analyses were performed using R Studio. Tables for clinical and chemokine data were created using "expss" package.

The comparisons between test and control sides over time were performed using a linear mixed-model, that included a parametric analysis of variance (ANOVA), with the side (test vs control) and Day as the fixed effect and the subject as the random effect. Statistical models were performed using the function lmer in the "lmerTest" package and implemented in the "lmerTest" package in R statistical software. Fixed effects comparisons between test and control sides, and over-time changes within each group were performed using linear mixed-model, that included a parametric analysis of variance (ANOVA), with the Day as the fixed effect and the subject as the random effect. Post hoc False Discovery Rate (FDR) corrected pairwise comparisons were reported using emmeans function in the "emmeans" package in R. Multiple comparisons were performed between test and control sides during induction phase (Day 0, 4, 7, 14 and 21), and within test sides between baseline (Day 0) and different time points during induction phase (Day 4, 7, 14 and 21). Statistical significance was considered when p values were <0.05. Boxes in figures represent data and medians ±interquartile ranges; whiskers and outliers >1.5 IQR. Trend lines represent mean values across time points. Statistically significant difference between test and control sides at each visit during induction phase are shown above the bars and their significance level indicated by asterisks. Significance levels: *p<0.05, p<0.01 or *p<0.001. In addition, statistically significant difference for the time trend on the test side induction phase values (Day 4, 7, 14 and 21) compared to baseline (Day 0) are shown above the bars and their significance level indicated by asterisks. Significance levels: *p<0.05, p<0.01 or *p <0.001.

To determine the mechanisms responsible for homing neutrophils through inflamed oral junctional epithelia in bacterial-induced inflammation the distributions of neutrophil MPO levels, which are reflective of neutrophil numbers, were analyzed and known mediator chemokines responsible for neutrophil migration over time. Clinical and mediators data for responder groups were summarized into a single average score per group at each time point for the normalized (row-wise Z-score) heatmap display (FIG. 3A) which show the Z scores values for chemokine expression across all rows (responder groups and controls) with all responder groups for the control combined by day.

As summarized above, statistical tests based on a linear mixed-model were used to compare clinical and chemokine data between different responder groups during induction phase (Day 0, 4, 7, 14 and 21), and within each responder group between baseline (Day 0) and different time points during induction phase (Day 4, 7, 14 and 21). Boxes in figures represent data and medians ±interquartile ranges; whiskers and outliers >1.5 IQR. Trend lines represent mean values across time points. In order to display on the graph, the differences in the responder groups at a particular day, a compact letter display strategy is used. Letter displays allow efficient reporting of pairwise treatment comparisons. Different letters above bars indicate the significant differences between groups at that time point (a, b, c). Different letters denote significant differences, p<0.05. The groups with different letters are significantly different, meanwhile groups with same letters are not different. If a group has two letters, then that group is not statistically different from the groups which also share those letters. In addition, differences of each group compared to baseline (Day 0) are shown above the groups and their significance level indicated by asterisks. Significance levels: *p<0.05, p<0.01 or *p<0.001.

Because the experimental bacterial driven induction and resolution of gingivitis led to an inverted-U shape distribution of bacterial biomass (total bacterial 16S rRNA gene copies) in vivo, quadratic regression models were employed to better study the temporal changes of MPO and the two major neutrophil signaling chemokines, MIF & IL-8/CXCL8, in response to microbial accumulation across study timepoints. Quadratic regression models were implemented in R using second degree polynomials and coefficient directions and p-values representing the quadratic terms are reported.

Statistical analysis of the changes in subgingival microbial composition and load longitudinally during gingivitis induction were performed using R Software (v. 3.5.1). Logarithmic transformations (base 10) were performed for the subgingival bacterial load data prior to analysis. In a similar manner to clinical data, the difference in subgingival microbial load and alpha diversity indices between test and control sides, as well as between different responder groups were determined using linear mixed-models.

Differences in microbial community composition between test and control sides, or between different responder groups over time, were evaluated by performing permutational analysis of variance (PERMANOVA) on the calculated beta diversity matrices (Bray-Curtis and UniFrac distances) using the function adonis in the "vegan" package (v. 2.5-4). Between groups multiple comparisons were performed by pairwise PERMANOVA using the function pairwise.perm.manova from the "RVAideMemoire" package with false discovery rate (FDR) adjustment.

To identify statistically significant differences among agglomerated and normalized amplicon sequence variants (ASV's) between samples and responder groups we applied both the unpaired non-parametric Kruskal Wallis one-way analysis of variance (anova) and the nonparametric Wilcoxon-Mann-Whitney test—both with a 95% confidence interval ($\alpha$=0.05) with false discovery rate (FDR) adjustment—via the "rsatix" and "ggpubr" R packages using centered log ratio (CLR) transformed data generated with the "microbiome" R package. Boxplots in figures show median and lower/upper quartiles; whiskers show inner fences. (Wilcox test; adjusted by FDR; Table 4, a genus level statistical analysis between control and groups to FIG. 3A). Stars show FDR-corrected statistical significance levels (FDR *P≤0.05, P≤0.01, *P≤0.001, ****P≤0.0001).

Figure 9:
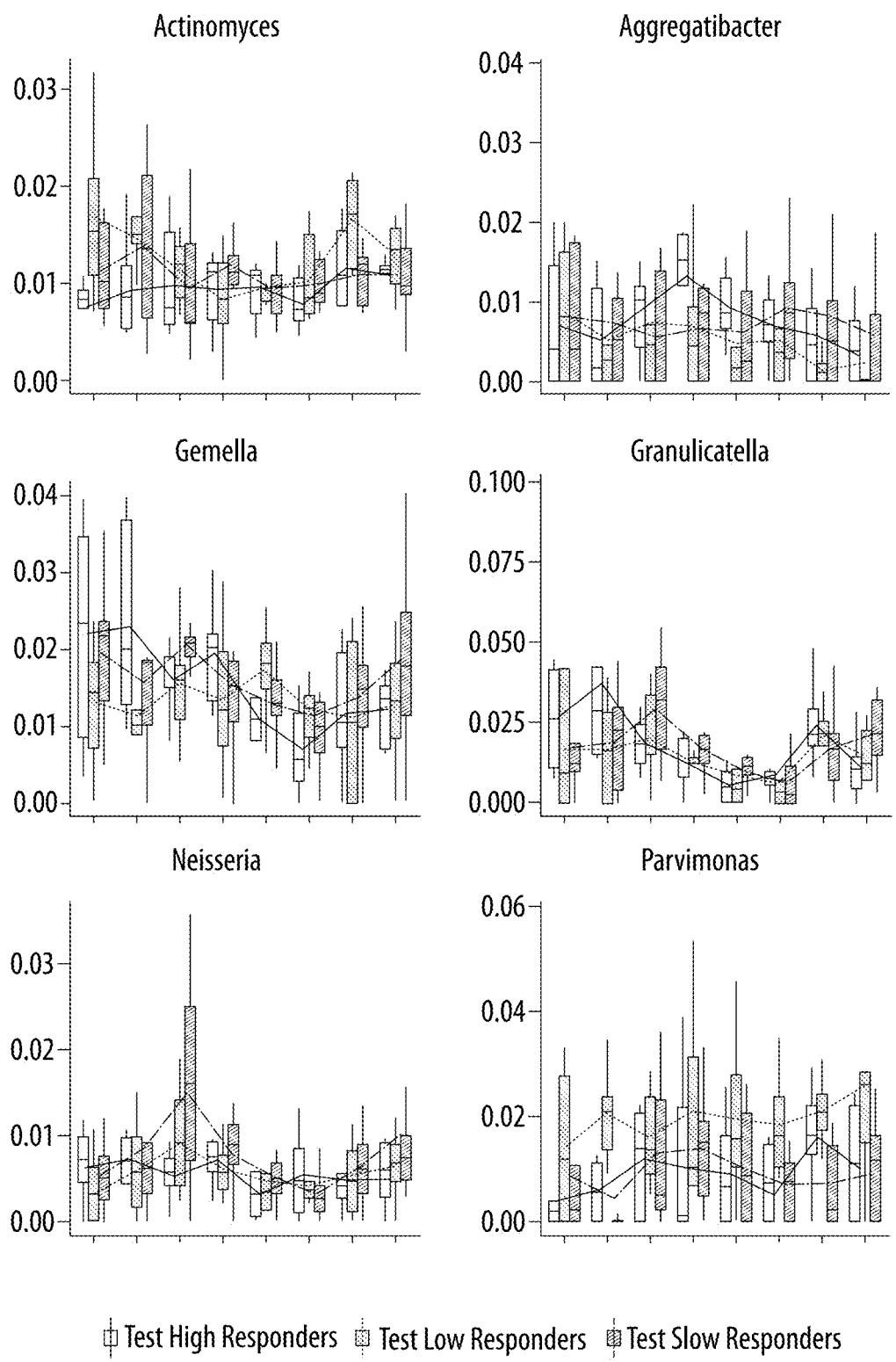
FIG. 9 contains data showing temporal changes in genus level diversity between responder type by day. Amplicon sequence variant (ASV) abundances were agglomerated to the genus level using a novel mean agglomeration strategy from Day −14 to Day 35 by responder group: High, Low, and Slow (n=293 test side samples from 21 subjects). Boxplots show mean and lower/upper quartiles of transformed data using a pseudo count (10−6) and % mean agglomerated abundance of ASV's at the genus level; whiskers show inner fences; grey dots represent outliers. Lines represent the linear regression (Loess) for each respective responder group, High, Low, and Slow, from Day −14 to Day 35. Statistical comparisons between groups were conducted at genus level assignments using the agglomerated ASV means.
Figure 9:
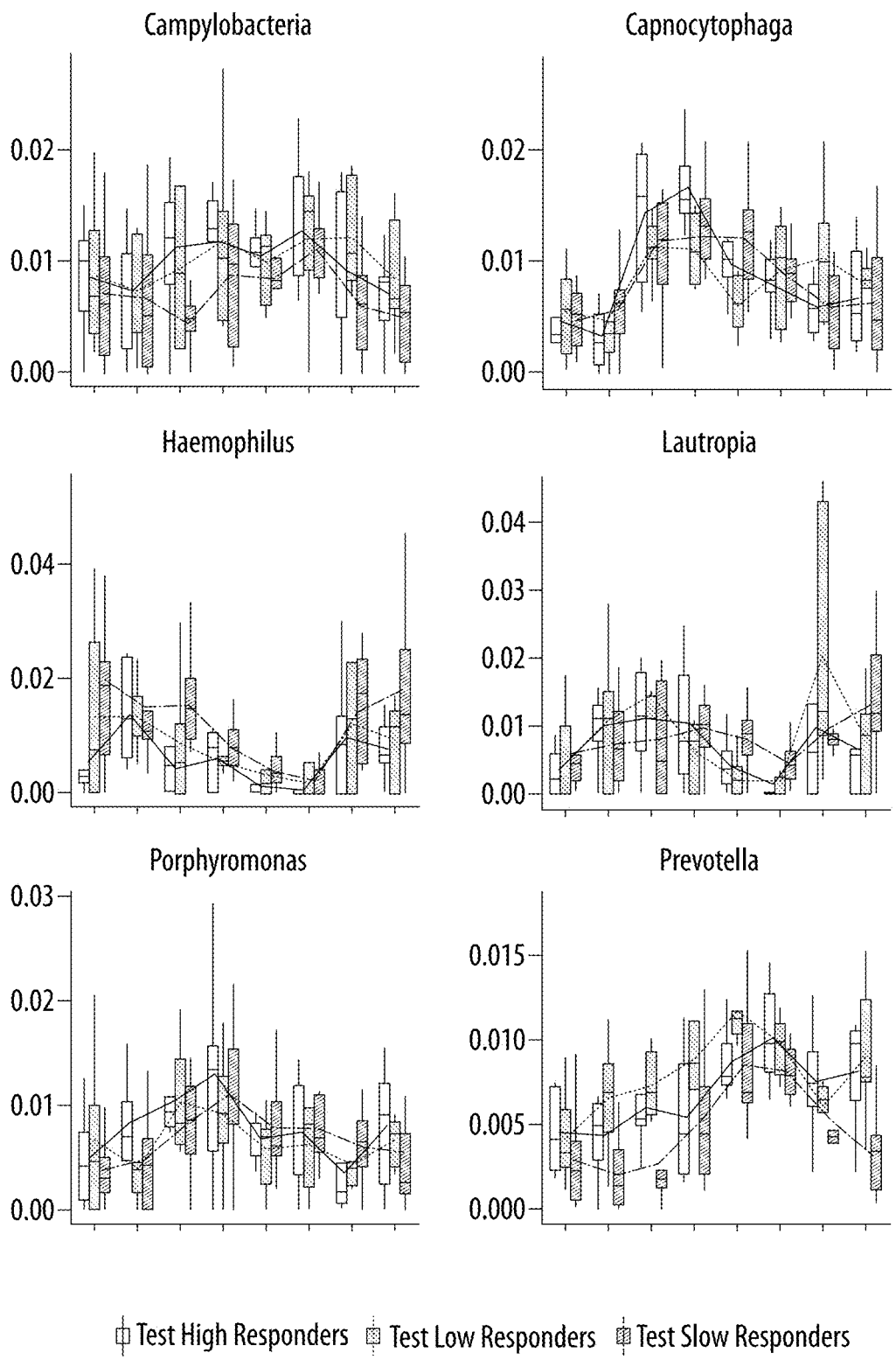
Figure 9:
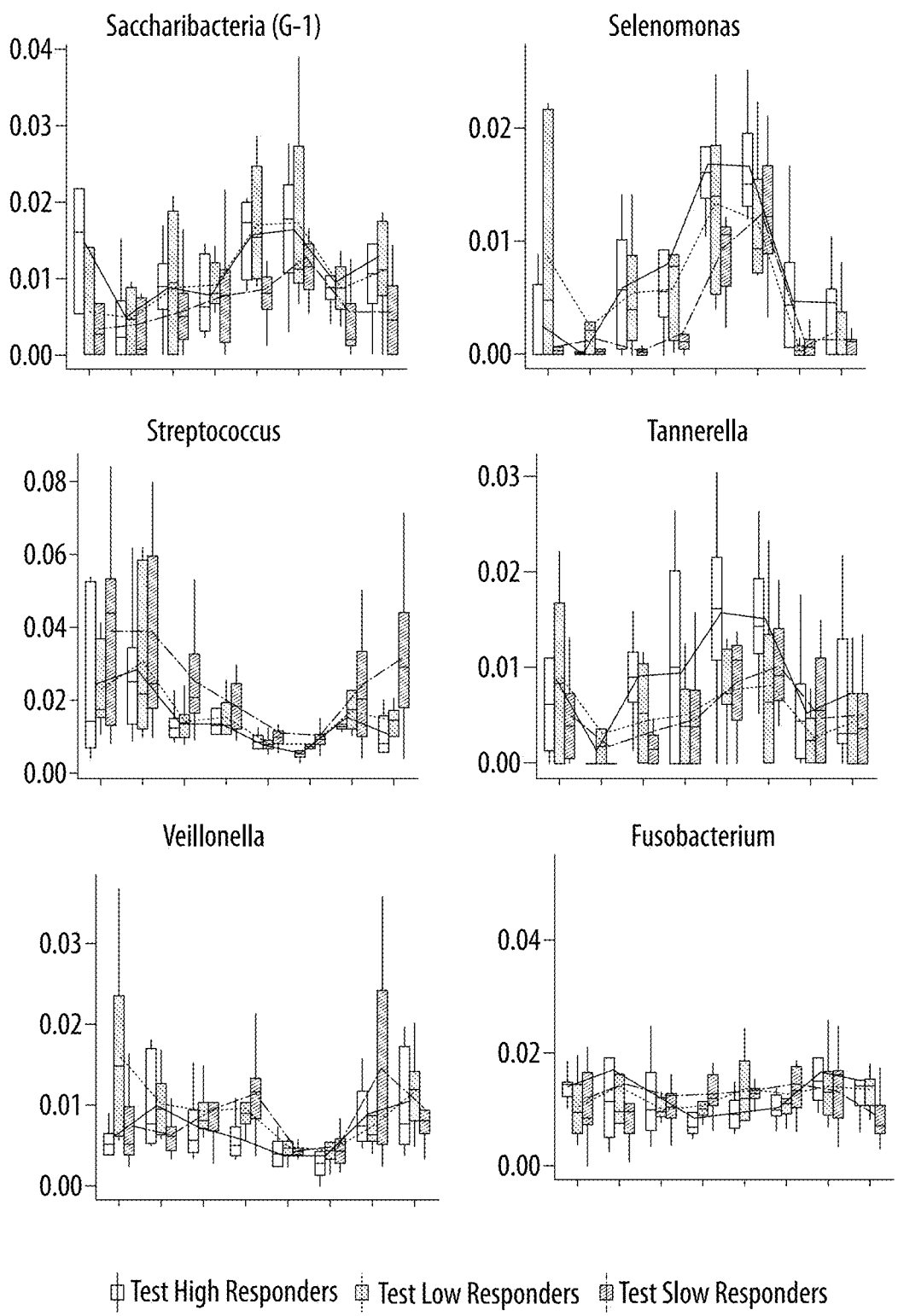
Figure 9:
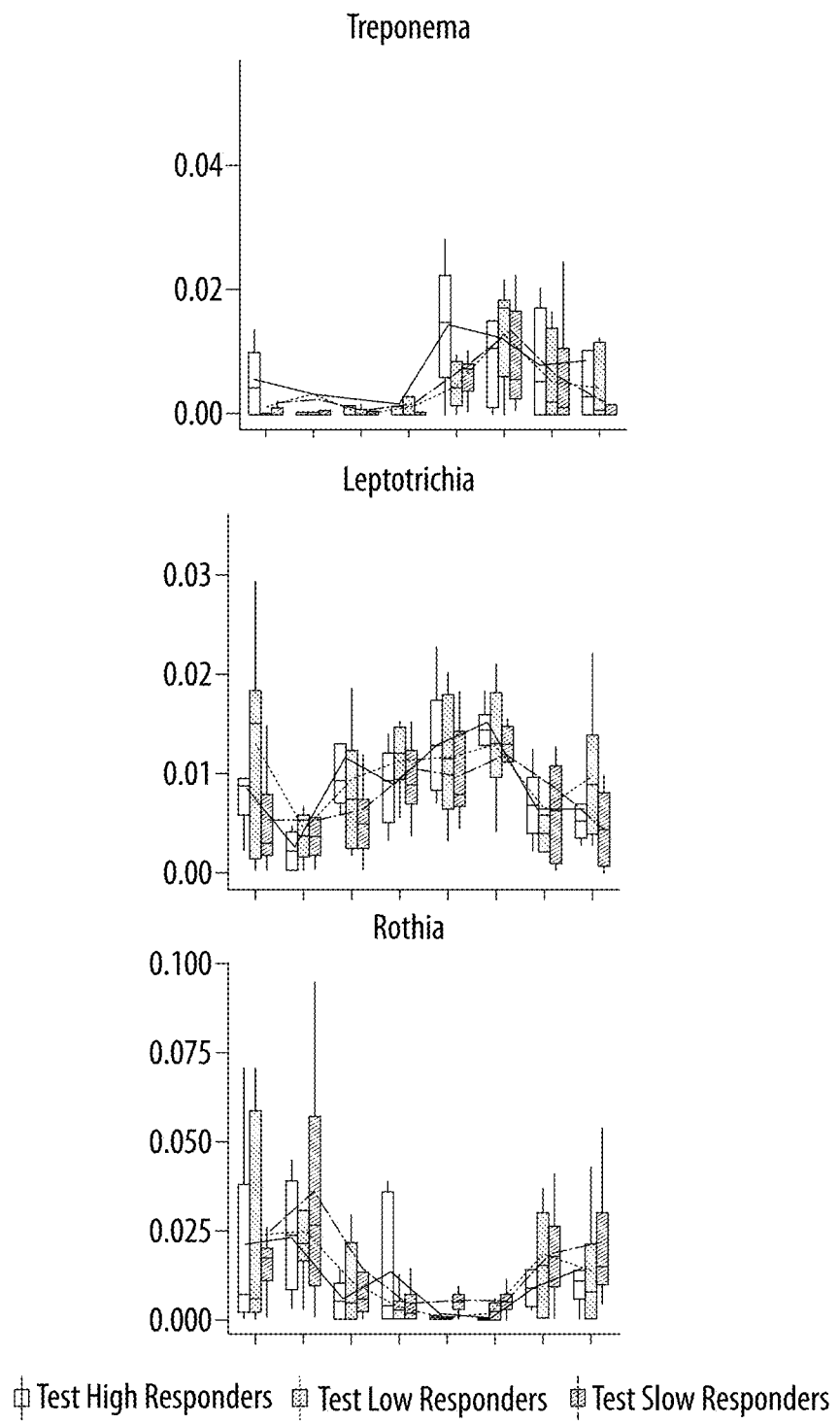

For statistical analyses at the genus level (FIG. 9) normalized abundances of amplicon sequence variants (ASV's) were agglomerated using a novel mean agglomeration strategy to the genus level from Day −14 to Day 35 by responder group: High, Low, and Slow (n=293 samples from 21 subjects). Boxplots show mean and lower/upper quartiles of transformed data using a pseudo count (10−6) and % mean agglomerated abundance of ASV's at the genus level; whiskers show inner fences; grey dots represent outliers. Lines represent the linear regression (Loess) for each respective responder group, High, Low, and Slow, from Day −14 to Day 35. This mean agglomeration approach using the ASV abundances aims to offer better resolution of agglomerated abundance data at various taxonomic levels by taking into account the number of unique ASV's at that respective taxonomic level in an attempt to reduce signals that may result in an over estimation taxonomy in a sample, individual, and or group.

Results

Variation in the Clinical Response to Human Experimental Gingivitis

Figure 1B:
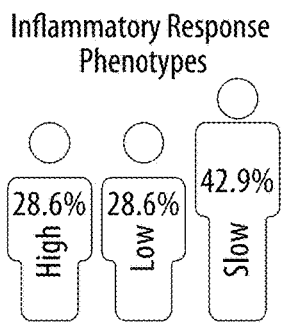
Figure 6A:
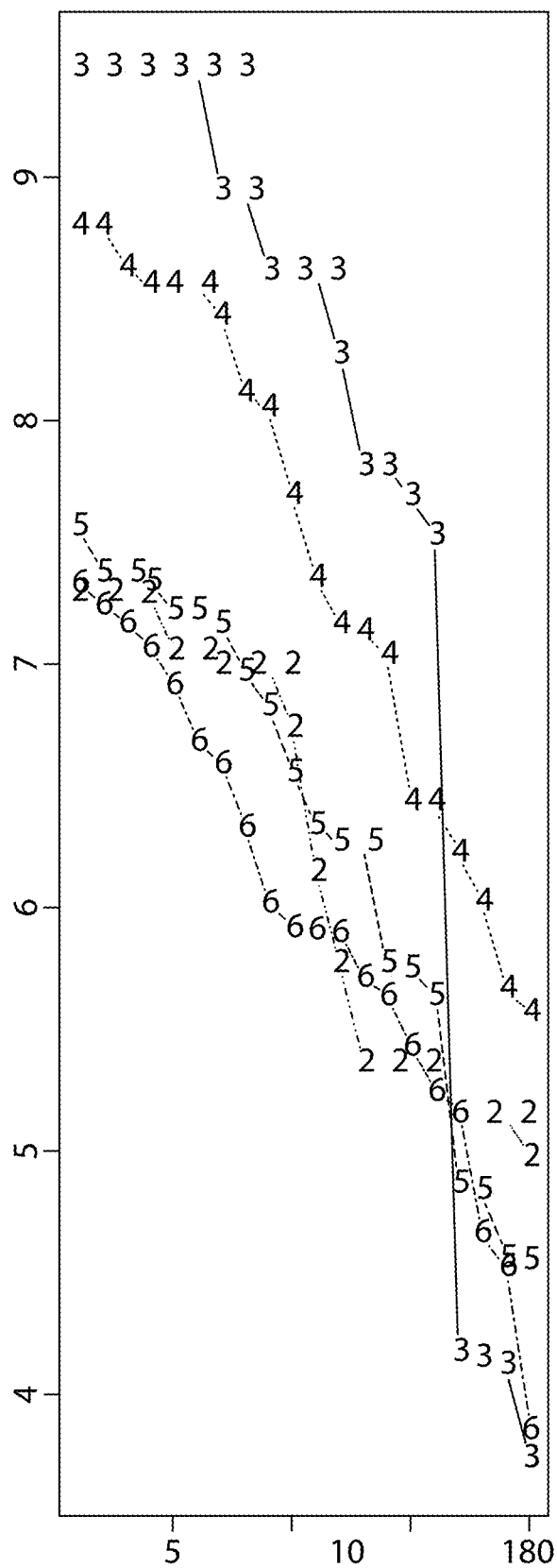
Figure 6E:
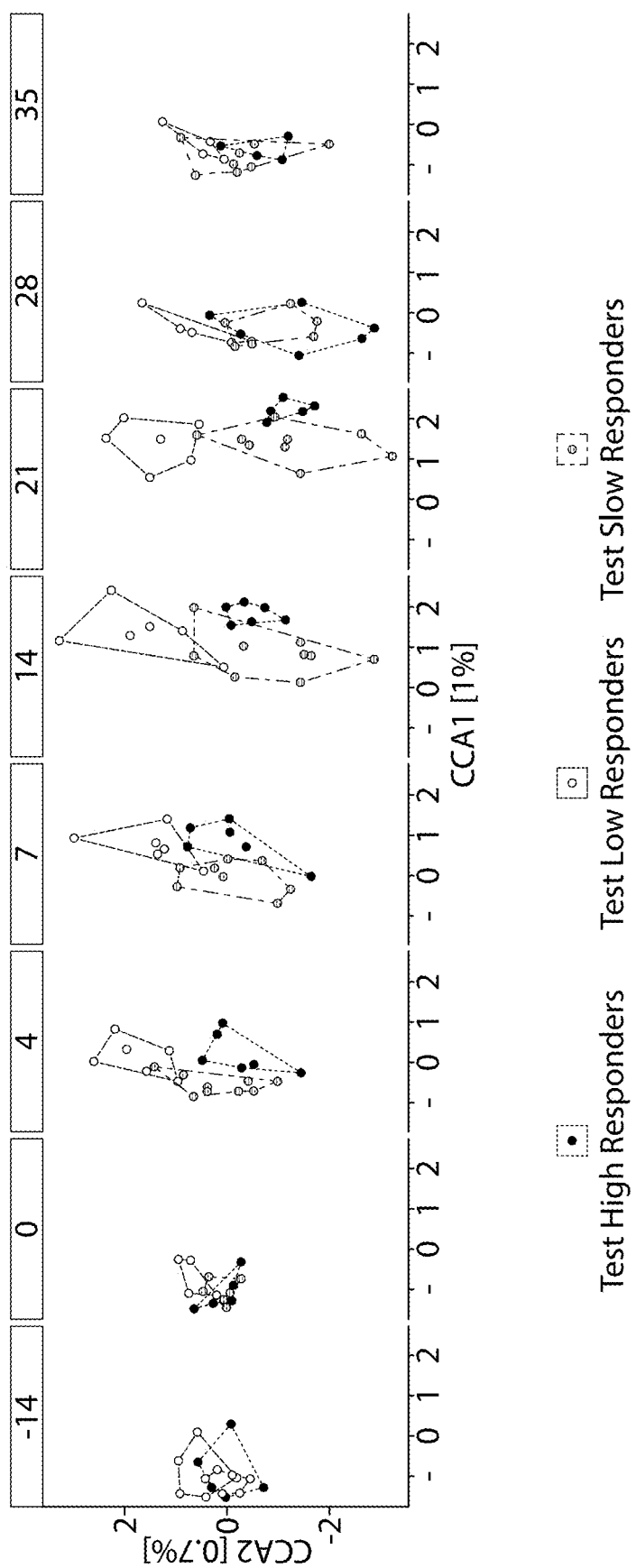
Figure 7D:
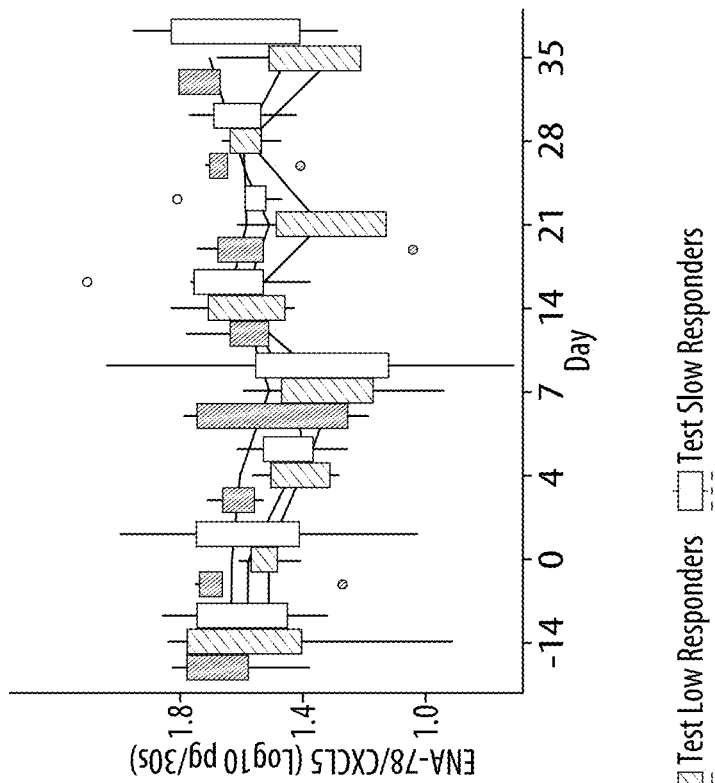
Figure 7C:
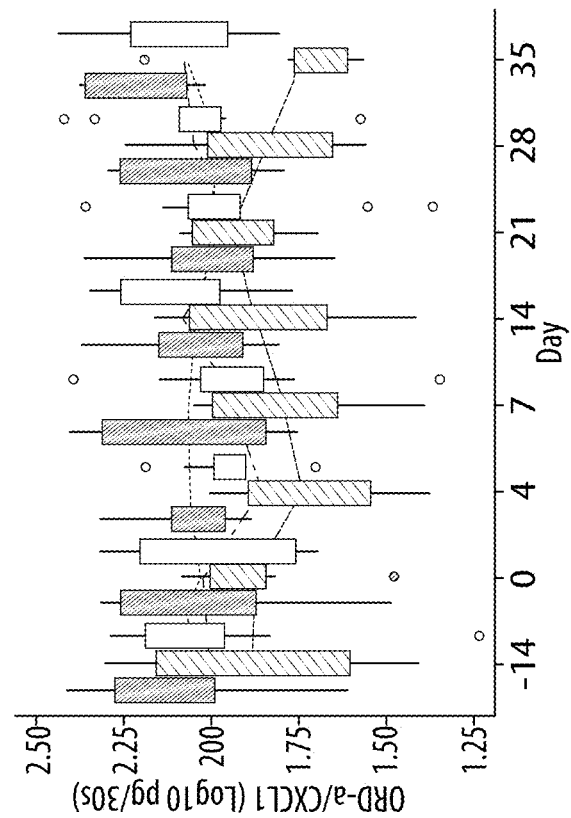
Figures 7E, 7F:
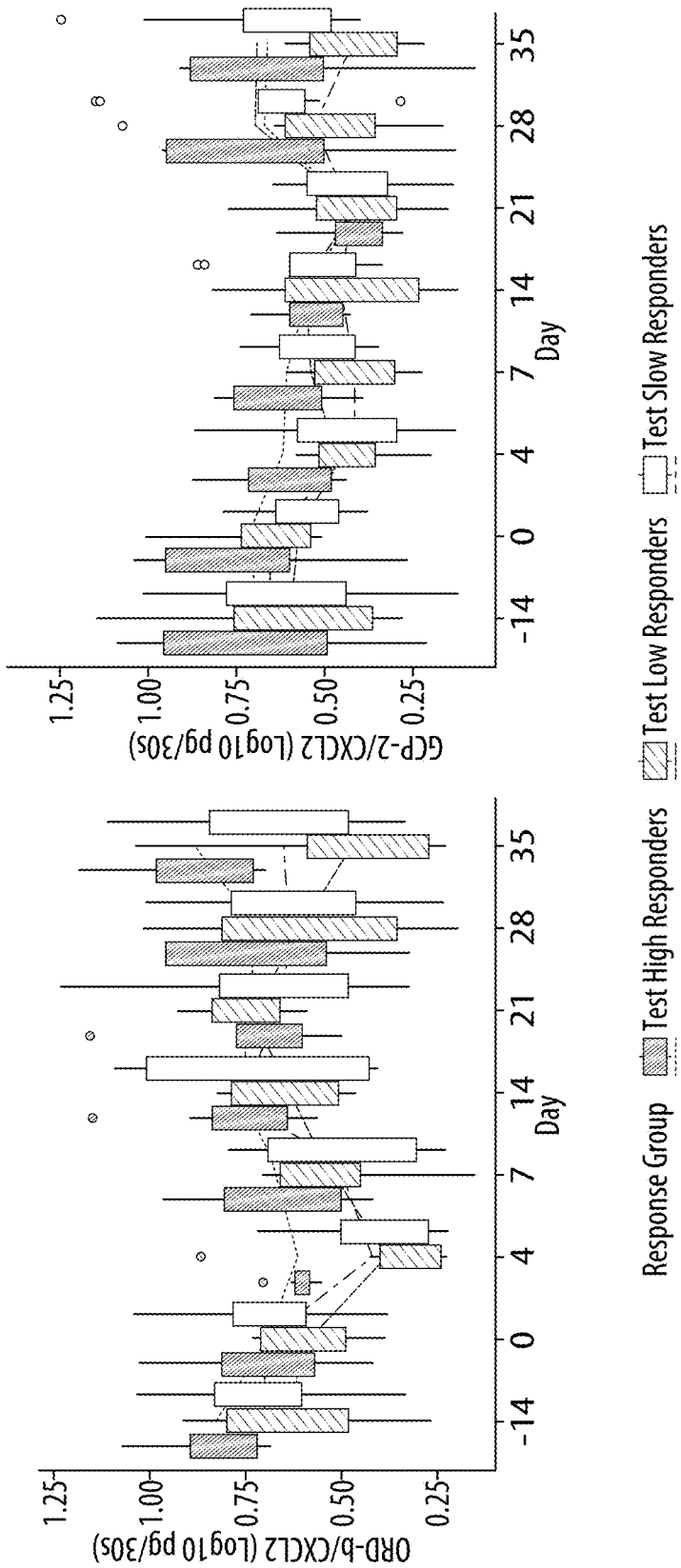
Figure 8A:
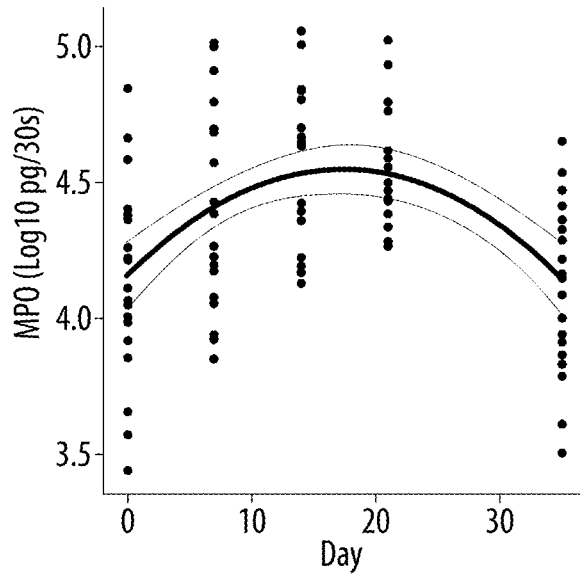
FIGS. 8A-8D contain data showing temporal associations between neutrophil chemokines (MIF, IL-8) and neutrophil numbers (MPO levels). Regression lines arise from quadratic regressions of MIF, IL-8, MPO and bacterial load against time. Statistically significant differences are reported for the second-degree polynomial terms and the regression coefficients are reported to demonstrate the direction of the U-shaped distributions over time.
Figure 8B:
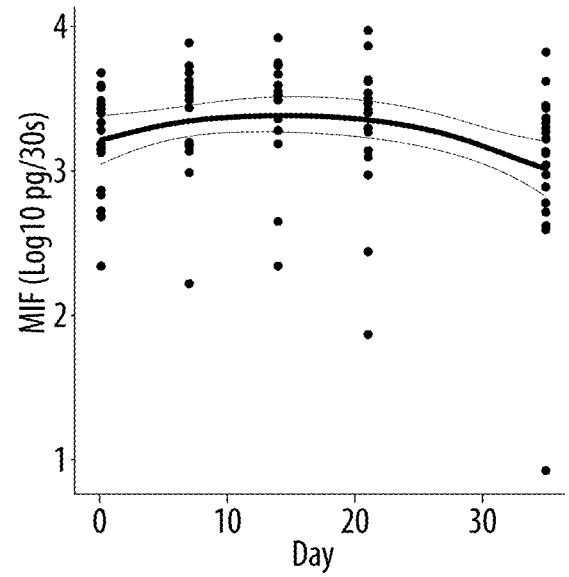
Figure 8C:
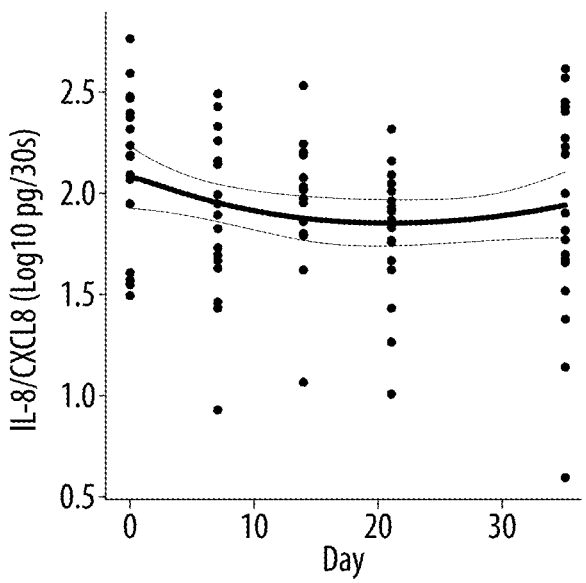
Figure 8D:
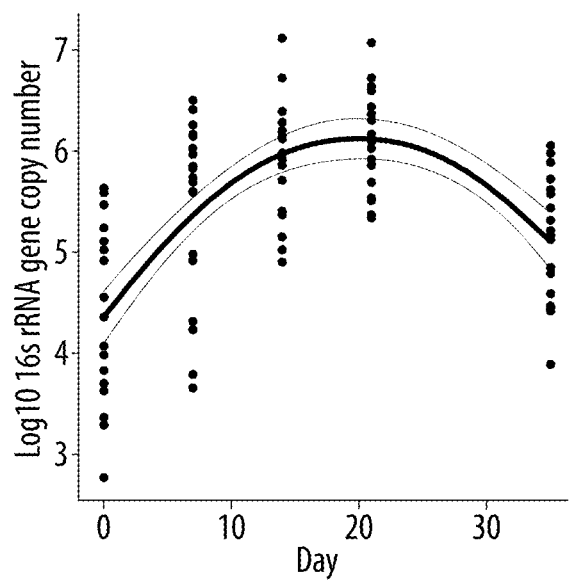

In order to more fully explore the variation in the human host response to experimental gingivitis, an experimental design that incorporated both early and late clinical evaluation and sampling time points was employed (FIG. 1A). Clinical evaluation employed the standard measures of gingivitis which are the gingival index (GI) and bleeding upon probing (BOP), which measure of gingival inflammation as well as the plaque index (PI), which measures bacterial accumulation on the tooth surface. Consistent with the observations in numerous previous analyses, dental plaque accumulation and clinical gingival inflammation was revealed in all study subjects (FIGS. 2A-2D). As previously described, there were significant variations in the clinical response to gingivitis revealed both high and low clinical response groups. The inclusion of multiple early and late clinical evaluation measurements facilitated the identification of a novel slow host response. These participants were characterized by a delayed increase in microbial plaque accumulation (PI) as determined by quantification of 16S RNA gene copy numbers as well as a corresponding delay in clinical inflammatory indices (FIGS. 2E-2I). In order to further understand the variability in the data trajectories of gingivitis severity represented by GI and BOP in on their test sides between Day 0 and Day 21, clustering analysis was performed using the k-means for longitudinal data method in the "kml3d" R package (FIGS. 6A-6D). This analysis revealed three distinct clinical response groups that were then designated as either high, low, or slow and represented 28.6, 28.6, and 42.9% respectively of the study participants (FIG. 1B, FIG. 6F and Table 1). The high responder group included at a total of 6 participants (3 male, 3 female, mean age: 20.67±0.82 years), the low responder group also included a total of 6 participants (4 male, 2 female, mean age: 24.5±5.47 years) and the slow responder group included 9 participants (4 male, 5 female, mean age 24.33±4.61). There were no statistical significant differences between the three groups in age (F(2, 18)=1.668, p=0.216) or gender ($\chi 2$=0.73182, p=0.6936).

TABLE 1

| Participant demographics | High responder group (N = 6) | Low responder group (N = 6) | Slow responder group (N = 9) |
|---|---|---|---|
| Age (years) | | | |
| Mean ± SD | 20.67 ± 0.82 | 24.5 ± 5.47 | 24.33 ± 4.61 |
| Difference (One-way ANOVA) | F(2,8) = 1.668, p-val = 0.22 | | |
| Gender | | | |
| Male | 3 | 4 | 4 |
| Female | 3 | 2 | 5 |
| Difference (Chi-square test) | $X^2$ = 0.73182, df = 2, p-val = 0.69 | | |

Figures 2E, 2F:
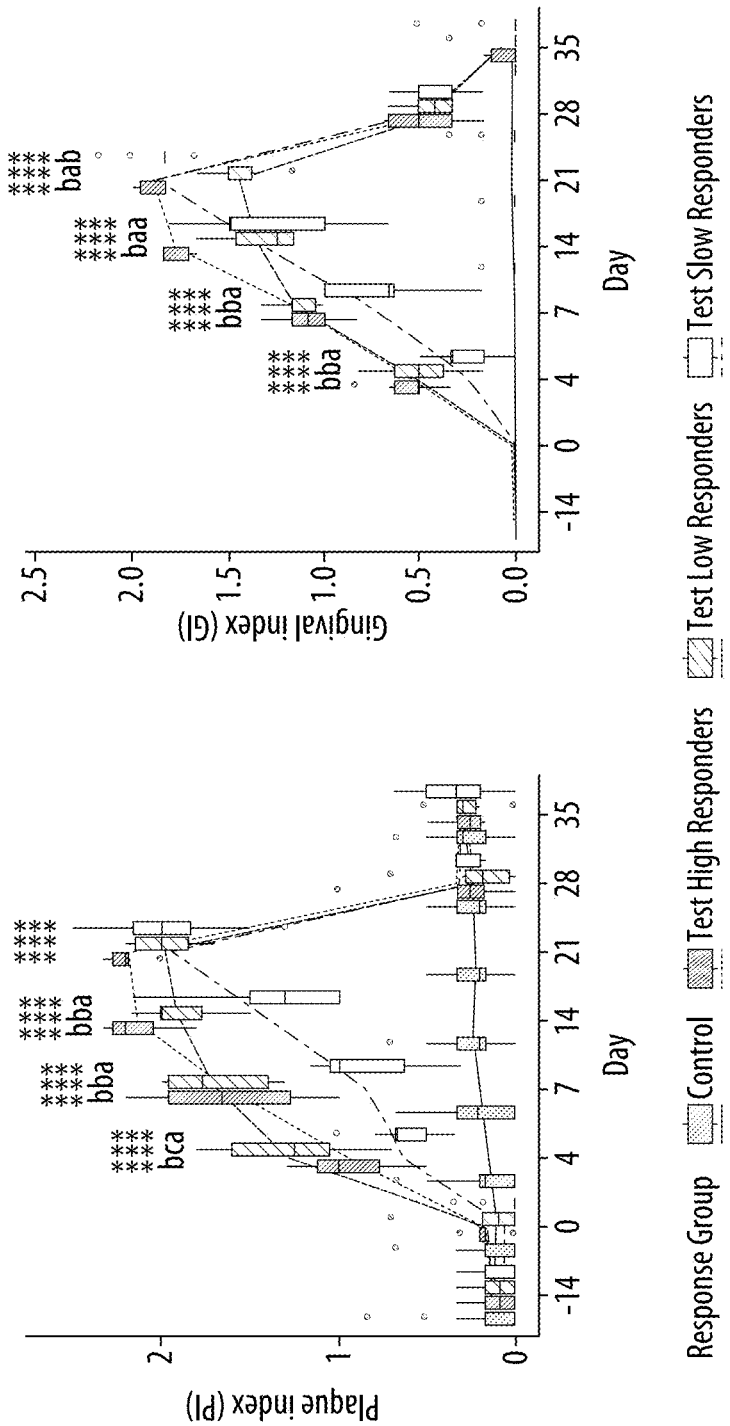
Figure 2H:
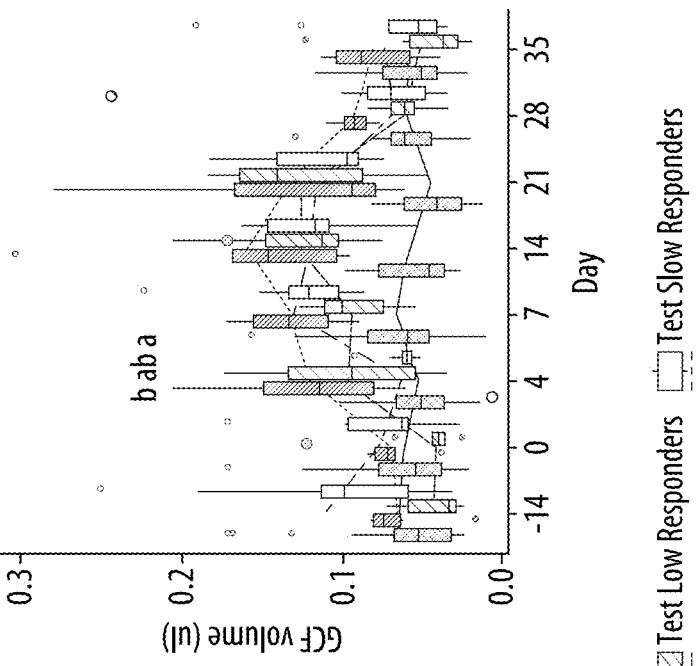
Figure 2G:
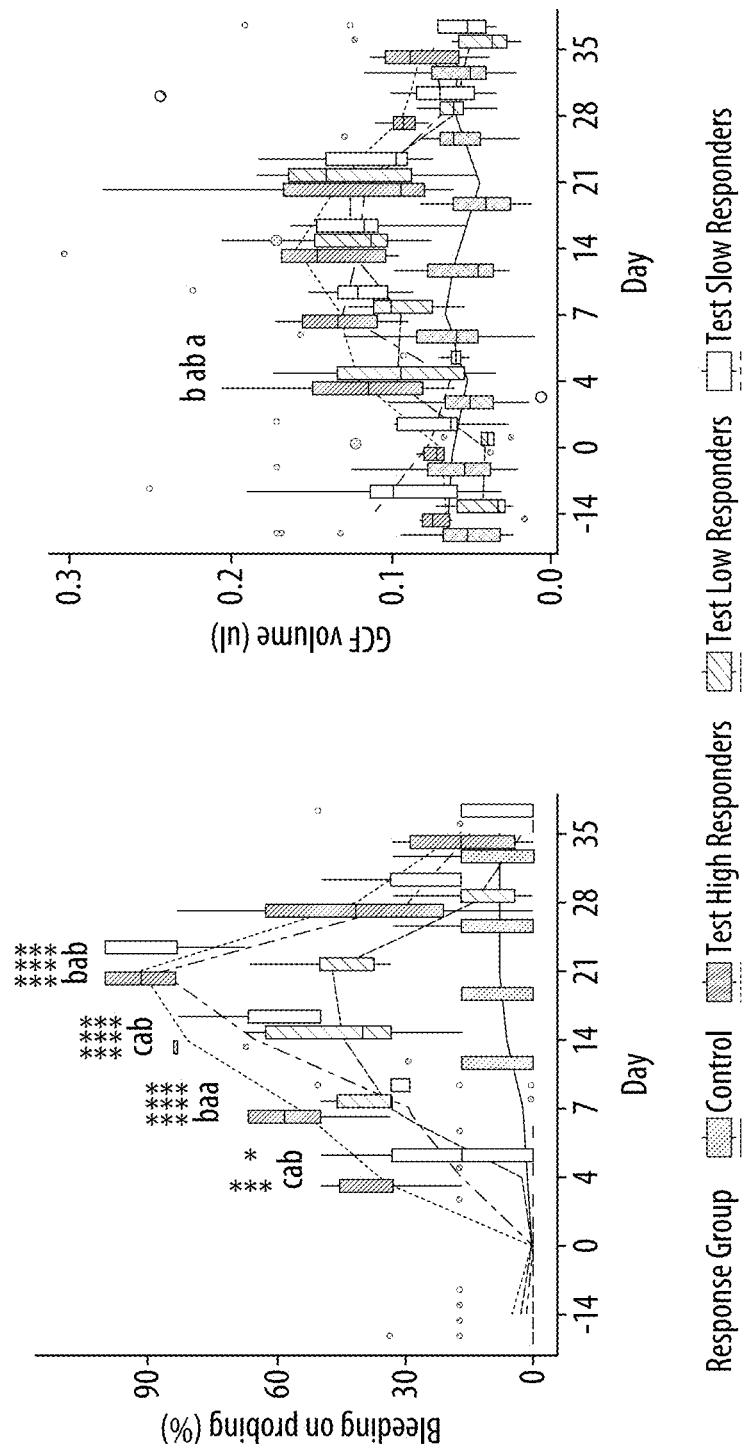
Figures 2K, 2L:
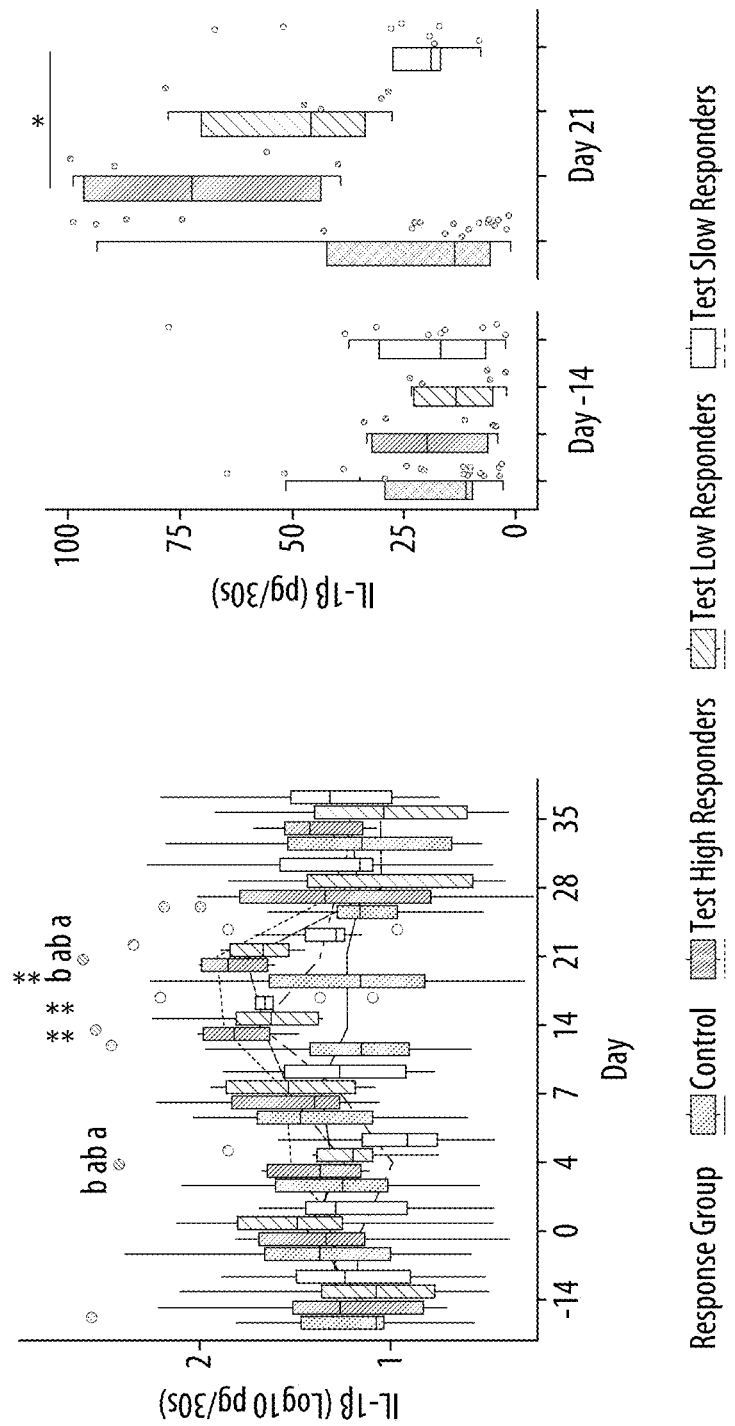

Statistical differences in the trajectories of clinical parameters (PI, GI, BOP) from both baseline (Day 0) and between the groups were evident (FIGS. 2E-2G). However, there was no significant difference between groups with respect to gingival crevicular fluid (GCF) volume (FIG. 2H) or neutrophil migration into the gingival crevice as determined by quantitative ELISA determination GCF myeloperoxidase (MPO) concentrations (FIG. 2J). In contrast to the similar neutrophil migration responses observed in the three groups, only the high response group displayed a significant increase in IL-1β levels at the end of the induction period (Day 21) where clinical inflammation was the greatest (FIG. 2K and FIG. 2L). Notably, at peak inflammation at Day 21, IL-1β levels within the high group is significantly different (p<0.05) than the slow group subjects which are tightly clustered around the baseline (day −14) and control side levels despite displaying similar clinical inflammation (GI and BOP) as the high responder group by day 21 (FIG. 2K and FIG. 2L).

Chemokine Utilization is Significantly Altered During Experimental Gingivitis

Figure 3A:
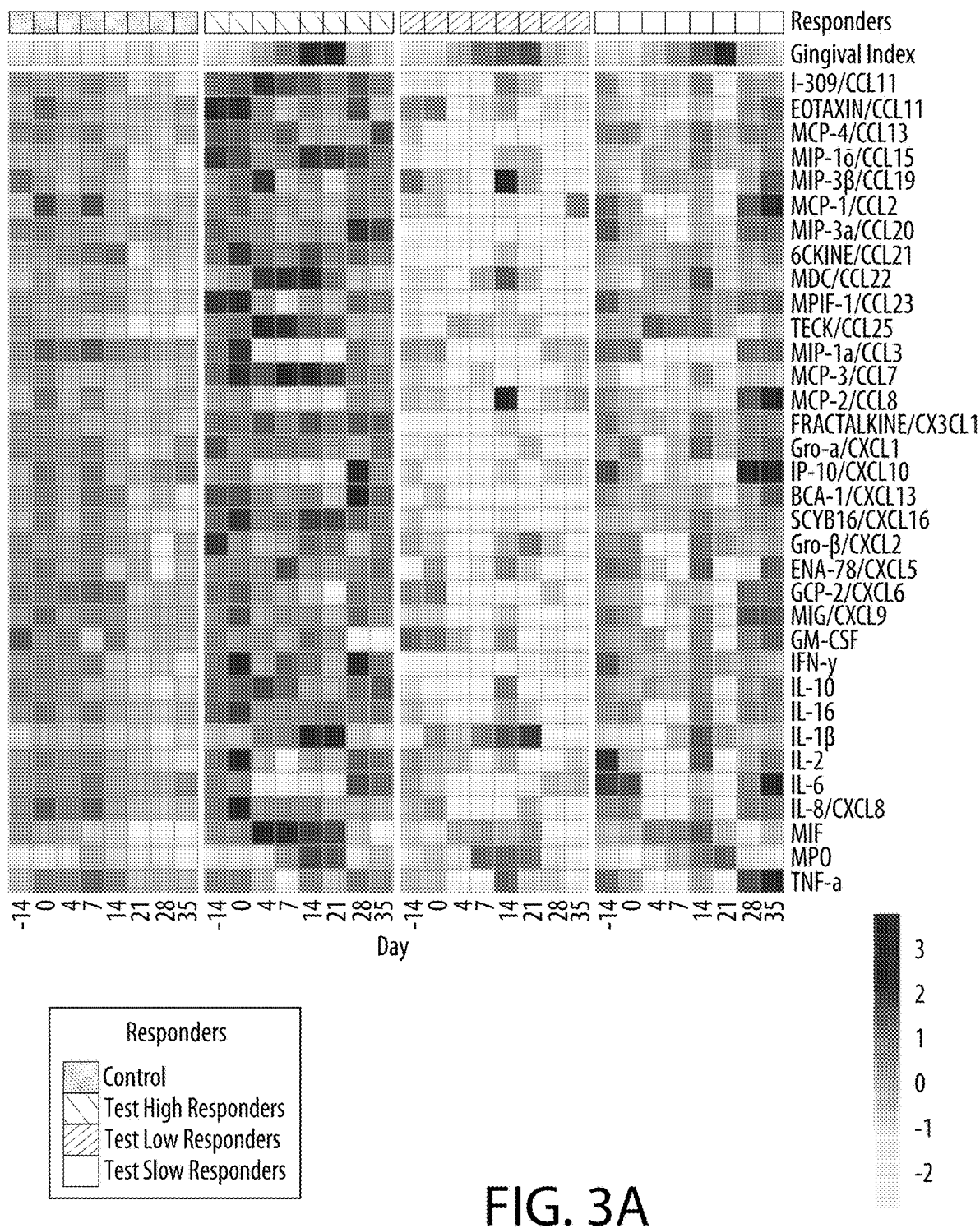
FIGS. 3A-3H contain data showing the relationship between chemokine levels and the three clinical response groups.

Differences in the host inflammatory mediator response between the three different clinical responder groups was performed with a bead based multiplex analysis (Bio-Plex Pro™ Human 40-plex Chemokine Panel). FIG. 3A displays the normalized (row wise Z-score) log mean values for the expressed chemokines (pg per 30-s sample) in each responder group as well as the control teeth (all responder groups combined for control teeth) at the indicated day. Comprehensive analysis of host inflammatory mediators elicited by the different clinical 165 responder groups revealed significant changes in overall chemokine expression patterns. Most notably, it was found that the low clinical responder group displayed several standard deviations below the mean of all the groups in most chemokines. This is consistent with these individuals demonstrating the lowest levels of clinical inflammation throughout this experimental gingivitis study (FIGS. 2E-2G).

Figure 3B:
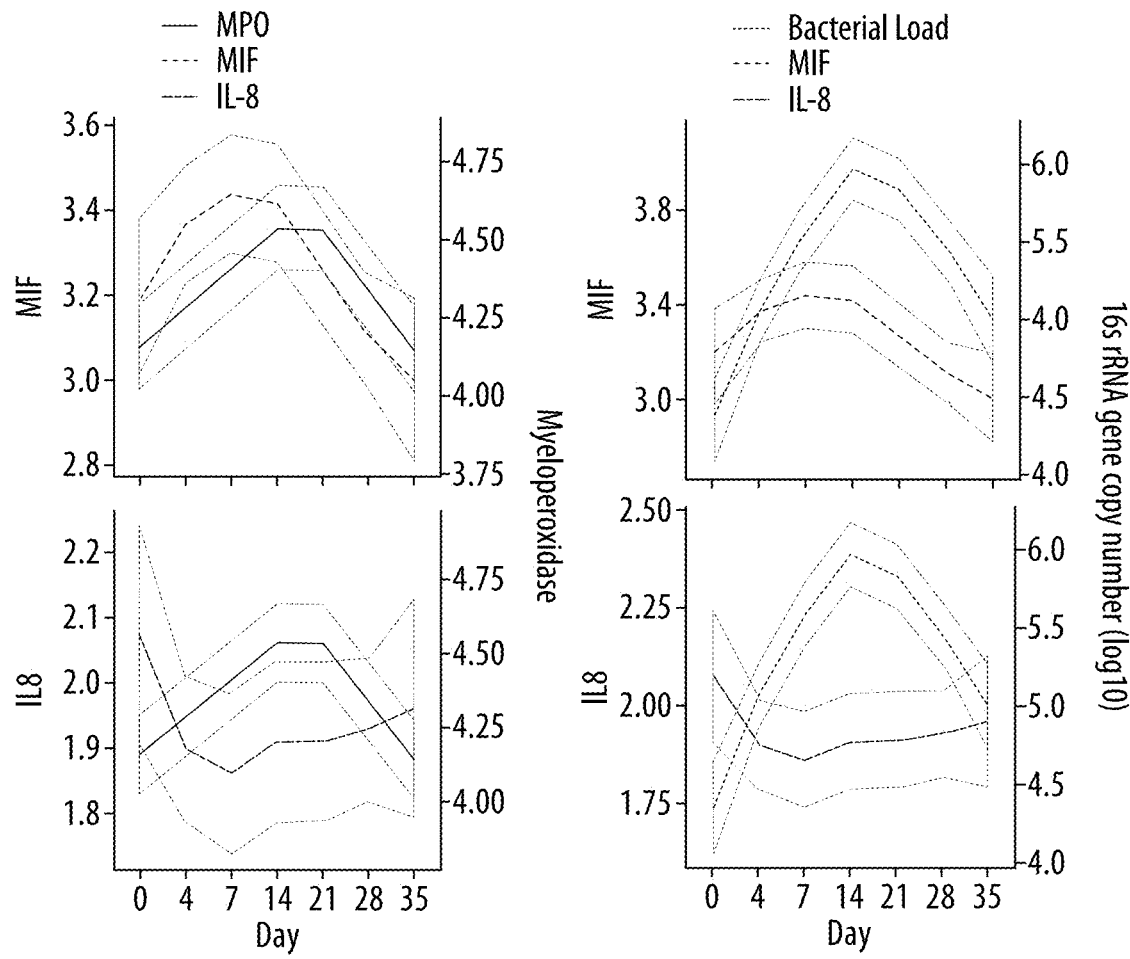
Figure 3C:
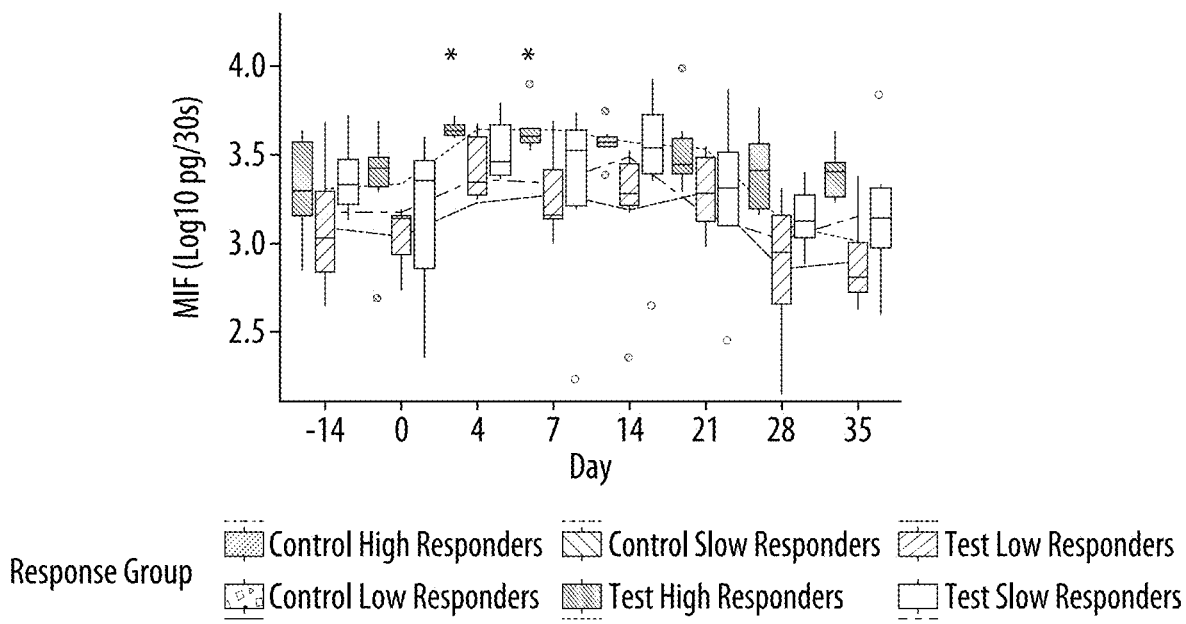
Figure 3D:
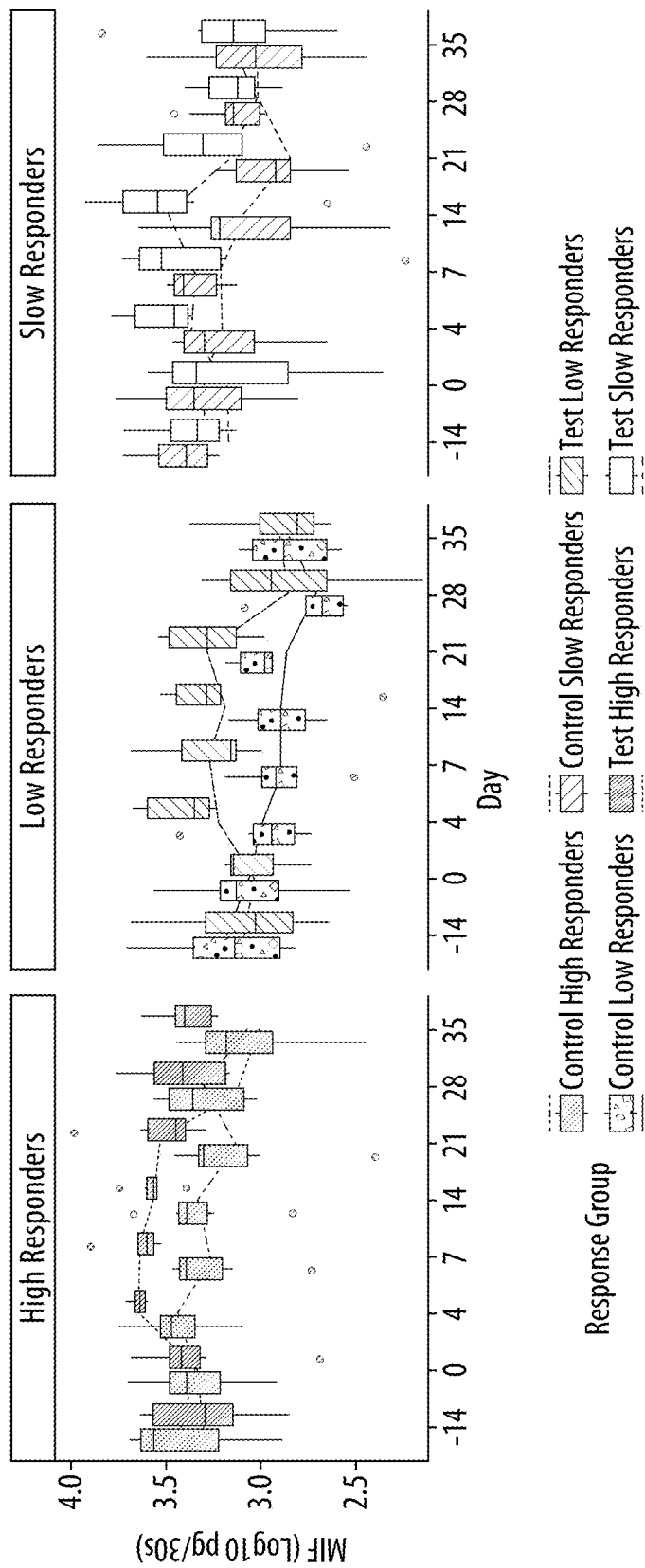
Figure 3F:
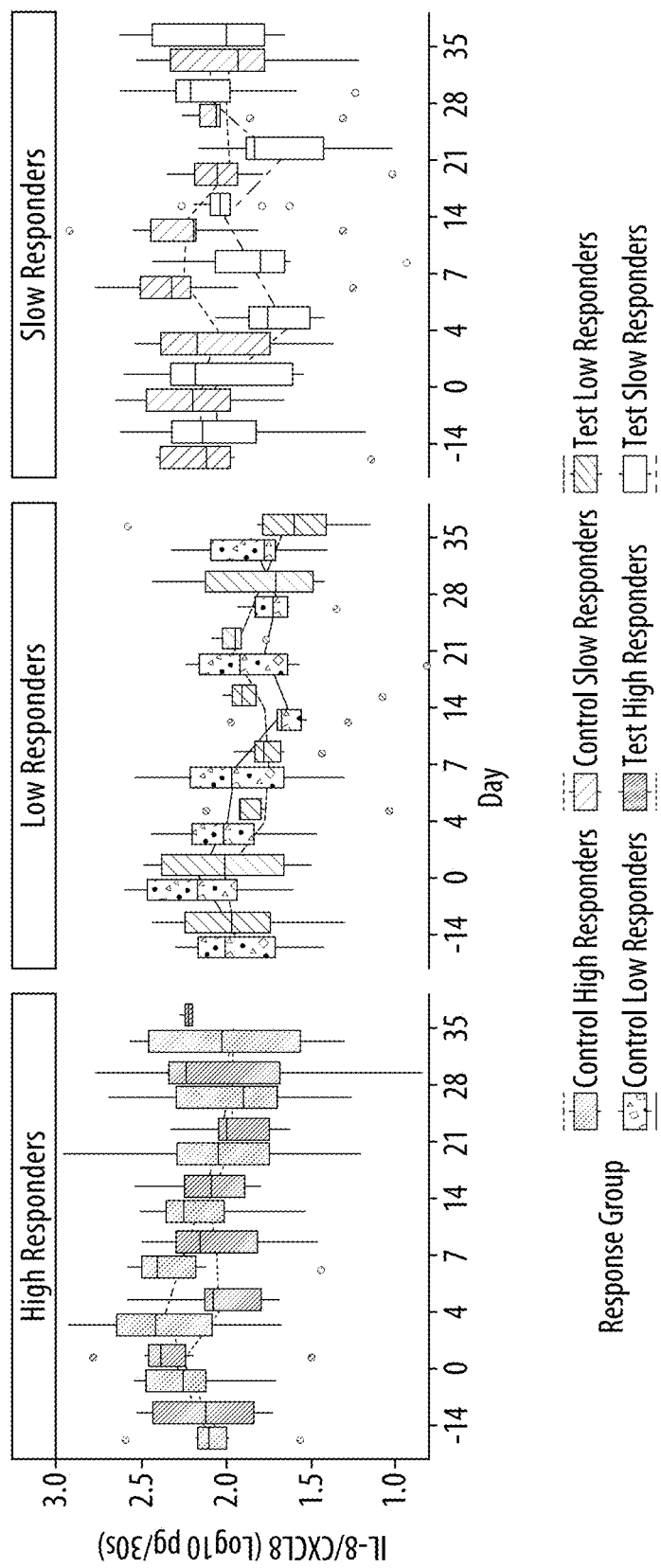
Figure 3E:
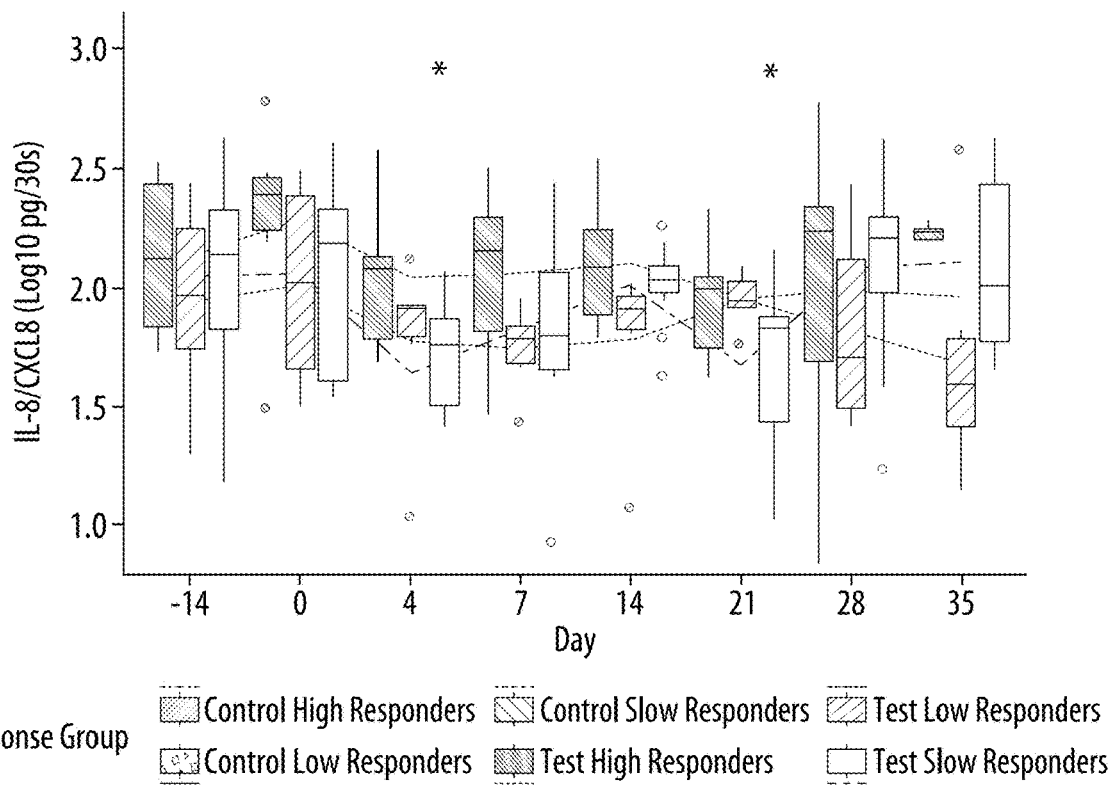
Figure 3G:
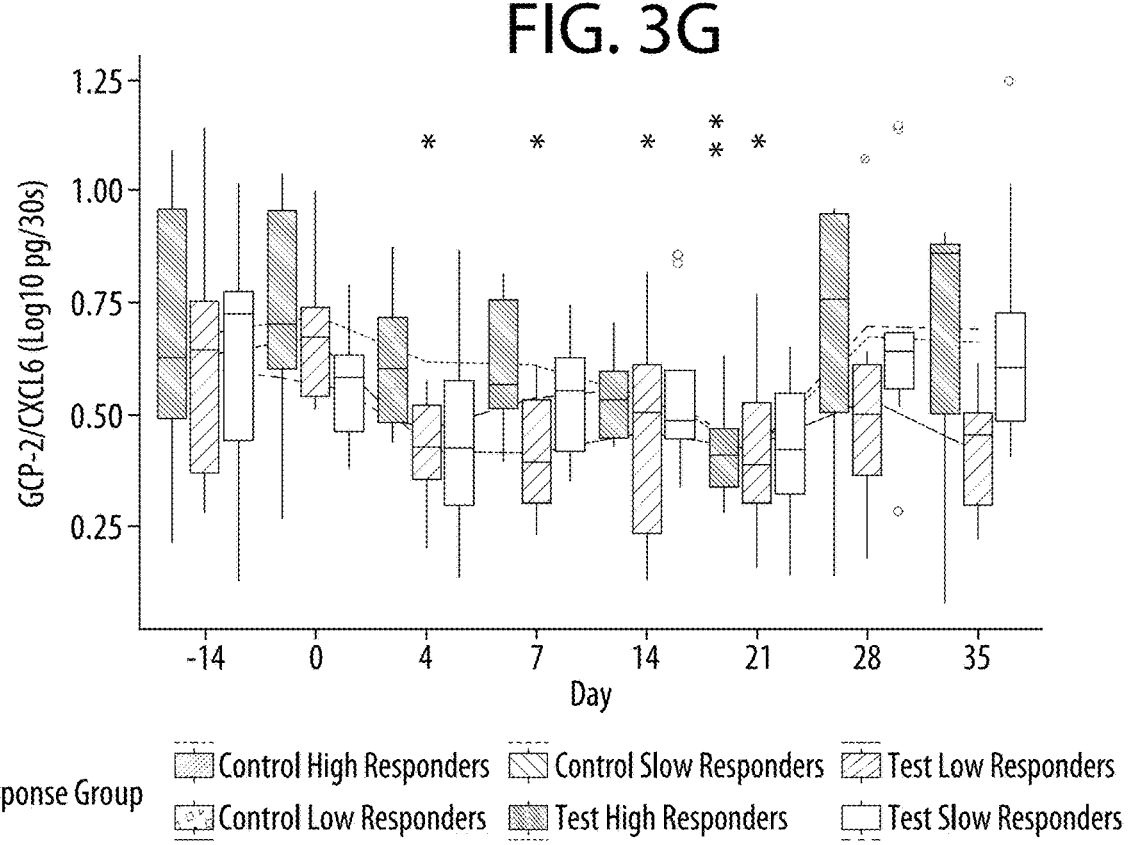
Figure 3H:
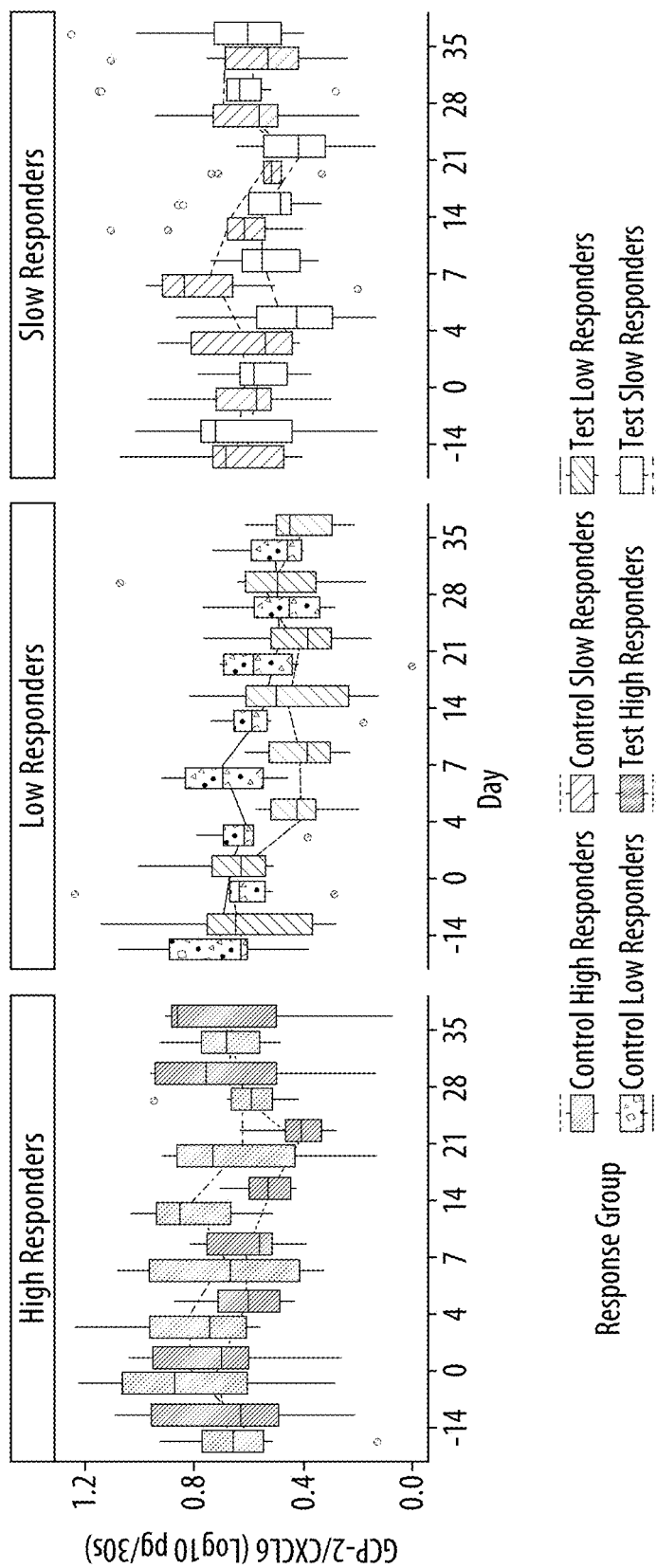
Figure 4B:
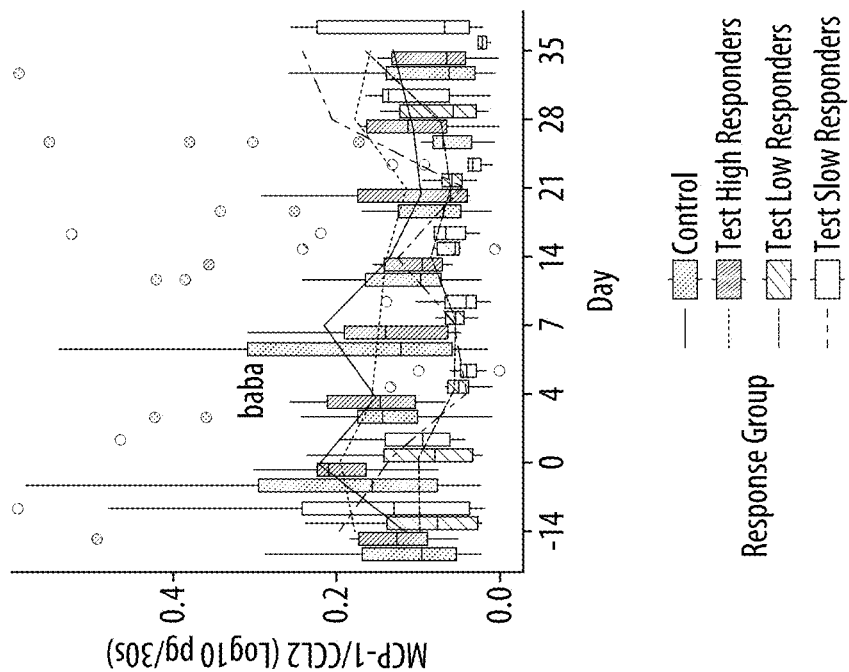
Figure 4A:
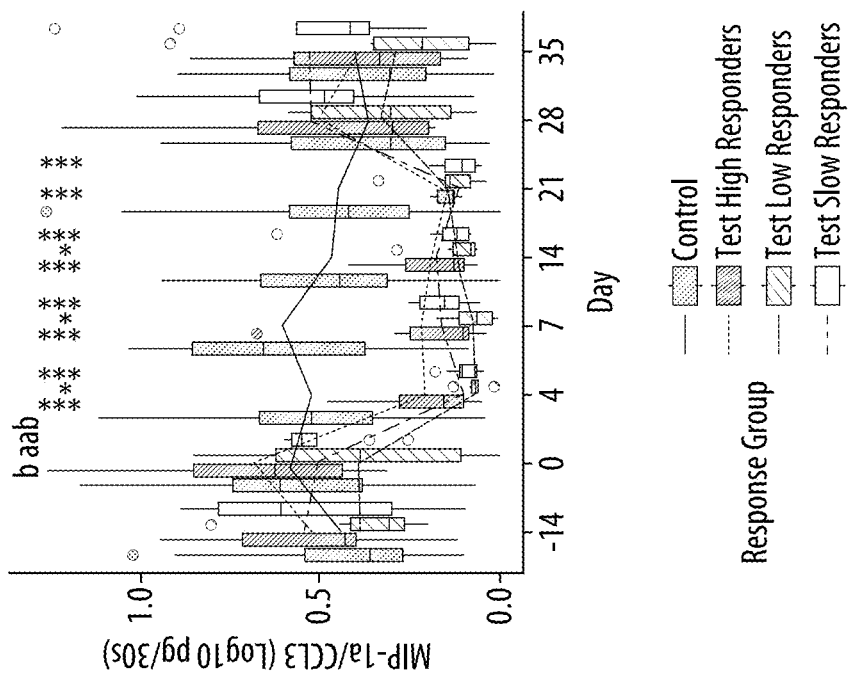

Upon more detailed examination, the levels of the major neutrophil chemokines observed on the panel revealed nearly all neutrophil chemokines examined in this study either decreased or did not significantly increase during experimental gingivitis (FIG. 3A and FIGS. 7A-7F). Of particular note is the observation that IL-8/CXCL8 and GCP-2/CXCL6 (FIGS. 3E-3H), two chemotactic and neutrophil activating chemokines did not increase during experimental gingivitis, which is consistent with the reported difference in the neutrophil phenotypes found in gingivitis. In contrast to the decreases found in neutrophil chemokine expression, macrophage inhibition factor (MIF), which has been reported to demonstrate neutrophil chemotactic activity, trended towards increased expression in all clinical response groups and was significantly increased compared to baseline values (Day 0) in the high response group on day 4 and 7 (FIG. 3C and FIG. 3D). In fact, granular analysis of early gingival inflammation (Days 0-4) groups revealed that neutrophil migration into the gingival sulcus changed in response to MIF and not IL-8/CXCL8 levels over time (FIG. 3B). Since, the experimental induction and resolution interventions led to an inverted-U shape and the increase in MIF and neutrophil migration (p <0.0001) as well as the decrease in IL-8/CXCL-8 (p<0.0001) occurred in all clinical response groups (FIGS. 3A-3F) the analyses was performed with quadratic regression models combining all the clinical response groups. The time course distributions of MIF and MPO mirrored one another with changes in MIF level preceding concordant MPO levels (FIG. 3B). The temporal changes in bacterial load, MPO and MIF had very similar patterns across induction and resolution timepoints, while IL-8/CXCL-8 levels did not significantly change (p=0.09) (FIGS. 8A-8D). Neutrophil chemotaxis mediators altered during experimental gingivitis may provide the mechanism for previously described oral PMN activation states are reduced in gingivitis. Bone and tissue chemokine modulators are significantly altered during experimental gingivitis The lack of a strong host chemokine response among individuals within the low inflammatory response group was further investigated (FIGS. 4A-4F). This analysis revealed that MIP-1α/CCL3 (macrophage inflammatory protein-1α), a homeostatic regulator of bone resorption and a proposed biomarker of periodontitis, was significantly reduced in all three clinical response groups at the first gingivitis measurement (Day 4) and was restored at the first time point in the resolution phase (Day 28) (FIG. 4A). A novel MIP-1α/CCL3 mediated potential bone protection mechanism was identified. As shown in FIG. 4A, there is a significant and rapid decrease in MIP-1α/CCL3, a chemokine involved in inducing osteoclastogenesis while the control side does not display a significant decrease in MIP-1α/CCL3. MIP-1α/CCL3 is a cytokine belonging to the CC chemokine family that is involved in the acute inflammatory state in the recruitment and activation of polymorphonuclear leukocytes through binding to the receptors CCR1, CCR4 and CCR5. Multiple chemokines are involved in cell migration. MCP-1/CCL2, MIP-1α/CCL3 and GRO-α/CXCL1 are responsible for the mobility of OCPs and the fusion and differentiation of osteoclasts. MIP-1α/CCL3 is a direct stimulator of osteoclastogenesis that is expressed in bone and bone marrow cells by a mechanism that is proposed to be independent of RANK activation. It was found that that five additional chemokines (MCP-1/CCL2, MIP-3α/CCL20, SCYB16/CXCL16, GRO-α/CXCL1, and MPIF-1/CCL23), which have been shown to contribute to either normal bone turnover processes or inflammatory bone loss during periodontitis, displayed overall significantly lower chemokine levels within the low response group when compared to the high response group (FIGS. 4B-4F). A potential MIP-3α/CCL20 mediated disconnect to adaptive immunity in the low response group was identified. FIG. 4C shows that the gingival crevicular fluid levels of the small cytokine CCL20 (Chemokine (C-C motif) ligand 20), which is also referred to as MIP-3α (Macrophage Inflammatory Protein-3), LARC (liver activation regulated chemokine) or 1-309, and which is a chemokine involved in adaptive immune responses, is significantly lower in the low responder group. CCL20 is strongly chemotactic for lymphocytes and weakly attracts neutrophils and is implicated in the formation and function of mucosal lymphoid tissues via chemoattraction of lymphocytes and dendritic cells towards the epithelial cells surrounding these tissues. CCL20 elicits its effects on its target cells by binding and activating the chemokine receptor CCR6. CCL20 is produced by mucosa and skin by activated epithelial cells and attracts Th17 cells to the site of inflammation. It is also produced by Th17 cells themselves. It further attracts activated B cells, memory T cells and immature dendritic cells and has part in migration of these cells in secondary lymphoid organs. Mature dendritic cells down-regulate CCR6 and up-regulate CCR7, which is a receptor for MIP-3β.

Characterization of the Microbial Compositional Changes in the Different Clinical Response Groups.

Figure 5A:
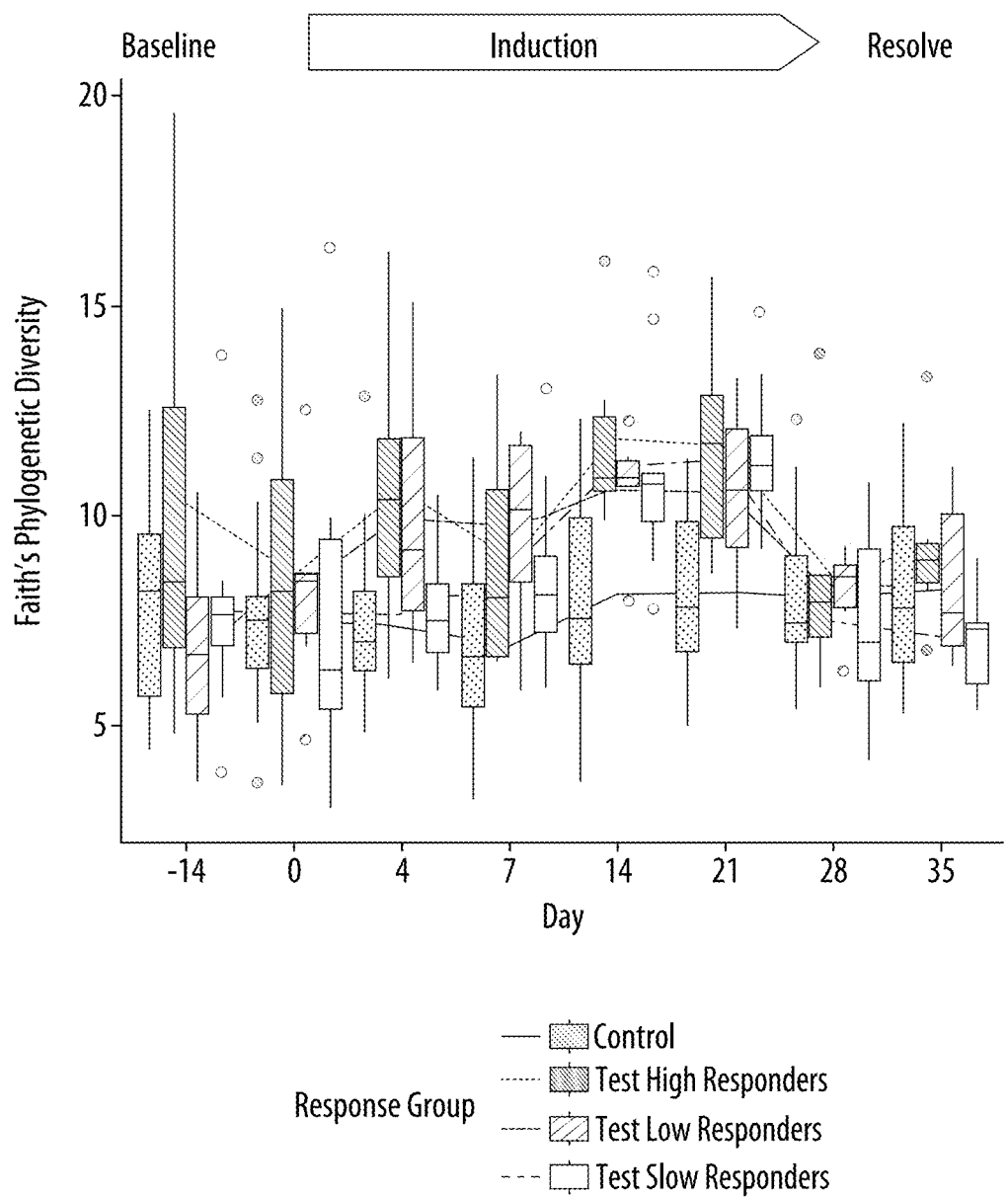
FIGS. 5A-5F contain data showing temporal changes in microbial diversity and taxonomy vary by inflammatory responder type.
Figure 5B:
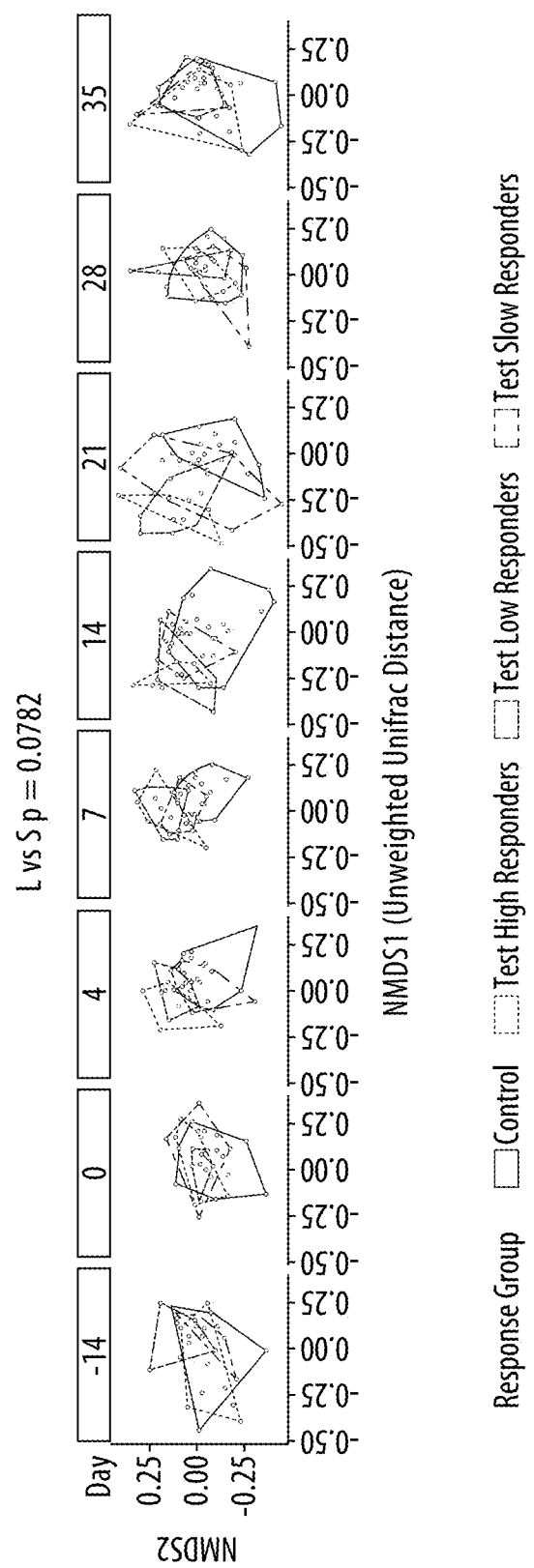

The high-resolution DADA2 approach for 16S rRNA gene data implemented in QIIME2 was used to determine the unique Amplicon Sequence Variants (ASV's) for the dataset (n=11,885 in 334 samples). Changes in the alpha diversity within the microbial community for all subjects' test and control sides (Table 2) as well within each clinical response group (Table 3) during gingivitis induction was examined using five different metrics across different time points. Table 51 contains Alpha diversity indices (mean±SD) during induction and resolution of experimental gingivitis for test and control teeth. Statistically significant difference for test side vs control side, *p<0.05, p<0.01 or *p<0.001. Statistically significant difference for the time trend on the test side; induction phase values vs Day 0, § p<0.05, †p<0.01 or ‡p<0.001. Table S2 contains Alpha diversity indices (mean±SD) during induction and resolution of experimental gingivitis among responder groups. Statistically significant difference for the time trend on for each responder group compared to baseline; induction phase values vs Day 0, *p<0.05, p<0.01 or *p<0.001. At baseline (Day −14 and Day 0), there were no significant differences in any of alpha diversity or beta diversity indices between control and test sides or between the response groups (FIG. 5A and FIG. 5B). This lack of diversity and compositional differences between groups, prior to and after the first cleaning, was not unexpected given that these were all relatively young and healthy subjects with regards to oral health. In general, all alpha diversity metrics using ASV data showed an increase above the control side during the induction phase (Day 0 to Day 21), corresponding to increased gingivitis severity (FIG. 5A, Table 3). Beta diversity analysis revealed shifts in community composition over the same period (FIG. 5B). Together, both alpha and beta diversity showed a return to highly similar compositions after resolution (Day 28 and 35). Notably, as early as Day 4, the slow response group demonstrated a distinct delay in phylogenetic diversity (FIG. 5A) and showed a trend towards separation in beta diversity from the high and low response groups, which remained more similar to the control side (FIG. 5B). This observation was consistent with the rapid accumulation of plaque and development of inflammation in high and low compared to slow responders (FIGS. 2E-2G and FIG. 2I).

Figure 5C:
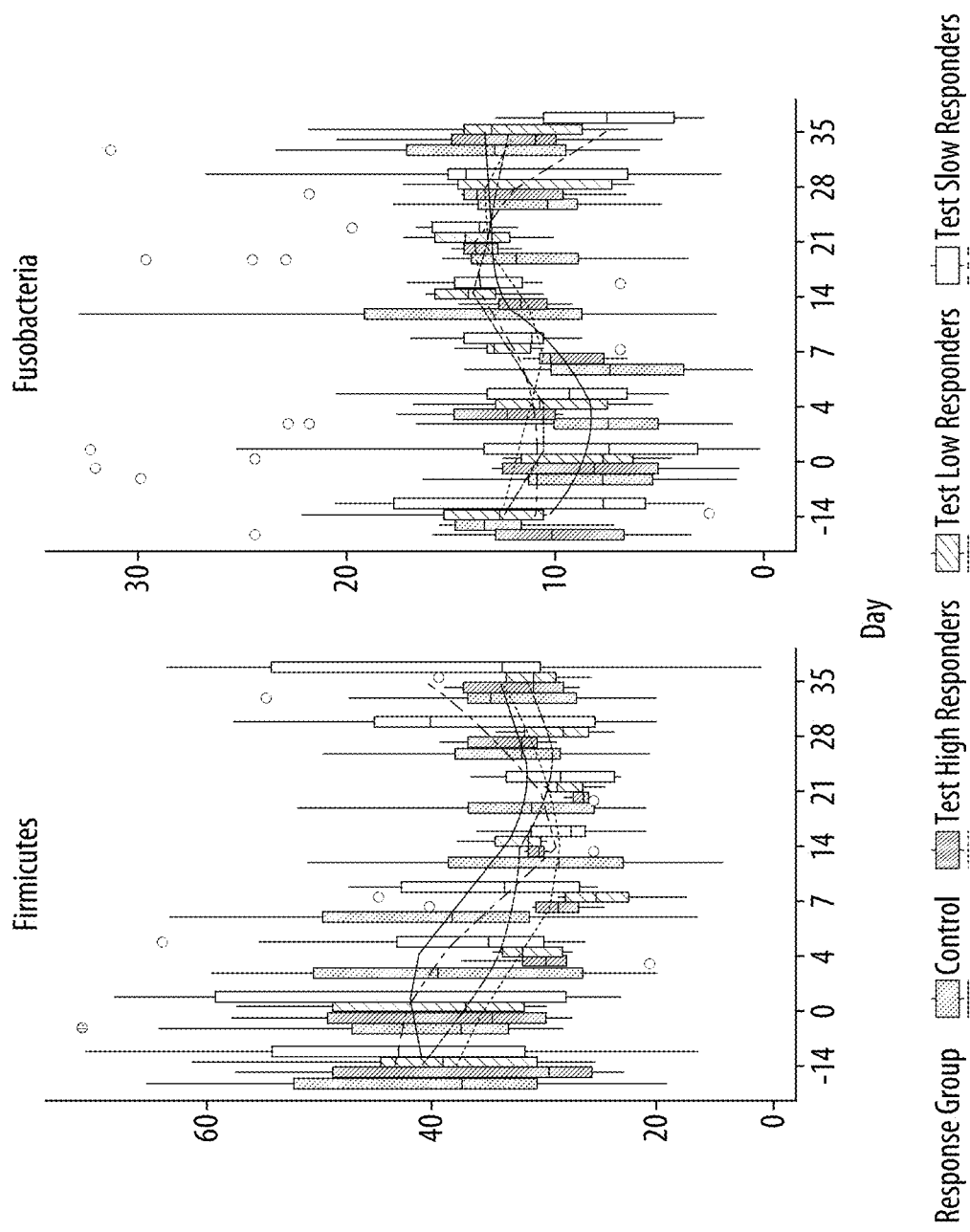
Figure 5D:
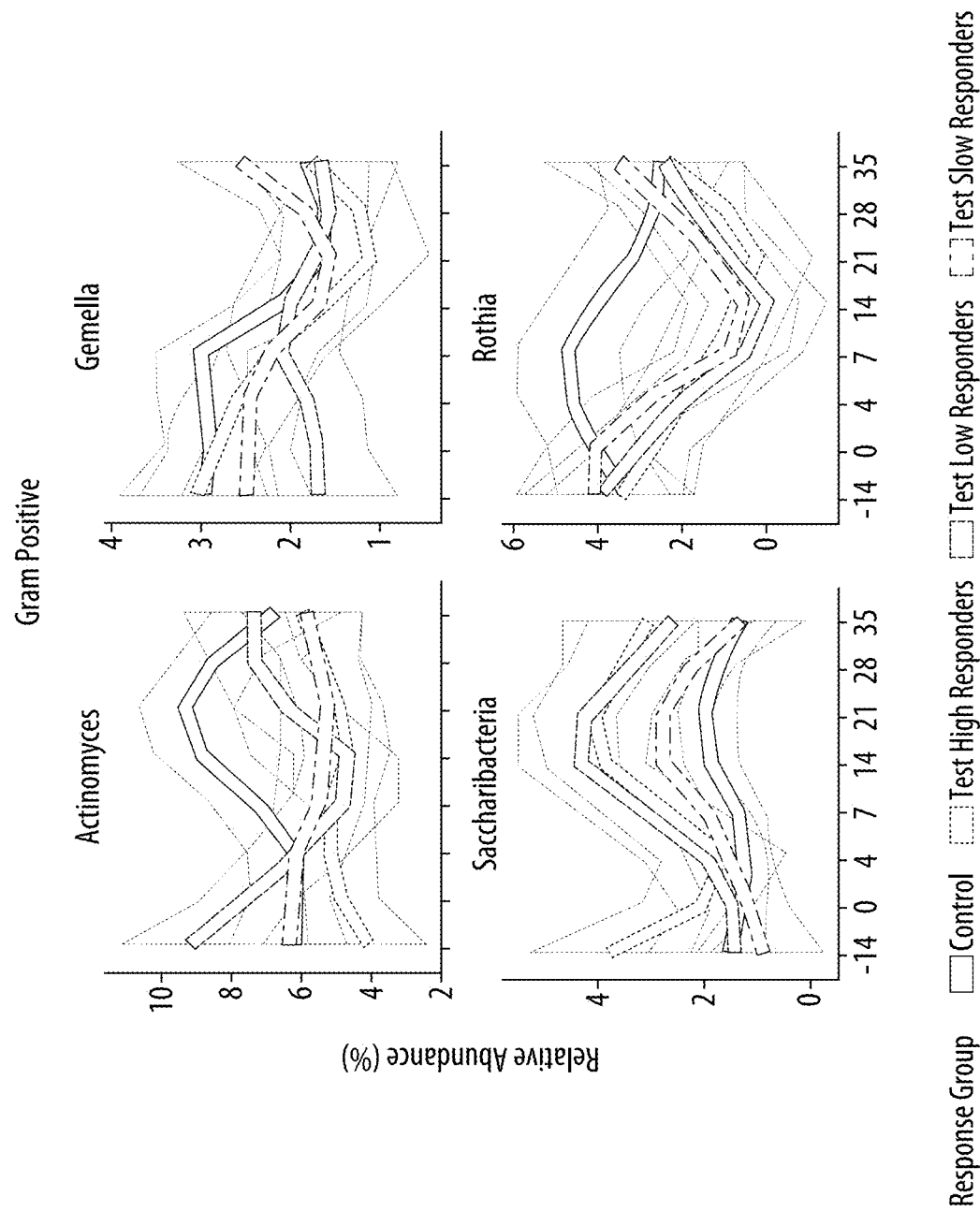
Figure 5E:
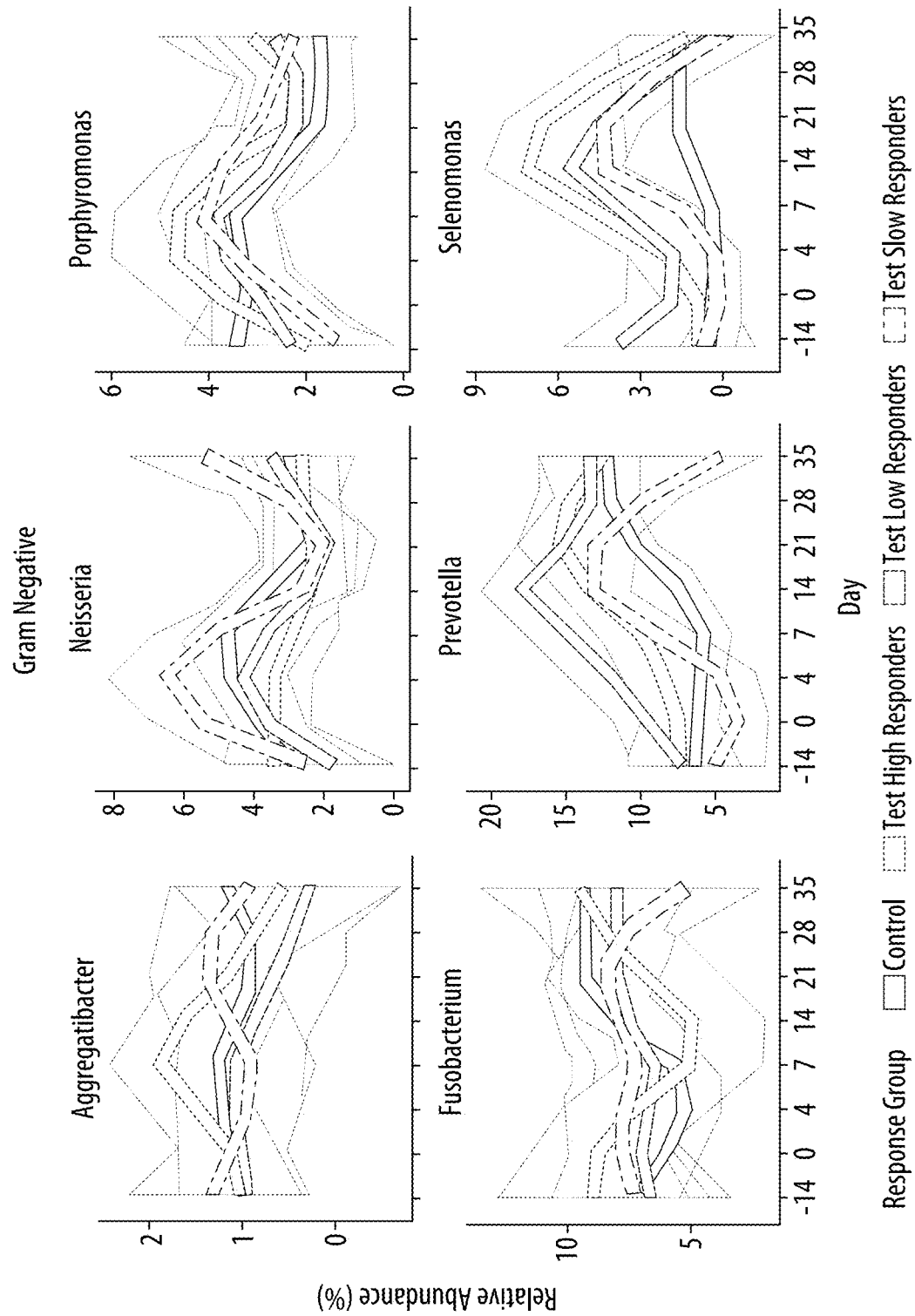
Figure 5E:
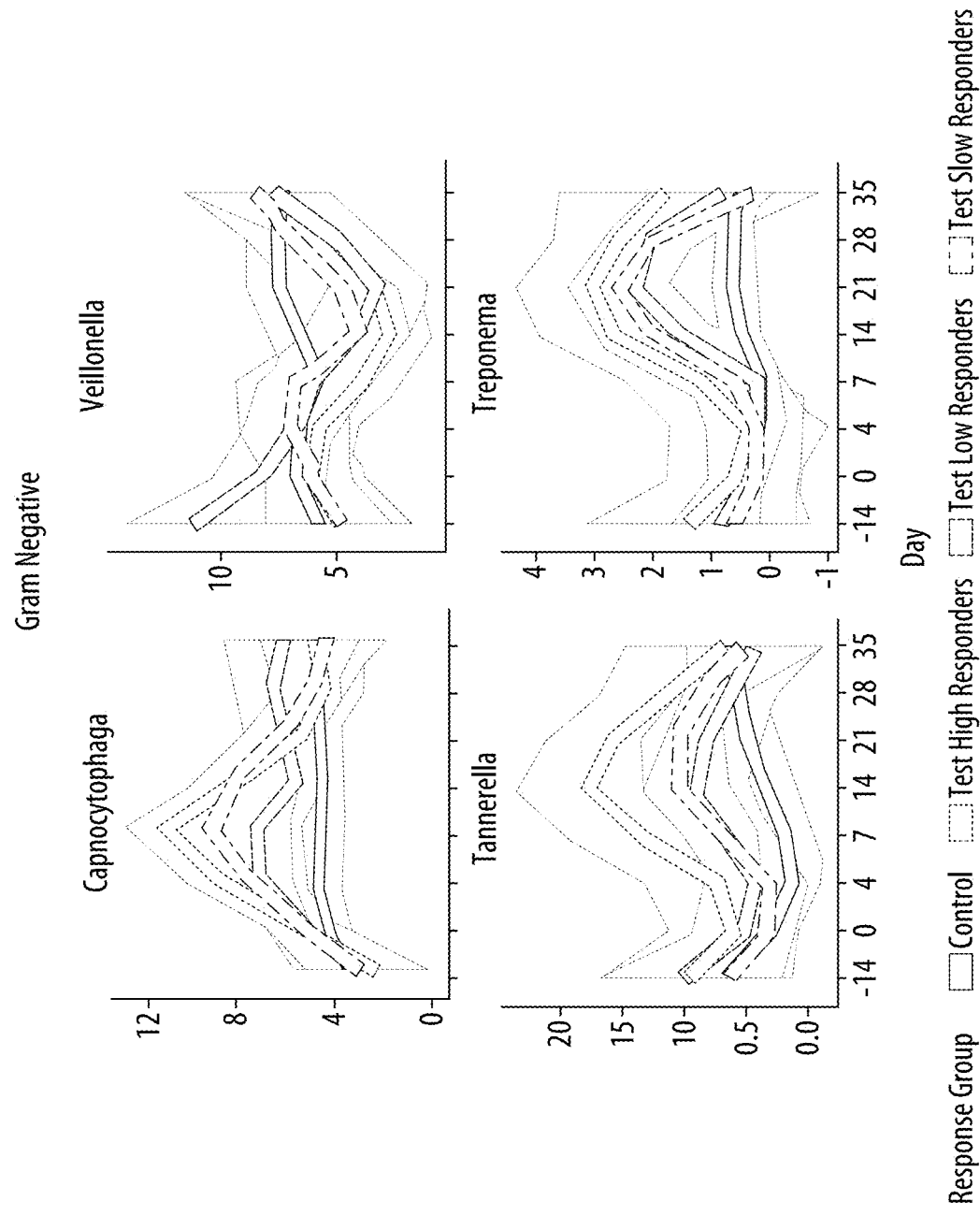

Taxonomic analysis of sub-gingival plaque samples during the onset of experimental gingivitis confirmed the well-known and characteristic shift from a health associated Gram-positive to a disease-associated Gram-negative composition associated with gingivitis. For example, in all three clinical response groups, the two most abundant Gram-positive phyla, *Firmicutes* and *Actinobacteria* decreased in relative abundance (FIG. 5C). In contrast, the most abundant Gram-negative phyla, *Bacteroidetes*, increased in its relative abundance (FIG. 5C). However, group-level analysis at the genus level revealed novel differences in the abundance profiles during the development of gingivitis among the three different response groups (FIGS. 5D-5F and FIG. 9). An increase in genera within the Phylum *Bacteroidetes* was not uniform across all three clinical response groups described in this study. For example, *Tannerella* increased late in gingivitis in both low and slow response groups, but was dramatically reduced in comparison to the high response group (FIG. 5E). In contrast, *Prevotella* displayed the greatest increase within the low response group, even though the high and slow groups eventually showed a significant increase later during gingivitis development (FIG. 5E). Other abundant gram-negative associated genera, such as *Porphyromonas* and *Fusobacterium*, also displayed inter-group variations throughout the induction phase (Day 0-Day 21). Interestingly, a gram-positive member of the candidate phyla radiation (CPR), '*Candidatus saccharibacteria*' (formerly TM7) which are ultra-small parasitic bacterial epibionts, selectively increased among high and low responders, but not in the slow response group.

Figure 5F:
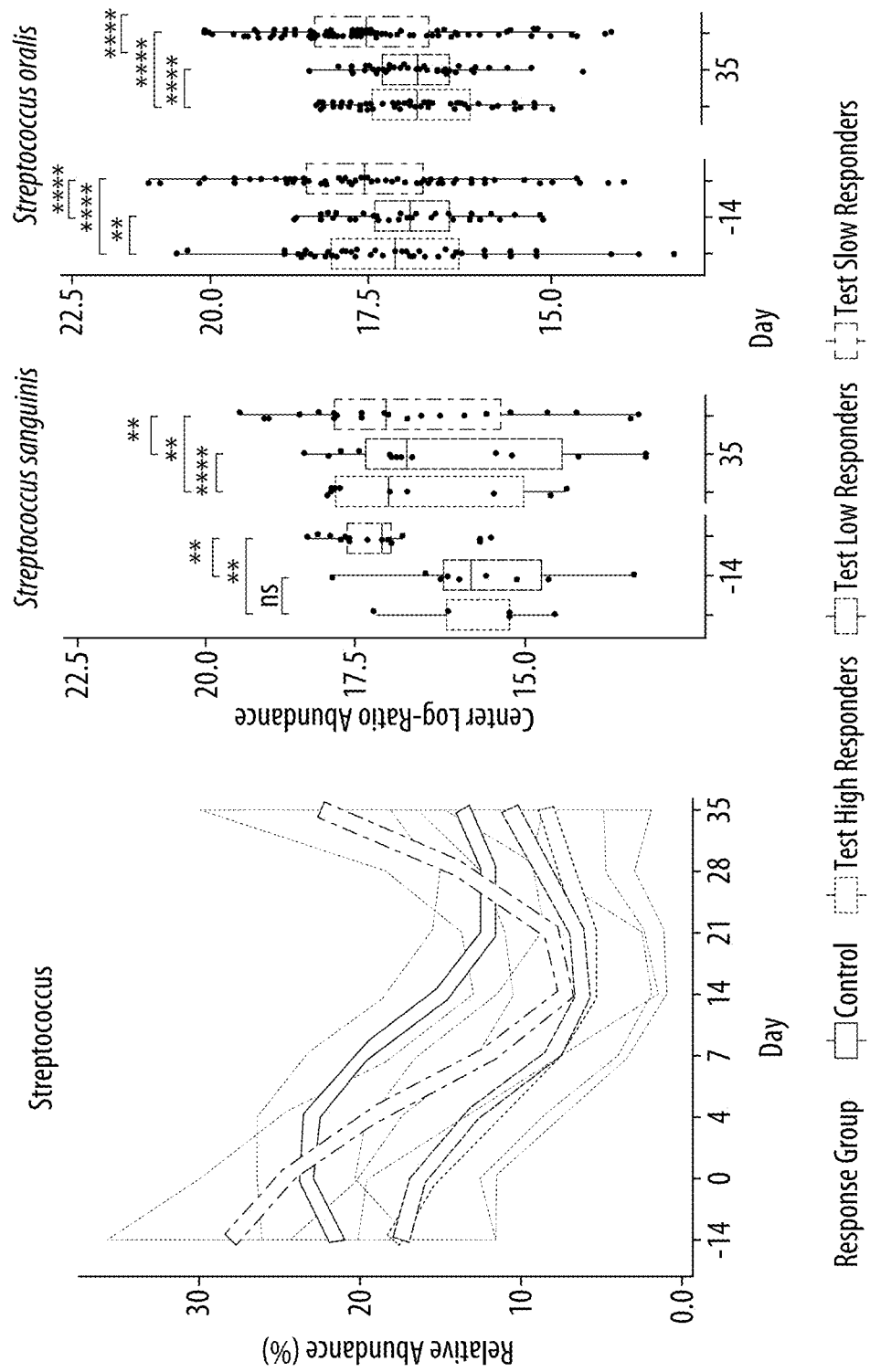

Consistent with the changes in alpha and beta diversity, the most notable differences overall were observed in the slow response group, with the rate of *Firmicutes* decrease and the concomitant increase Bacteriodetes being markedly delayed (FIG. 5C). At the genus level, *Streptococcus*, which is a member of the phyla *Firmicutes*, decreased at a slower rate in comparison to the high and low groups as well as was initially higher at the beginning of the study (Day −14 and Day 0) and even regains in prominence at the end of the study (Day 35) (FIG. 5F). The observed delay in both the alpha and beta diversity among the slow response group is, therefore, most likely a consequence of the prolonged presence of *Streptococcus* which is both the most abundant genera within the healthy sub gingival pocket and uniquely characteristic of this response group. These observations are entirely consistent with the distinct delay in the clinical manifestations of gingivitis within the slow group (FIGS. 2E-2G). Of particular note, we observed that the slow 258 group had statistically significant higher relative abundance of ASV's classified as *Streptococcus sanguinis* and *Streptococcus oralis* species during the pre-induction phase prior to the start of the study (Day −14 and Day 0) as well as during resolution phase at the end of this study (Day 35), which resulted in trends towards pre-induction levels (FIG. 5F).

Overall, the trajectory of the slow response group can be readily discerned from the other community profiles and, as shown above, this group can elicit significantly lower IL-1b responses (FIG. 2K and FIG. 2L). In contrast, the high and low clinical response groups displayed a lack of clear separation in alpha and beta diversity measures during the microbially induced inflammation, which correlates with their highly similar plaque accumulation rates (FIG. 2E).

A delayed gram + to gram − transition may contribute to the slow clinical response phenotype.

Discussion

The human experimental gingivitis model provides a unique opportunity to study bacterial community succession during plaque accumulation and the subsequent host response in real time. The first human experimental gingivitis study (as well as several subsequent studies have identified high and low clinical response groups based upon the gingival index, a measure of local gingival inflammation. Disclosed herein, two clinical host response groups were also found and were characterized by significantly lower gingival index and bleeding on probing within the low response group compared to the high response group (FIG. 2F and FIG. 2G). Furthermore, by conducting a longitudinal trajectory-based clustering of inflammatory changes, compared to cross-sectional clustering previously performed, an additional "slow" clinical response group characterized by a delayed increase in microbial plaque accumulation and a corresponding delay in clinical inflammatory indices was identified (FIGS. 2E-2G).

Characterization of these different clinical response groups revealed previously unrecognized variability in the microbial succession and host response that occurs during gingivitis. The alpha diversity within the slow response group showed a completely separate community in terms of both the rate of plaque growth and community compositional changes in comparison to the high and low response groups (FIG. 2E and FIG. 5A)—together demonstrating the great degree of variation in gingivitis within the human population. Reduced bacterial accumulation rates in the human population have been reported previously. However, in this study which defines three clinical response groups, it was found the slow response group had statistically significant higher relative abundance of amplicon sequence variants (ASV's) classified as *Streptococcus sanguinis* and *Streptococcus oralis* species at Day −14, the pre-induction phase prior to the start of the study, and Day 35 during the resolution phase (FIG. 5F). This suggests the possibility that participants belonging to the slow response group may be identifiable prior to the study and are predisposed to reduced plaque formation rates and a slower shift to Gram-negative species. This delay in the gram-negative shift where inflammophilic bacterial species increase in relative abundance may contribute to less often episodes of gingivitis in these individuals. The genus *Streptococcus* is composed of predominantly health-associated species known to inhibit other Gram-negative species by the production of bacteriocins and hydrogen peroxide. *S. sanguinis* and *S. oralis* species have been shown to inhibit *Aggregatibacter actinomycetemcomitans*, *Porphyromonas gingivalis* and *Prevotella intermedia*; therefore, by remaining persistent within the community at a high abundance, they may be delaying the overall microbial succession and plaque growth rates seen in the high and low response groups during the onset of experimental gingivitis.

It was also observed that the lack of expression of IL-1β in the slow clinical response group did not significantly contribute to gingival inflammation among individuals within this group even though this inflammatory mediator has been considered a hallmark of gingival inflammation and repeatedly shown to be strongly associated with experimental gingivitis in a number of clinical studies. Therefore, the significantly different IL-1β responses in the high and slow clinical response groups clearly demonstrates that multiple inflammatory etiologies can elicit the clinical manifestations of gingivitis.

In contrast to the slow clinical response group, both the high and low clinical response groups displayed a similar rapid increase in bacterial plaque accumulation and microbial ecological succession patterns. Although, several differences in the microbial composition were noted, the overall lack of host chemokine inflammatory mediator expression with a high microbial load is strongly suggestive that in low clinical response individuals it is the host response, as opposed to the microbial composition, that is primarily responsible for the low gingival inflammation. This was observed in that both the gingival index and most notably the bleeding on probing scores never attained the same degree of clinical inflammation in comparison to the high clinical response group although the microbial load continued to increase until the end of the induction phase of the study. Furthermore, it was found that five chemokines (MCP-1/CCL2, MIP-3α/CCL20, SCYB16/CXCL16, GRO-α/CXCL1, and MPIF-1/CCL23), which have been shown to contribute to either normal bone turnover processes or alveolar bone loss during periodontitis, displayed overall significantly lower chemokine levels in our low response group when compared to our high response group (FIGS. 4A-4F). However, further investigations are needed to determine if minor microbiome differences or host immune variability, or both, contribute to the difference between high and low clinical response groups. Data in FIG. 4A shows that there is a significant and rapid decrease in CCL3 a chemokine involved in inducing osteoclastogenesis Examination of chemokines that regulate neutrophil migration revealed that all individuals, regardless of their clinical response phenotype, modulated expression of neutrophil activation. Healthy gingival homeostasis requires a chemokine controlled neutrophil migration process from the gingival vasculature, through the junctional epithelium, and into the gingival crevice. In mice, this process has been shown to require select chemokine receptors and ligands as well commensal bacterial colonization. In humans, IL-8/CXCL8 has been shown to be selectively expressed in clinically healthy junctional epithelial tissue providing a concentration gradient for constant neutrophil surveillance of the periodontium. However, during experimental gingivitis it was found that this process was disrupted in that the levels of five (IL-8/CXCL8, GRO-α/CXCL1, GRO-β/CXCL2, ENA-78/CXCL5, GCP-2/CXCL6) out of the six neutrophil chemokines we examined did not increase, even though more neutrophils migrated into the junctional epithelium and is typically observed in gingivitis. Although a decrease in IL-8/CXCL8 during gingivitis has been previously reported by several groups the more extensive failure to increase a variety of other neutrophil chemokines has not been previously reported. In contrast, macrophage migration inhibitory factor (MIF), not previously recognized as major gingival associated neutrophil chemokine to be present in GCF, increased in all response groups after the induction of experimental gingivitis. In fact, analysis comparing MIF, CXCL8, and neutrophil migration clearly demonstrated that MIF replaced IL-8/CXCL8 as the neutrophil chemokine that recruits neutrophils during experimental gingivitis (FIG. 3B) The decrease in two CXCR1 neutrophil activating chemokines, GCP-2/CXCL6 and IL-8/CXCL8, provides a mechanism for the reduced neutrophil activation state previously described during experimental gingivitis. In addition, the selective increase in MIF, which does not engage the neutrophil activating receptor CXCR1 provides a mechanism by which neutrophil migration is maintained without activation and potential tissue damage during experimental gingivitis in each clinical response group. However, due to the association between MIF and alveolar bone loss it is possible that continued MIF secretion may directly or indirectly contribute to bone loss in the transition from gingivitis to periodontitis.

Experimental gingivitis also modulated the expression of CCL3, a bone remodeling chemokine through activation of osteoclastogenesis. Furthermore, because it is well established that the para-inflammatory state during episodes of gingivitis can develop into periodontitis, significantly lower levels of CCL3 in all response groups may represent previously unrecognized host protection mechanism to protect against bone loss during gingivitis. Consistent with this, it has been previously demonstrated that germ free mice display an increase in alveolar bone height, revealing the contribution of oral commensal bacteria to oral alveolar bone homeostasis though a balance of osteoblastogeneisis and osteoclastogenesis. More recently, consistent with the contribution of the oral commensal bacteria to alveolar bone remodeling, it has been found that germ free mice do not express CCL3. Therefore, the significant reduction in CCL3, in all clinical response groups is consistent with a change in alveolar bone homeostasis that favors less bone resorption. The shift in both neutrophil activation and bone homeostasis mediators reveals a previously unrecognized host response mechanism that serves to protect the host from localized tissue and bone damage during periods of gingival inflammation.

In conclusion, by providing the most comprehensive temporal characterization of human inflammatory responses to oral bacterial-induced inflammation we identified three distinct clinical phenotypes inducing a "high", "low", or "slow" gingival inflammatory response. The slow clinical inflammatory phenotype was characterized by linear responses to microbial biomass accumulation in the gingiva and exhibited higher relative abundances of *Streptococcus* spp. than the other phenotypes, which led to a clinically more resistant homeostatic state. In addition, it is particularly noteworthy that the slow clinical response group did not contain high gingival crevicular fluid levels of IL-1β revealing a novel inflammation response for this group of individuals. In contrast, the high and low clinical response groups demonstrated strikingly similar microbial succession patterns that, however, led to significantly different inflammatory responses. Furthermore, two novel protective mechanisms were identified. One, although during bone destructive periodontitis neutrophil migration is associated with an increase in IL-8/CXCL8 in the junctional epithelium, in reversible bone sparing gingival inflammation, MIF, a neutrophil chemokine not normally associated with healthy homeostasis increases demonstrating a shift in the neutrophil recruitment regime during gingivitis. Importantly, MIF-mediated neutrophil recruitment is associated with an alternative neutrophil chemokine expression regime with near shut down of CXCR1-binding chemokines GCP-2/CXCL6 and IL-8/CXCL8, which activate the oxidative killing pathway that causes tissue collateral damage. The lack of activation of neutrophil oxidative killing during gingivitis has been reported previously as a tissue saving response however the mechanism for this has not been previously shown. Secondly, MIP-1α/CCL3, a chemokine associated with bone homeostasis is completely shut down during experimental gingivitis indicative of a significant alteration in bone turnover processes. Collectively, these findings pave the way for the more attention to be paid to individual differences in both the microbial composition and host response to more fully understand bacterial dysbiosis driven diseases.

TABLE 2

Alpha diversity indices (mean ± SD) during induction and resolution of experimental gingivitis.

|  | Control | | | |
|---|---|---|---|---|
|  | Hygiene Phase | Induction Phase | | |
|  | −14 | 0 | 4 | 7 |
| Shannon diversity | 4.35 ± 0.43 | 4.26 ± 0.53 | 4.3 ± 0.38 | 4.2 ± 0.44 |
| Chao1 diversity | 131.23 ± 50.14 | 123.04 ± 36.71 | 121.57 ± 43.48 | 115.74 ± 56.61 |
| Simpson's inverse diversity | 58.38 ± 30.45 | 54.68 ± 25.09 | 56.41 ± 26.26 | 53.15 ± 28.59 |
| Faith's phylogenetic diversity | 7.69 ± 2.35 | 7.41 ± 2.14 | 7.26 ± 1.82 | 6.74 ± 2.11 |
| Observed species | 130.95 ± 49.92 | 122.9 ± 36.7 | 121.43 ± 43.41 | 115.6 ± 56.55 |
| Shannon diversity | 4.35 ± 0.59 | 4.33 ± 0.66 | 4.62 ± 0.38**§ | 4.54 ± 0.46** |
| Chao1 diversity | 142.66 ± 120.8 | 145.06 ± 82.26 | 161.78 ± 84.33* | 148.1 ± 75.05* |
| Simpson's inverse diversity | 70.03 ± 61.36 | 65.04 ± 52.69 | 85.87 ± 46.71**§ | 84.74 ± 41.06* |
| Faith's phylogenetic diversity | 8.08 ± 3.74 | 8.01 ± 3.53 | 9.04 ± 2.89** | 8.89 ± 2.43*** |
| Observed species | 142.05 ± 120.6 | 144.86 ± 82.2 | 161.67 ± 84.07* | 148 ± 74.97* |

|  | Control | | | |
|---|---|---|---|---|
|  | Induction Phase | | Resolution Phase | |
|  | 14 | 21 | 28 | 35 |
| Shannon diversity | 4.38 ± 0.5 | 4.4 ± 0.35 | 4.38 ± 0.38 | 4.36 ± 0.46 |
| Chao1 diversity | 132.47 ± 51.83 | 126.07 ± 38.16 | 121.96 ± 44.06 | 127.02 ± 52.66 |
| Simpson's inverse diversity | 65.8 ± 32.96 | 64.72 ± 30.02 | 66.08 ± 29.81 | 64.09 ± 30.8 |

TABLE 2-continued

Alpha diversity indices (mean ± SD) during induction and resolution of experimental gingivitis.

| | | | | |
|---|---|---|---|---|
| Faith's phylogenetic diversity | 7.97 ± 2.41 | 8.05 ± 1.99 | 7.87 ± 1.87 | 8.12 ± 2.12 |
| Observed species | 132.33 ± 51.72 | 126 ± 38.18 | 121.62 ± 44.1 | 126.95 ± 52.59 |
| Shannon diversity | 4.85 ± 0.28***‡ | 4.72 ± 0.34** ‡ | 4.35 ± 0.27 | 4.36 ± 0.34 |
| Chao1 diversity | 189.63 ± 65.79***§ | 171.2 ± 70.17** | 114.85 ± 37.66 | 120.68 ± 45.17 |
| Simpson's inverse diversity | 106.45 ± 30.98***‡ | 97.76 ± 34.81***‡ | 61.16 ± 23.69 | 63.15 ± 29.97 |
| Faith's phylogenetic diversity | 11.08 ± 2.18***‡ | 11.1 ± 2.13***‡ | 7.83 ± 2.1 | 7.96 ± 1.94 |
| Observed species | 189.48 ± 65.74***§ | 171.1 ± 70.11** | 114.76 ± 37.67 | 120.48 ± 45.02 |

Statistical significant difference for test side vs control side, *$p < 0.05$, $p < 0.01$ or *$p < 0.001$.

Statistical significant difference for the time trend on the test side; induction phase values vs Day 0, §$p < 0.05$, †$p < 0.01$ or ‡$p < 0.001$.

TABLE 3

Alpha diversity indices (mean ± SD) during induction and resolution of experimental gingivitis.

| | Control | | | |
|---|---|---|---|---|
| | Hygiene Phase | Induction Phase | | |
| | −14 | 0 | 4 | 7 |
| Shannon diversity | 4.35 ± 0.43 | 4.26 ± 0.53 | 4.3 ± 0.38 | 4.2 ± 0.44 |
| Chao1 diversity | 131.23 ± 50.14 | 123.04 ± 36.71 | 121.57 ± 43.48 | 115.74 ± 56.61 |
| Simpson's inverse diversity | 58.38 ± 30.45 | 54.68 ± 25.09 | 56.41 ± 26.26 | 53.15 ± 28.59 |
| Faith's phylogenetic diversity | 7.69 ± 2.35 | 7.41 ± 2.14 | 7.26 ± 1.82 | 6.74 ± 2.11 |
| Observed species | 130.95 ± 49.92 | 122.9 ± 36.7 | 121.43 ± 43.41 | 115.6 ± 56.55 |
| Shannon diversity | 4.51 ± 0.84 | 4.41 ± 0.8 | 4.67 ± 0.44 | 4.38 ± 0.43 |
| Chao1 diversity | 196.18 ± 219.78 | 61.98 ± 106.65 | 174.42 ± 84.88 | 122.35 ± 58.83 |
| Simpson's inverse diversity | 96.11 ± 105.12 | 72.89 ± 63.39 | 92.64 ± 42.73 | 71.05 ± 33.83 |
| Faith's phylogenetic diversity | 10.19 ± 5.48 | 8.49 ± 4.23 | 10.43 ± 3.52 | 8.81 ± 2.85 |
| Observed species | 196 ± 219.35 | 61.83 ± 106.73 | 174.33 ± 84.85 | 122.33 ± 58.81 |
| Shannon diversity | 4.36 ± 0.34 | 4.38 ± 0.63 | 4.72 ± 0.52 | 4.58 ± 0.59 |
| Chao1 diversity | 115.39 ± 44.77 | 143.87 ± 93.23 | 87.74 ± 131.92 | 64.37 ± 109.91 |
| Simpson's inverse diversity | 66.9 ± 20.75 | 68.01 ± 58.88 | 103.86 ± 73.35 | 92.5 ± 59.04 |
| Faith's phylogenetic diversity | 6.66 ± 2.49 | 8.1 ± 2.59 | 9.89 ± 3.27 | 9.53 ± 2.41 |
| Observed species | 114.5 ± 44.23 | 143.67 ± 93.22 | 187.5 ± 131.33 | 64.17 ± 109.83 |
| Shannon diversity | 4.24 ± 0.56 | 4.24 ± 0.65 | 4.52 ± 0.21 | 4.64 ± 0.41 |
| Chao1 diversity | 125.17 ± 44.88 | 134.58 ± 63.53 | 136.04 ± 32.09 | 155.2 ± 57.74 |
| Simpson's inverse diversity | 54.72 ± 38.13 | 57.82 ± 46.37 | 69.38 ± 19.18 | 89.2 ± 32.16 |
| Faith's phylogenetic diversity | 7.61 ± 2.7 | 7.64 ± 3.93 | 7.54 ± 1.38 | 8.46 ± 2.34 |
| Observed species | 124.44 ± 44.81 | 134.33 ± 63.24 | 136 ± 32.08 | 155.12 ± 57.64 |

| | Control | | | |
|---|---|---|---|---|
| | Induction Phase | | Resolution Phase | |
| | 14 | 21 | 28 | 35 |
| Shannon diversity | 4.38 ± 0.5 | 4.4 ± 0.35 | 4.38 ± 0.38 | 4.36 ± 0.46 |
| Chao1 diversity | 132.47 ± 51.83 | 126.07 ± 38.16 | 121.96 ± 44.06 | 127.02 ± 52.66 |
| Simpson's inverse diversity | 65.8 ± 32.96 | 64.72 ± 30.02 | 66.08 ± 29.81 | 64.09 ± 30.8 |
| Faith's phylogenetic diversity | 7.97 ± 2.41 | 8.05 ± 1.99 | 7.87 ± 1.87 | 8.12 ± 2.12 |
| Observed species | 132.33 ± 51.72 | 126 ± 38.18 | 121.62 ± 44.1 | 126.95 ± 52.59 |
| Shannon diversity | 4.82 ± 0.32 | 4.68 ± 0.31 | 4.4 ± 0.44 | 4.49 ± 0.41 |
| Chao1 diversity | 189.89 ± 74.78 | 163.27 ± 55.05 | 126.87 ± 67.36 | 140.11 ± 65.6 |
| Simpson's inverse diversity | 106.59 ± 41.92* | 93.57 ± 29.93 | 70.12 ± 36.83 | 74.5 ± 42.5 |
| Faith's phylogenetic diversity | 11.74 ± 2.31** | 11.51 ± 2.67** | 8.37 ± 2.79 | 9.14 ± 2.16 |
| Observed species | 189.67 ± 74.76 | 163.17 ± 55.07 | 126.67 ± 67.5 | 140 ± 65.39 |
| Shannon diversity | 4.78 ± 0.24 | 4.62 ± 0.35 | 4.42 ± 0.16 | 4.35 ± 0.41 |

TABLE 3-continued

Alpha diversity indices (mean ± SD) during induction and resolution of experimental gingivitis.

| | | | | |
|---|---|---|---|---|
| Chao1 diversity | 169.75 ± 37.47 | 152.15 ± 60.44 | 115.94 ± 18.9 | 113.58 ± 48.67 |
| Simpson's inverse diversity | 98.41 ± 27.21 | 89.06 ± 34.13 | 67.55 ± 13.44 | 69.74 ± 30.81 |
| Faith's phylogenetic diversity | 10.54 ± 1.45* | 10.4 ± 2.17 | 8.03 ± 1.06 | 8.29 ± 2.05 |
| Observed species | 169.67 ± 37.46 | 152 ± 60.57 | 115.83 ± 18.65 | 113.5 ± 48.51 |
| Shannon diversity | 4.91 ± 0.3** | 4.82 ± 0.36** | 4.26 ± 0.19 | 4.27 ± 0.24 |
| Chao1 diversity | 202.71 ± 77.21 | 189.2 ± 86.3 | 106.12 ± 17.09 | 112.47 ± 23.12 |
| Simpson's inverse diversity | 11.71 ± 27.53** | 106.36 ± 39.86** | 50.93 ± 15.29 | 51.19 ± 15.28 |
| Faith's phylogenetic diversity | 11 ± 2.59** | 11.29 ± 1.86** | 7.34 ± 2.22 | 6.94 ± 1.28 |
| Observed species | 202.56 ± 77.13 | 189.11 ± 86.12 | 106.11 ± 17.08 | 112.11 ± 22.87 |

Statistical significant difference for the time trend on for each responder group compared to baseline; induction phase values vs Day 0,
*$p < 0.05$,
**$p < 0.01$ or
***$p < 0.001$.

TABLE 4

Genus level comparisons by Day between Responder Groups using the Tukey HSD test with FDR adjusted p values with mean agglomerated count data.

| Day | Genus | group1 | group2 | estimate | conf.low | conf.high | p.adj | p.adj. signif |
|---|---|---|---|---|---|---|---|---|
| −14 | g_Actinomyces | Test High Responders | Test Low Responders | 0.00014849 | 6.95E−06 | 0.000290027 | 0.0367 | * |
| −14 | g_Ruminococcaceae_[G-2] | Test High Responders | Test Low Responders | −3.86E−06 | −7.38E−06 | −3.39E−07 | 0.027 | * |
| −14 | g_Ruminococcaceae_[G-2] | Test High Responders | Test Slow Responders | −3.86E−06 | −7.07E−06 | −6.45E−07 | 0.0132 | * |
| −14 | g_Saccharibacteria_(TM7)_[G-1] | Test High Responders | Test Slow Responders | −9.51E−05 | −0.000176396 | −1.38E−05 | 0.0164 | * |
| −14 | g_Selenomonas | Test Low Responders | Test Slow Responders | −0.000108402 | −0.000195693 | −2.11E−05 | 0.00987 | ** |
| −14 | g_Veillonella | Test High Responders | Test Low Responders | 0.000215543 | 9.84E−07 | 0.000430103 | 0.0486 | * |
| 0 | g_Parvimonas | Test Low Responders | Test Slow Responders | −4.91E−05 | −9.18E−05 | −6.46E−06 | 0.0186 | * |
| 0 | g_Prevotella | Test Low Responders | Test Slow Responders | −0.000218418 | −0.000422018 | −1.48E−05 | 0.0315 | * |
| 4 | g_Abiotrophia | Test Low Responders | Test Slow Responders | 5.11E−05 | 4.20E−06 | 9.80E−05 | 0.0282 | * |
| 4 | g_Selenomonas | Test High Responders | Test Slow Responders | −7.77E−05 | −0.000134627 | −2.08E−05 | 0.00396 | ** |
| 4 | g_Selenomonas | Test Low Responders | Test Slow Responders | −6.80E−05 | −0.000124904 | −1.11E−05 | 0.0137 | * |
| 7 | g_Lachnospiraceae_[G-3] | Test High Responders | Test Low Responders | −4.72E−05 | −8.29E−05 | −1.15E−05 | 0.00557 | ** |
| 7 | g_Lachnospiraceae_[G-3] | Test High Responders | Test Slow Responders | −3.99E−05 | −7.33E−05 | −6.51E−06 | 0.0139 | * |
| 7 | g_Megasphaera | Test High Responders | Test Low Responders | 1.59E−05 | 4.71E−07 | 3.14E−05 | 0.0413 | * |
| 7 | g_Megasphaera | Test Low Responders | Test Slow Responders | −1.68E−05 | −3.13E−05 | −2.37E−06 | 0.0172 | * |
| 7 | g_Selenomonas | Test High Responders | Test Slow Responders | −8.60E−05 | −0.000160172 | −1.18E−05 | 0.0178 | * |
| 14 | g_Absconditabacteria_(SR1)_[G-1] | Test High Responders | Test Low Responders | −2.49E−05 | −4.77E−05 | −2.00E−06 | 0.0286 | * |
| 14 | g_Catonella | Test Low Responders | Test Slow Responders | 3.32E−05 | 7.63E−06 | 5.88E−05 | 0.00655 | ** |
| 14 | g_Megasphaera | Test High Responders | Test Low Responders | 2.37E−05 | 3.97E−06 | 4.34E−05 | 0.0131 | * |
| 14 | g_Megasphaera | Test Low Responders | Test Slow Responders | −2.26E−05 | −4.05E−05 | −4.58E−06 | 0.00899 | ** |
| 14 | g_Selenomonas | Test High Responders | Test Slow Responders | −9.93E−05 | −0.000184546 | −1.40E−05 | 0.017 | * |
| 14 | g_Solobacterium | Test High Responders | Test Low Responders | 3.30E−05 | 8.18E−06 | 5.79E−05 | 0.00523 | ** |
| 14 | g_Solobacterium | Test Low Responders | Test Slow Responders | −2.95E−05 | −5.22E−05 | −6.85E−06 | 0.00639 | ** |
| 14 | g_Treponema | Test High Responders | Test Low Responders | −6.76E−05 | −0.00013347 | −1.77E−06 | 0.0423 | * |
| 21 | g_Absconditabacteria_(SR1)_[G-1] | Test High Responders | Test Slow Responders | −2.87E−05 | −5.30E−05 | −4.38E−06 | 0.0153 | * |
| 21 | g_Mitsuokella | Test High Responders | Test Low Responders | −5.39E−06 | −1.07E−05 | −6.70E−08 | 0.0462 | * |
| 21 | g_Mitsuokella | Test High Responders | Test Slow Responders | −5.39E−06 | −1.02E−05 | −5.31E−07 | 0.0247 | * |
| 21 | g_Saccharibacteria_(TM7)_[G-3] | Test High Responders | Test Low Responders | −2.11E−05 | −3.84E−05 | −3.81E−06 | 0.0115 | * |
| 21 | g_Saccharibacteria_(TM7)_[G-3] | Test High Responders | Test Slow Responders | −2.57E−05 | −4.15E−05 | −9.92E−06 | 0.000514 | *** |
| 28 | g_Filifactor | Test High Responders | Test Low Responders | −1.56E−05 | −3.05E−05 | −5.99E−07 | 0.0389 | * |
| 28 | g_Filifactor | Test High Responders | Test Slow Responders | −1.39E−05 | −2.76E−05 | −2.55E−07 | 0.0445 | * |
| 28 | g_Ruminococcaceae_[G-2] | Test High Responders | Test Slow Responders | −1.42E−06 | −2.72E−06 | −1.19E−07 | 0.0279 | * |
| 28 | g_Saccharibacteria_(TM7)_[G-3] | Test High Responders | Test Low Responders | −1.43E−05 | −2.79E−05 | −8.06E−07 | 0.0343 | * |
| 28 | g_Saccharibacteria_(TM7)_[G-3] | Test High Responders | Test Slow Responders | −1.39E−05 | −2.62E−05 | −1.52E−06 | 0.0225 | * |
| 35 | g_Filifactor | Test High Responders | Test Low Responders | −1.73E−05 | −3.27E−05 | −1.83E−06 | 0.0232 | * |
| 35 | g_Filifactor | Test High Responders | Test Slow Responders | −1.73E−05 | −3.14E−05 | −3.18E−06 | 0.0111 | * |

TABLE 4-continued

Genus level comparisons by Day between Responder Groups using the Tukey HSD test with FDR adjusted p values with mean agglomerated count data.

| Day | Genus | group1 | group2 | estimate | conf.low | conf.high | p.adj | p.adj. signif |
|---|---|---|---|---|---|---|---|---|
| 35 | g_Prevotella | Test High Responders | Test Slow Responders | −0.000247415 | −0.00048381 | −1.10E−05 | 0.0373 | * |
| 35 | g_Prevotella | Test Low Responders | Test Slow Responders | −0.000284274 | −0.000520669 | −4.79E−05 | 0.013 | * |
| 35 | g_Saccharibacteria_ (TM7)_[G-3] | Test High Responders | Test Slow Responders | −2.54E−05 | −5.08E−05 | −8.51E−08 | 0.049 | * |
| 35 | g_Solobacterium | Test High Responders | Test Slow Responders | −2.53E−05 | −5.05E−05 | −4.14E−08 | 0.0495 | * |
| 35 | g_Streptococcus | Test High Responders | Test Slow Responders | 0.000433624 | 4.00E−05 | 0.000827259 | 0.026 | * |

Only Significant differences between Responder Groups by Day and Genus are shown. If not shown the comparison was determined to be not significant (FDR Adjusted P value)
*p < 0.05,
**p < 0.01,
***p < 0.001

Example 2

Oral infections are often correlated with systemic health issues. Human hosts fall into three clinical Inflammatory Responder Types (IRTs) associated with microbially-induced oral infections: High-IRT, Low-IRT, and Slow-IRT. A highly temporal and multi-omic analysis of microbially-induced inflammation using the experimental gingivitis (EG) model reveals that localized inflammation induced by normal plaque accumulation and maturation results in host mediator changes in distant healthy tooth sites located contralaterally in the mouth. The host's IRT was also related to the extent and severity of this contralateral effect.

As part of a recent EG study which incorporated a split mouth design, effectively providing intra-oral controls for each subject for the duration of the study, a high-resolution analysis of host mediator, microbiome, and clinical data for 21 young healthy individuals over a period of 7 weeks. During the initial 14-day preinduction period (Days −14 to 0), study participants 21 received a cleaning and examination. During a 21-day induction period (Days 0-21) inflammation was induced by refraining from brushing at the test side of the mouth while brushing continued on the control side of the mouth. Evaluation continued during a 14-day resolution phase (Days 21-35) in which a cleaning was done at Day 22. Results from this study not only verified previously observed clinical variations in host response to plaque-induced inflammation reported in the literature (High and Low response), but also identified a novel clinical response type, Slow. These variations in gingival inflammation observed in humans are now proposed as clinical Inflammatory Response Types (IRTs). Each of these phenotypes revealed distinctly defining clinical, microbial, and host mediator dynamics. In brief, High-IRT have a rapid plaque growth rate, rapid increase in gram-negative Bacteroidetes, high levels of host mediators, and high levels of inflammation; Low-IRT have a rapid plaque growth rate, rapid increase in gram-negative Bacteroidetes, low levels of host mediators, and low levels of clinical inflammation; and Slow-IRT have a delayed plaque growth rate, sustained higher levels of gram-positive Streptococci, and delayed onset of clinical inflammation yet ultimately reached high levels of inflammation—similar to High-IRT.

A study was undertaken to characterize changes observed in distant healthy control sites located contralaterally on the maxilla in relation to gingival inflammation being induced in test sites from normal plaque accumulation and maturation over a period of 21 Day induction period. Significant alterations within the human oral cavity that directly results from induced inflammation occurring in distant sites within the oral cavity. Notably, increases in pro-inflammatory host mediators associated with periodontal inflammation, IL-8, IL-6, IL1-b, and TNF-α were observed as well as a dysbiotic ecological shift in the subgingival microbiome within healthy controls without any significant clinically observed inflammation within these distant healthy sites. This effect was influenced by an individual's Inflammatory Responder Type (IRT). Microbial shifts in healthy sites were most evident in the High- and Slow-IRT with the High-IRT having a rapid contralateral effect and the Slow-IRT having a delayed contralateral effect. Interestingly, the Low-IRT, which are able to modulate their immune response within test sites and do not obtain the same elevated levs of inflammation as the High- and Slow-IRT, have a muted contralateral effect. These findings confirm the variation in specific host inflammatory response types to localized plaque-induced inflammation and the subsequent effects within distant healthy tissues that impacts both the host mediator profiles and microbial community composition.

Results

Control Sites are not Static and Vary by Inflammatory Responder Type

Figure 10A:
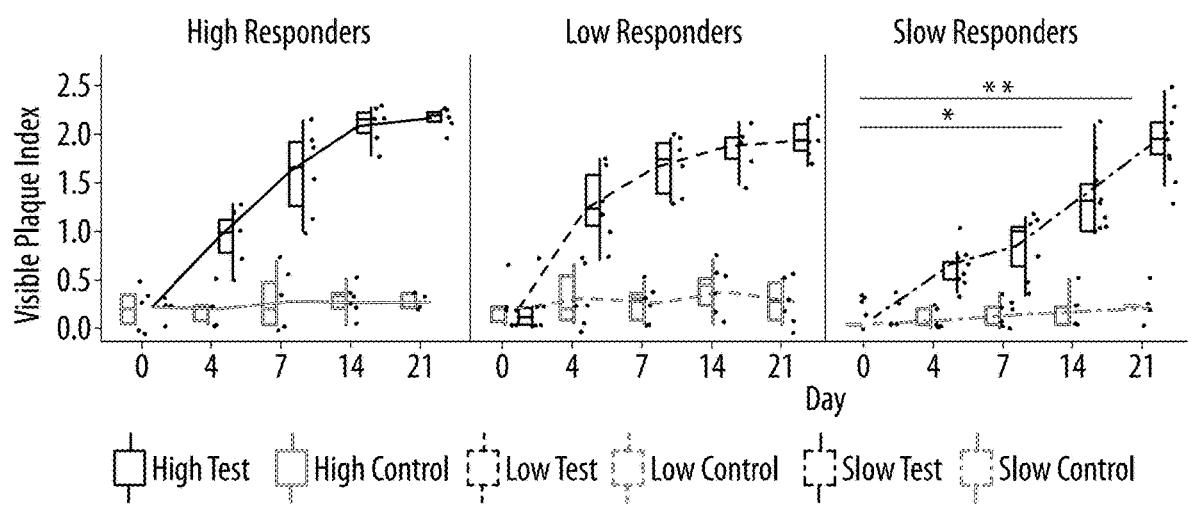
FIGS. 10A-10J contain data showing that control sites are not static and vary by Inflammatory Responder Type.
Figure 10B:
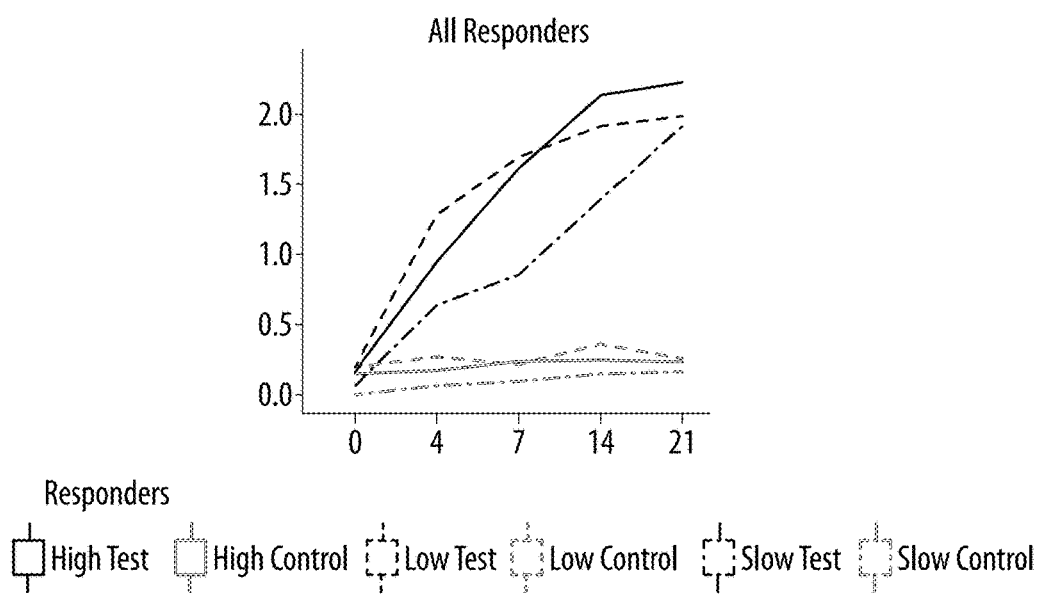
Figure 10C:
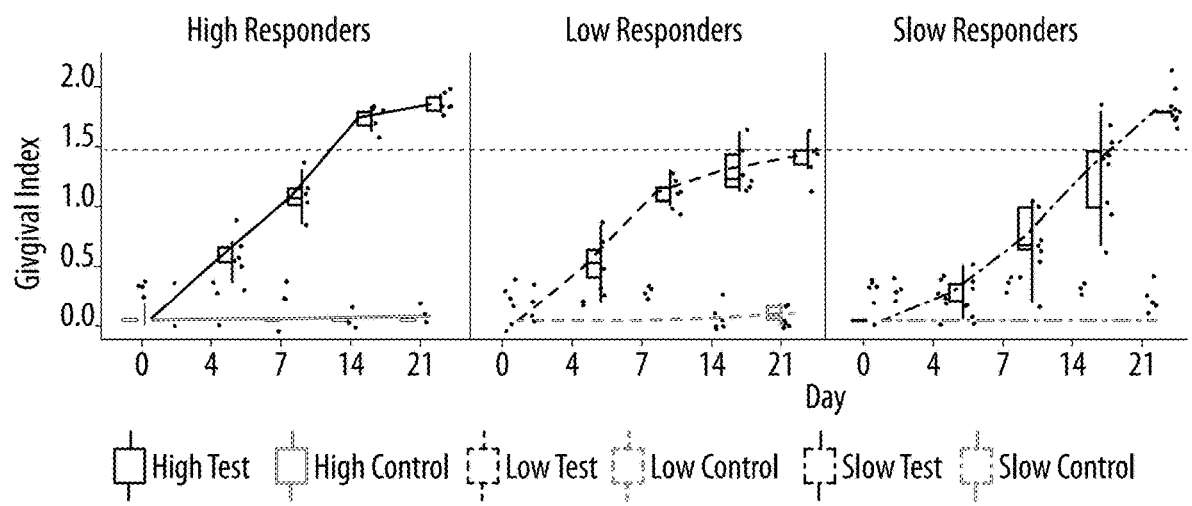
Figure 10D:
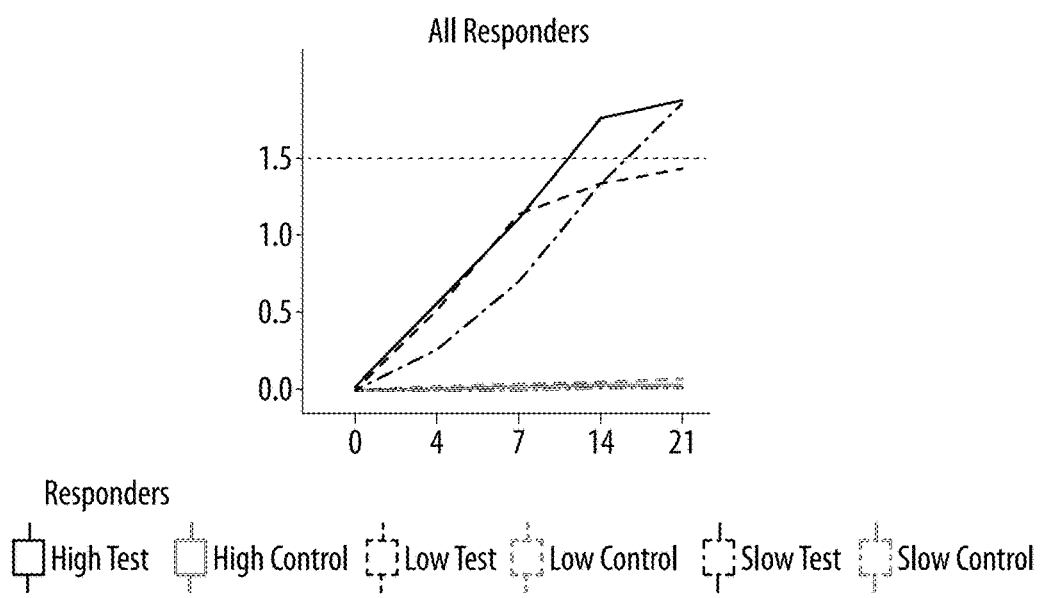
Figure 10E:
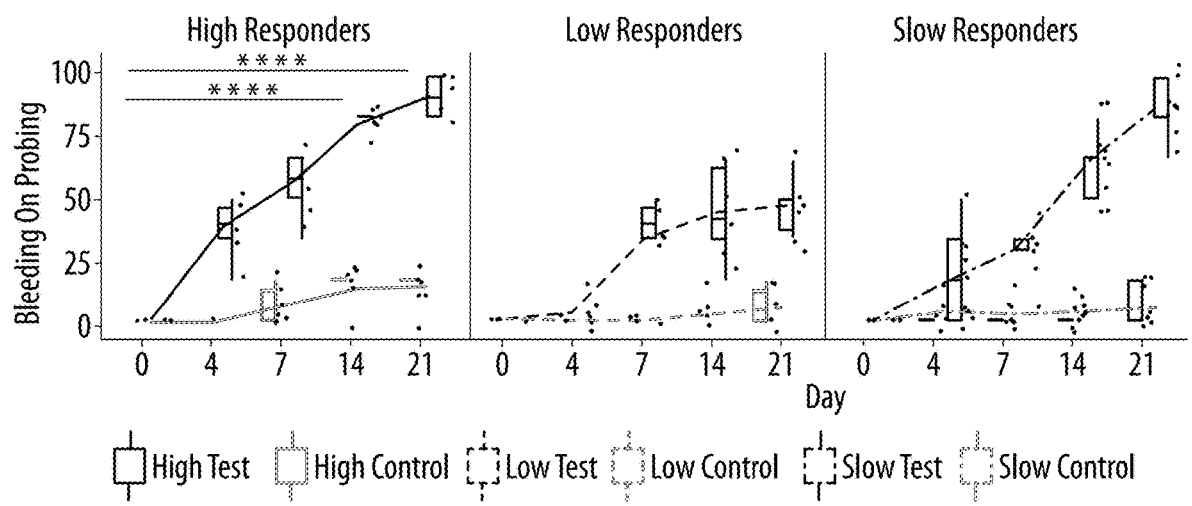
Figure 10F:
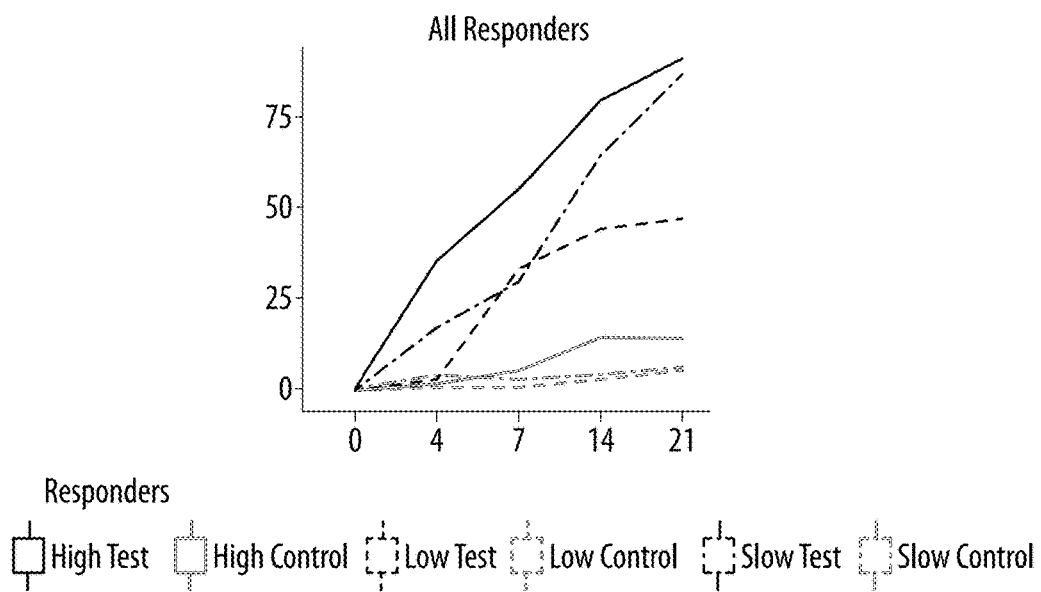
Figure 10G:
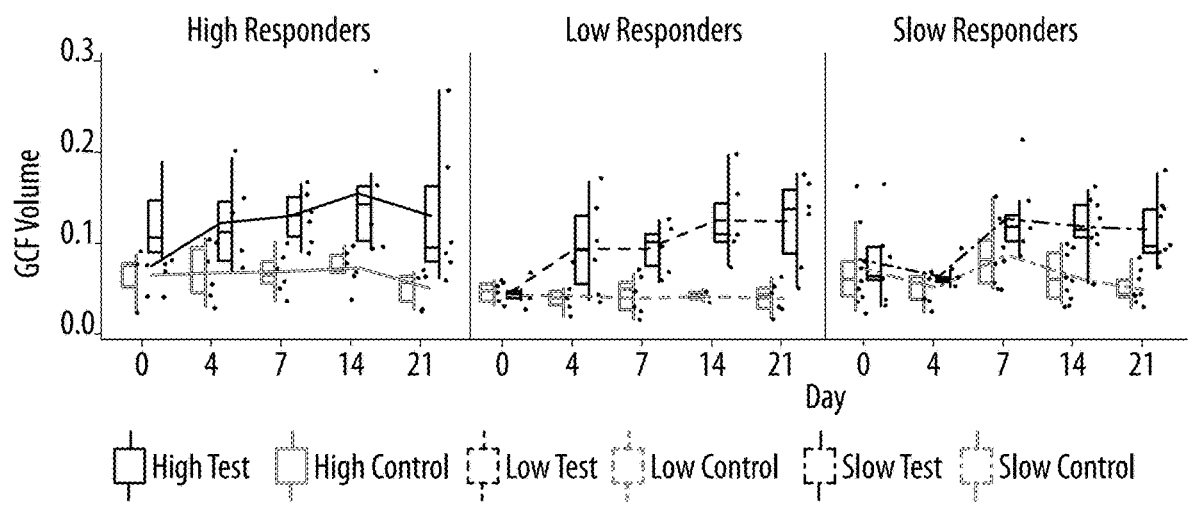
Figure 10H:
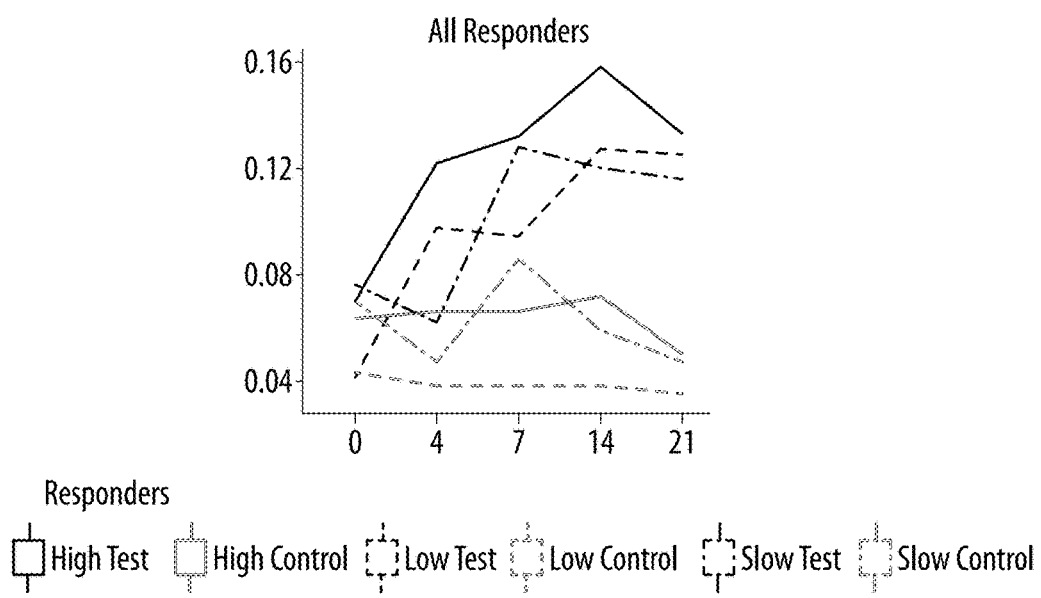
Figure 10I:
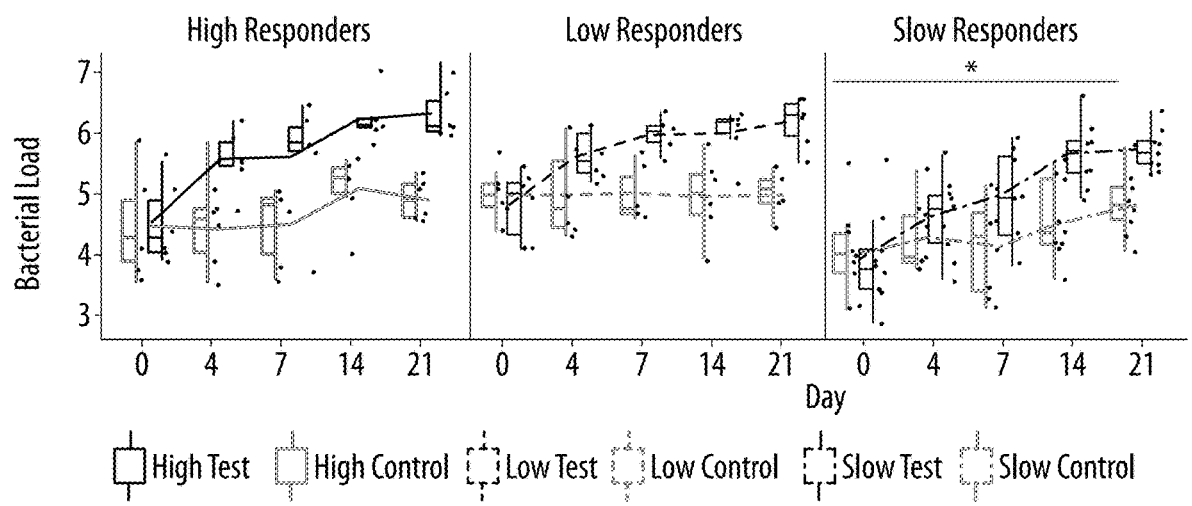
Figure 10J:
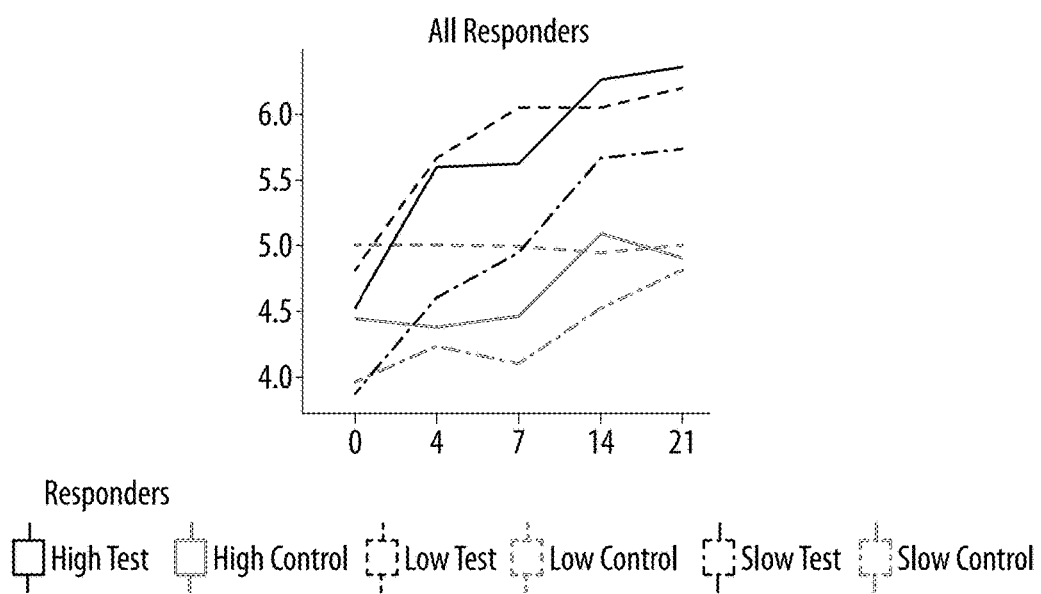

At the time of inclusion (Day −14) all study participants received a professional cleaning which aimed to normalize the oral health status across individuals. At baseline (Day 0), study subjects refrained from brushing on the test site of their mouth which was protected by a personalized plastic stint, while the control site maintained regular oral hygiene with fluoride containing toothpaste for a period of 21 Days. Plaque index (PI) (FIGS. 10A and 10B) remained rather stable among control sites over the induction period (Day 0-21). No clinical inflammation, represented by gingival index (GI) and bleeding on probing (BOP) (FIGS. 10C-10F), was observed on the control sites among these generally healthy individuals over the induction period. However, changes were observed on the control site in both gingival crevicular fluid (GCF) volume (FIGS. 10G and 10H) and bacterial load (FIGS. 10I and 10J)—although at a lower magnitude compared to test sites. Interestingly, bacterial load, which represents the number of 16S rRNA gene copies within a sample, increased among all Inflammatory Responder Types (IRTs) despite a stable PI.

Induced Inflammation in Test Sites Changes Chemokine Profiles in Control Sites

Figure 11A:
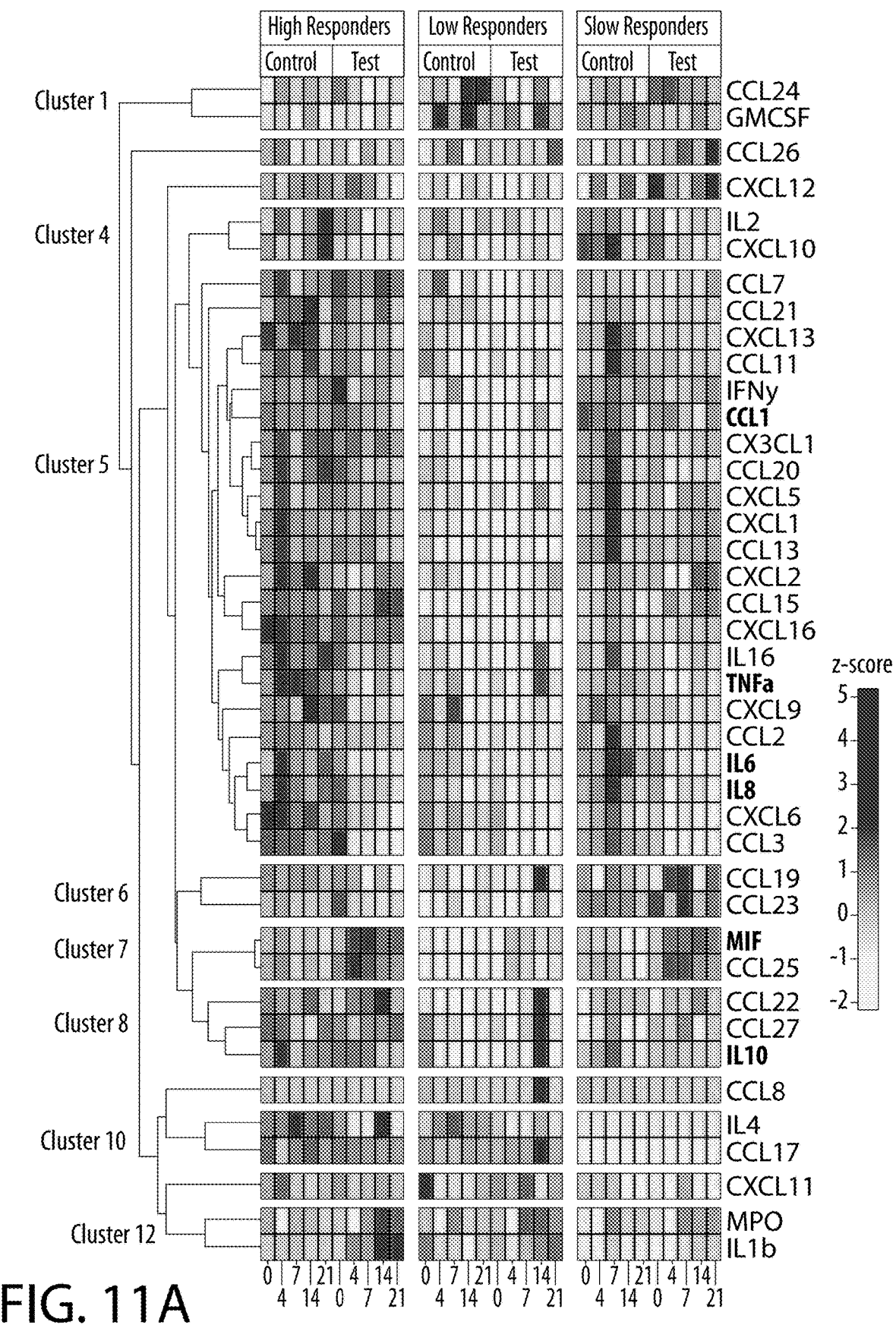
FIGS. 11A-11F show induced inflammation in Test sites changes chemokine profiles in Control sites.
Figure 11B:
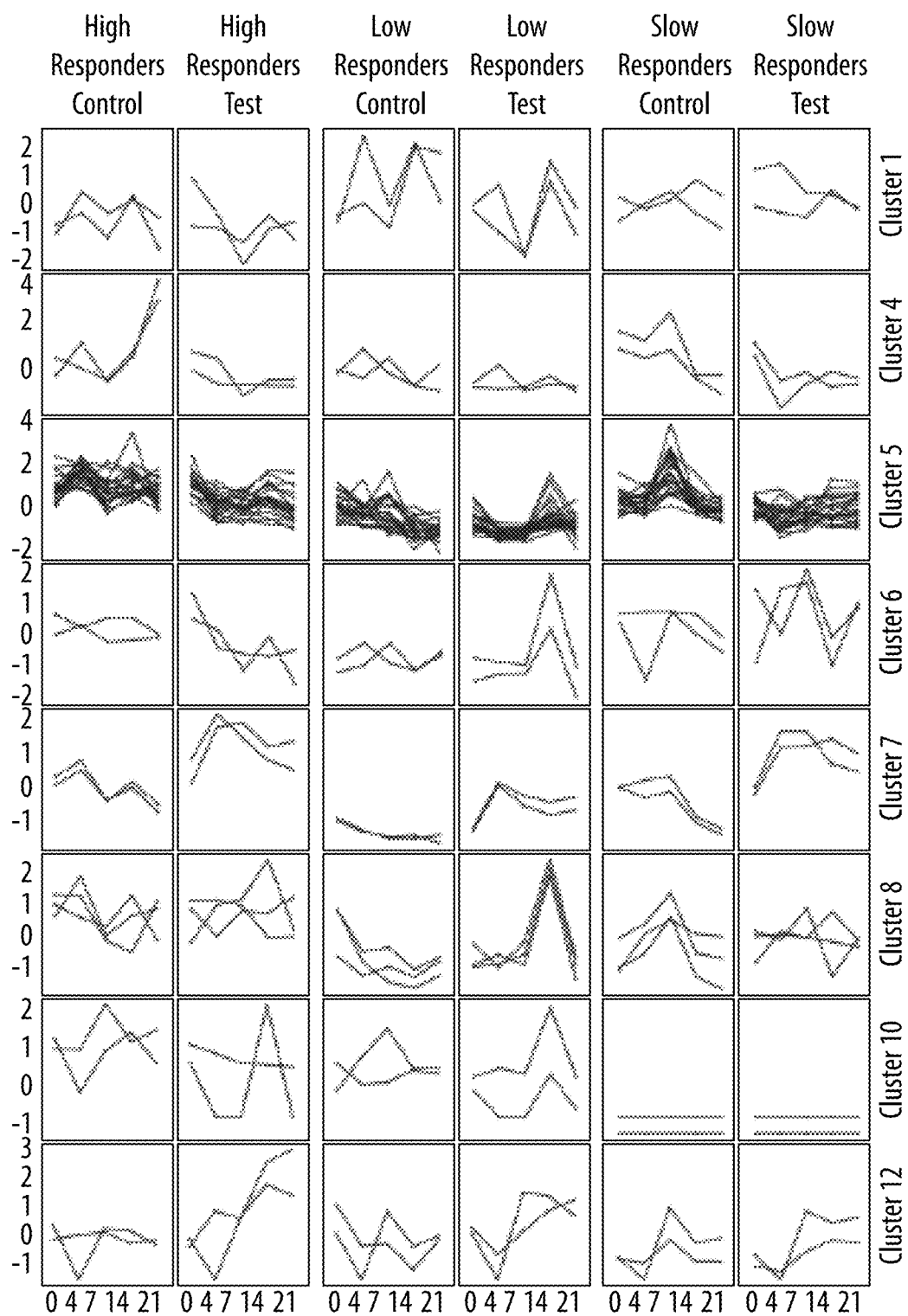

A panel of 41 host mediators within gingival crevicular fluid (GCF) were examined among Inflammatory Responder Types (IRTs) test and control sites over the Induction phase (Day 0-21). A row-wise z-scored heatmap of chemokines by IRT test and control sites (FIG. 11A) was clustered using the k-means algorithm and resulted in 12 unique clusters. Individual clusters, which represent the trajectories of the standard deviation from the mean value, were then stratified by IRT test and control sites in order to investigate the temporal dynamics of similarly behaving chemokines over the Induction phase (FIG. 11B). Again, the control sites were neither static nor randomly changing as there were multiple mediators showing similar patterns that varied by responder type and time compared to the test sites.

Figure 11C:
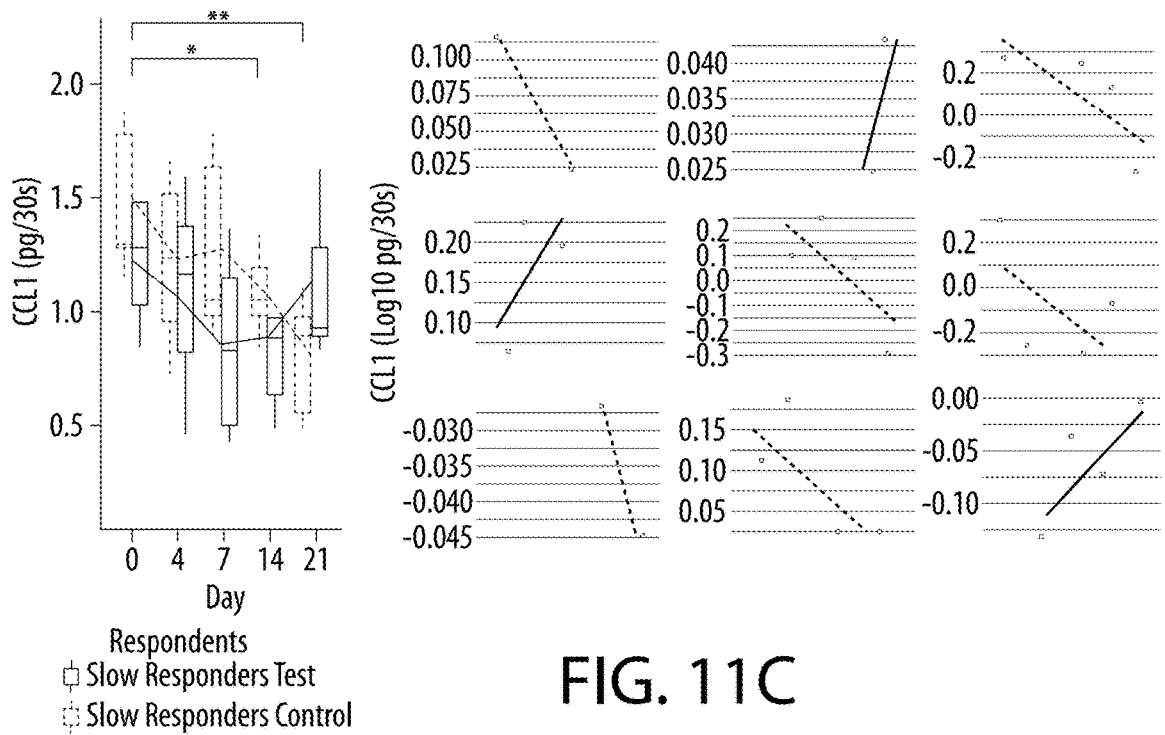
Figure 11D:
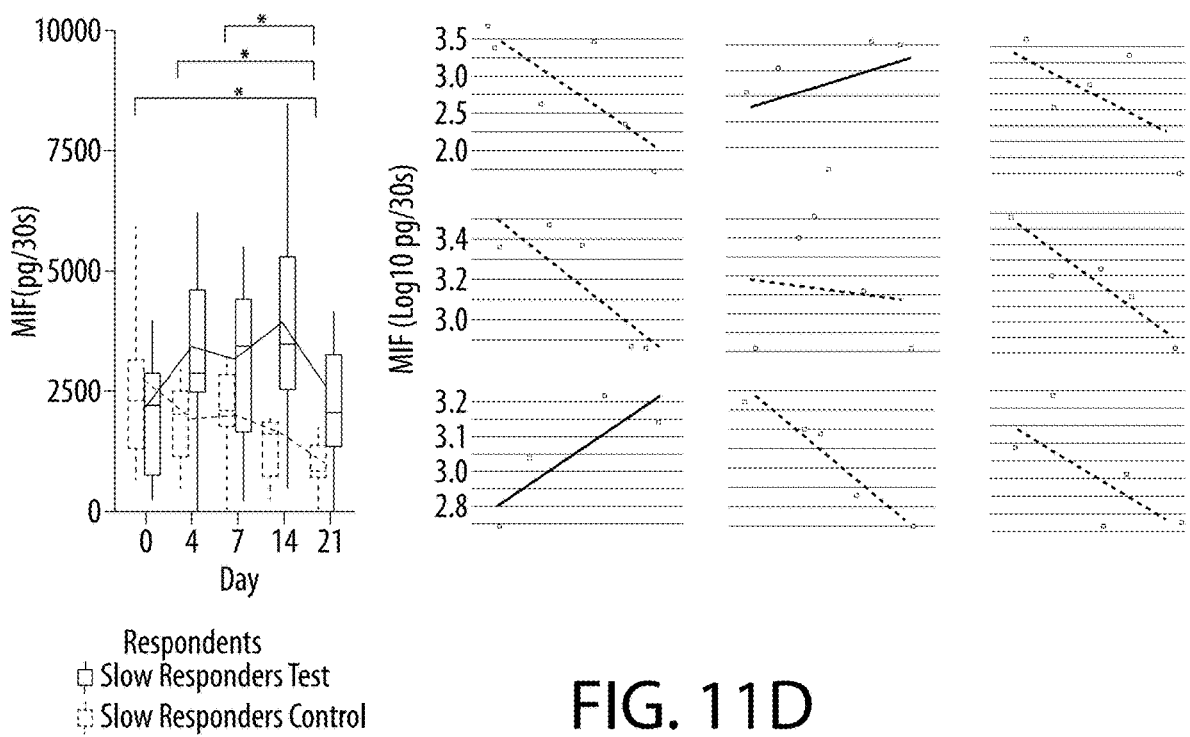
Figure 11E:
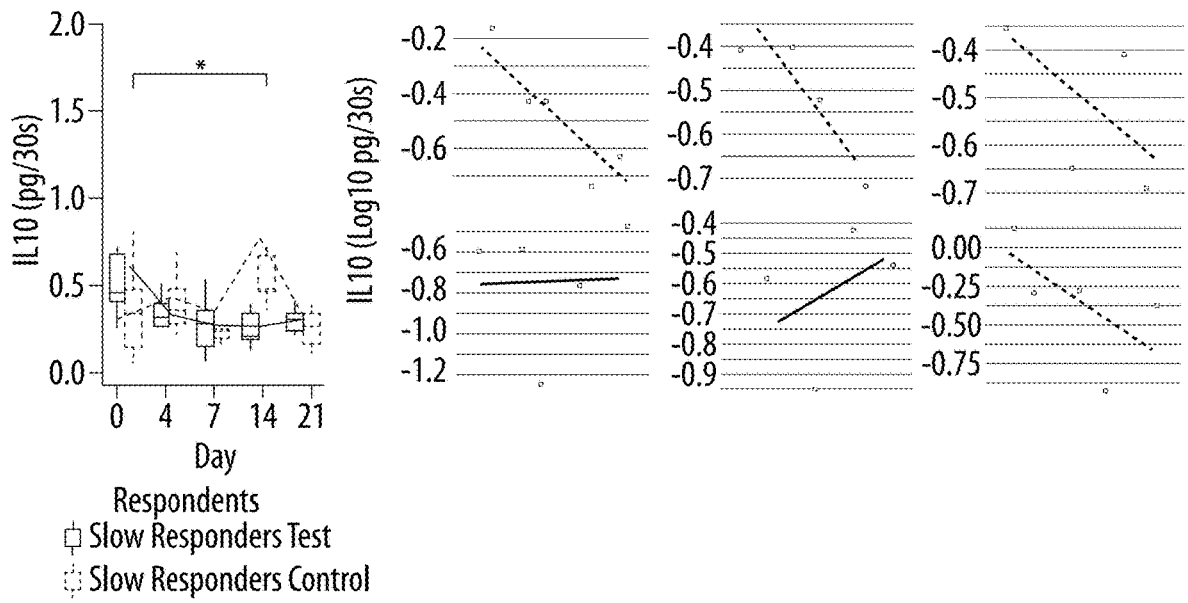
Figure 11F:
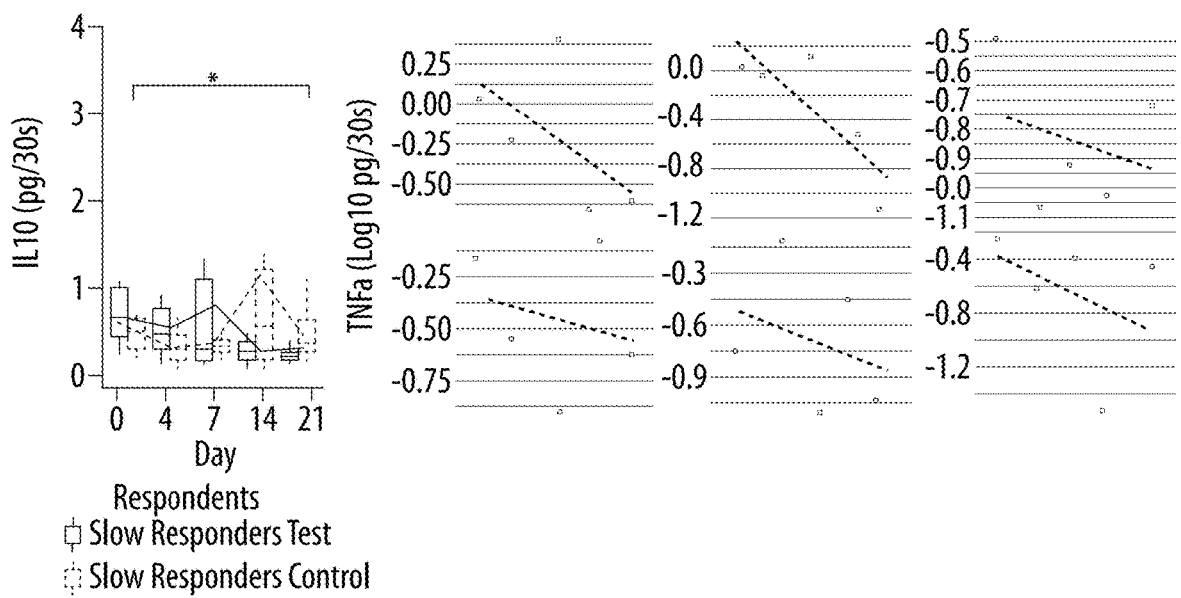

Of particular interest was cluster 5 which contains several pro-inflammatory mediators (tumor-necrosis factor alpha; TNFα, interleukin 6 and 8; IL-6, IL8) and seemed to share similar trajectories over the induction phase among the different IRTs—peaking by Day 4 in the High- and Low-IRT controls yet delayed until Day 7 in the Slow-IRT control sites (FIGS. 11A and 11B). Furthermore, even though Low- and Slow-IRTs showed no signs of clinical inflammation on the control sites during the first 7 days (FIGS. 10C and 10E), Slow-IRT still showed significant changes in macrophage migration inhibitory factor (MIF) (FIG. 11C) and C-C motif ligand 1 (CCL1) (FIG. 11D) while the Low-IRT showed significant changes in mediators interleukin 10 (IL-1β) (FIG. 11E) and TNF-a (FIG. 11F) across that same time frame.

Figure 12A:
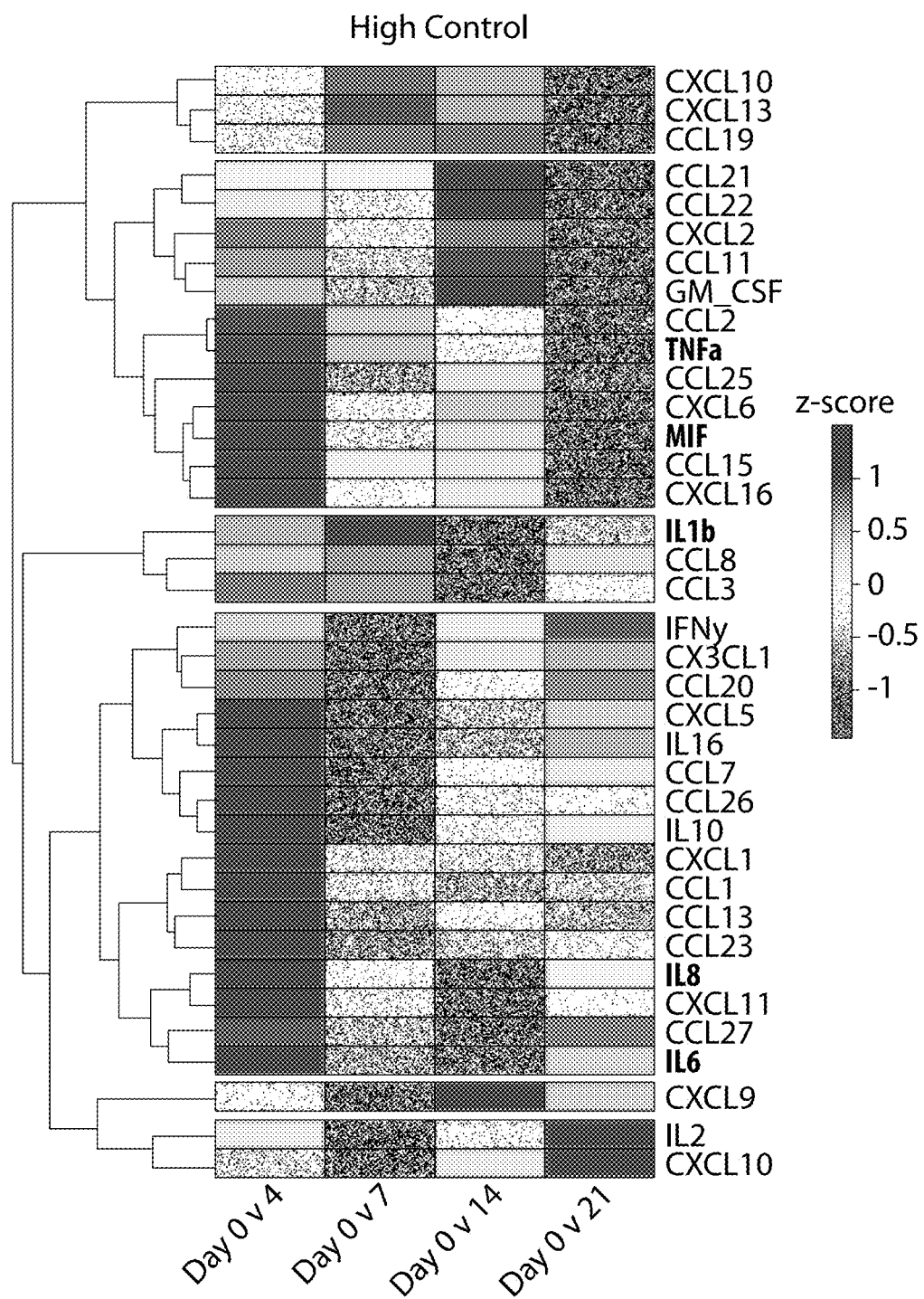
FIGS. 12A-12F show maturing plaque in Test Sites induces Host Mediator changes in Control Sites which precede a shift in the Control Site Microbiome.
Figure 12B:
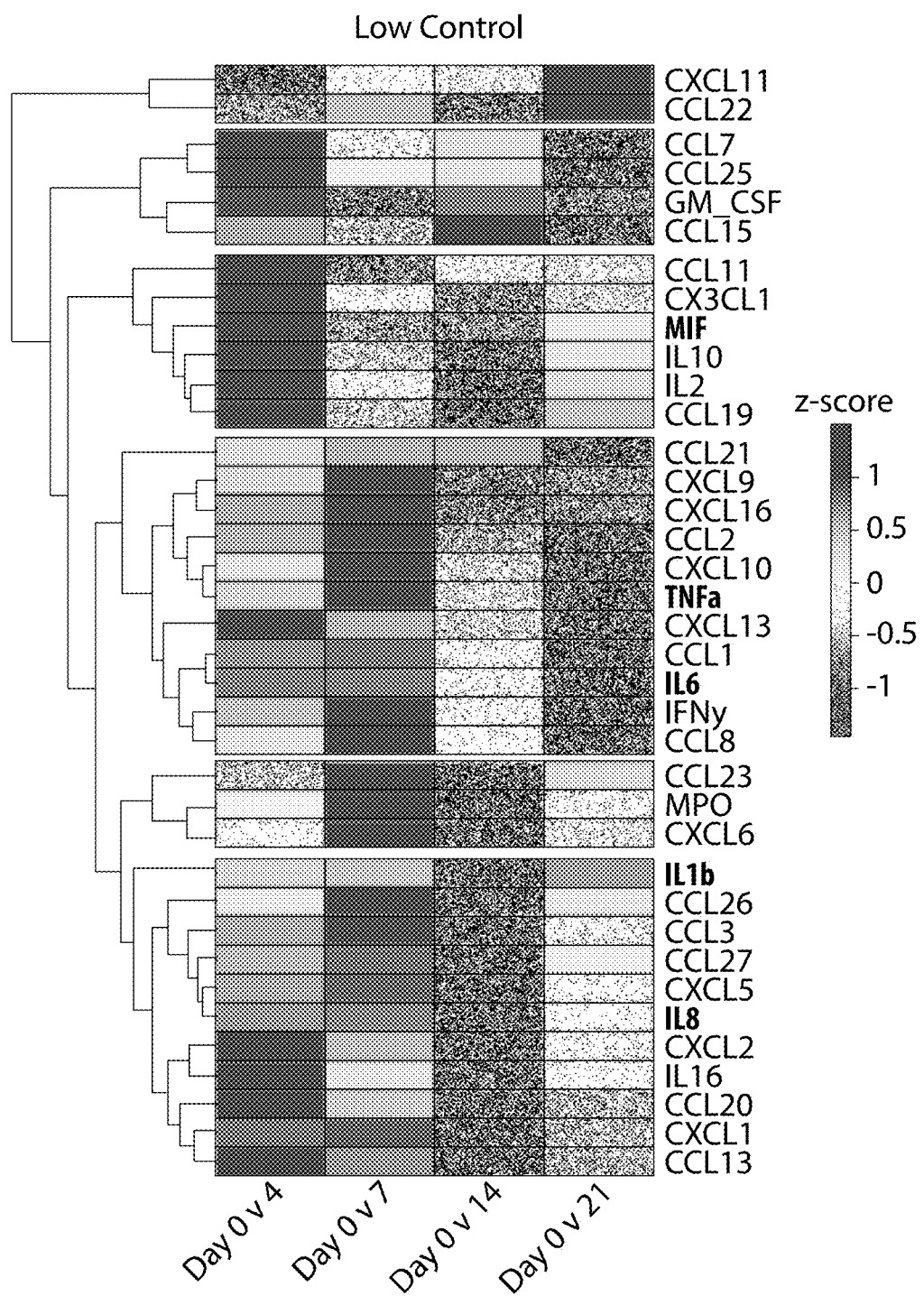
Figure 12C:
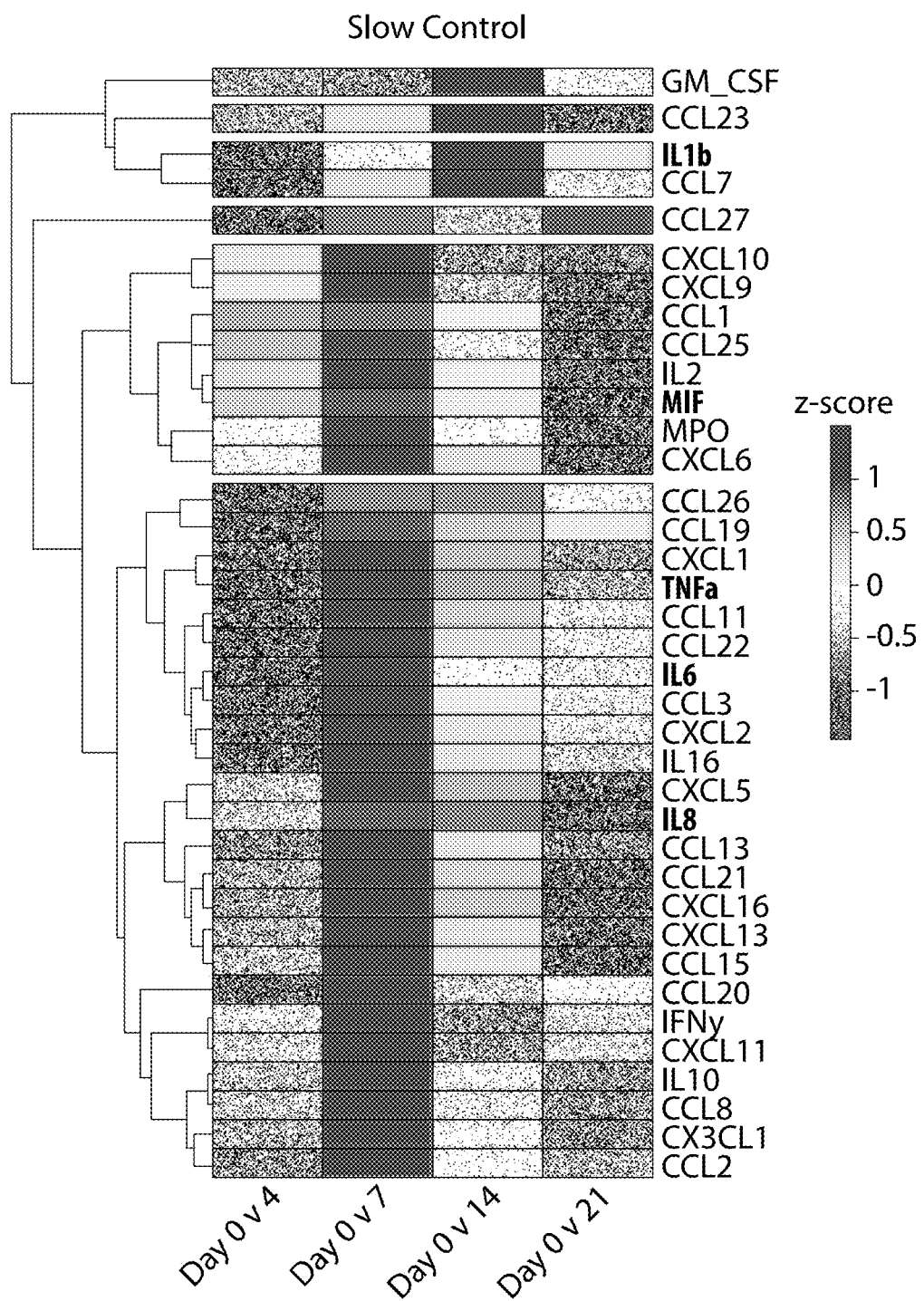

Maturing Plaque in Test Sites Induces Host Mediator Changes in Control Sites which Precede a Shift in the Control Site Microbiome Having established that both the microbiome and host mediators change within control sites across Inflammatory Responder Types (IRTs), we sought to investigate if a temporal relationship between these changes could be resolved between test and control sites among the different IRTs. In order to capture when the largest shift in host mediators occurred within respective IRT control sites, we converted our host mediator data over the Induction phase (Day 0-21) into a Log Fold-Change (Log FC) value compared to Baseline (Day 0). We then plotted a z-scored heatmap of this Log FC (FIGS. 12A-12C). This revealed a distinct shift within the High-IRT by Day 4 and Slow-IRT by Day 7. Including key pro-inflammatory markers TNF-a, IL-6, and IL-8 (FIGS. 12A-12F). Together, this data indicates a systemic effect in the oral cavity with a subclinical effect on the hosts mediators within healthy sites that likely results from locally induced inflammation occurring elsewhere in the mouth. As with host response in the test sites, this contralateral effect appeared to vary by the different Inflammatory Responder Types identified by experimental gingivitis.

Discussion

Microbially-induced inflammation was produced in test sites for a period of 21 Days in a well-controlled and reversible way within young generally healthy adults. Through a combination of high-resolution multi-omic analysis of host mediators from gingival crevicular fluid (GCF) significant changes in both host mediators were identified. Importantly, these changes were followed by similar trends observed within distant test sites located contralaterally in the mouth.

Figure 12D:
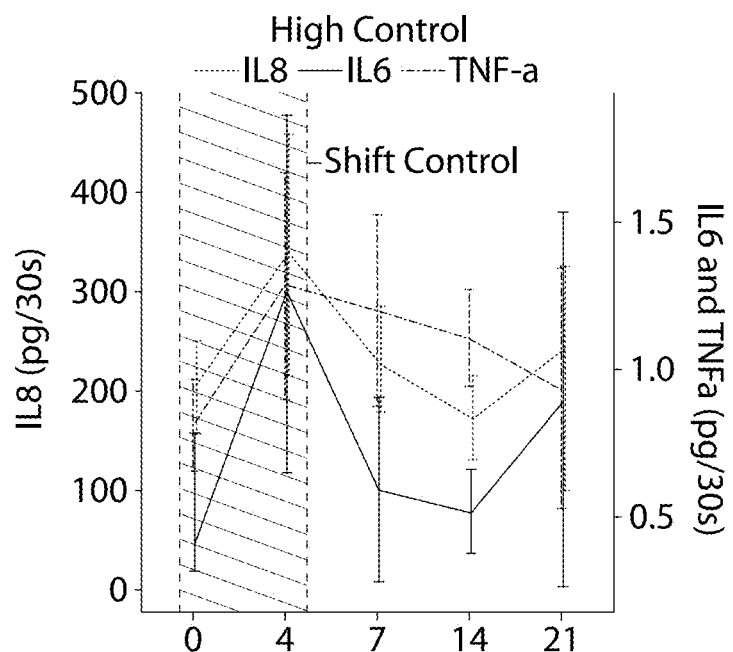
Figure 12E:
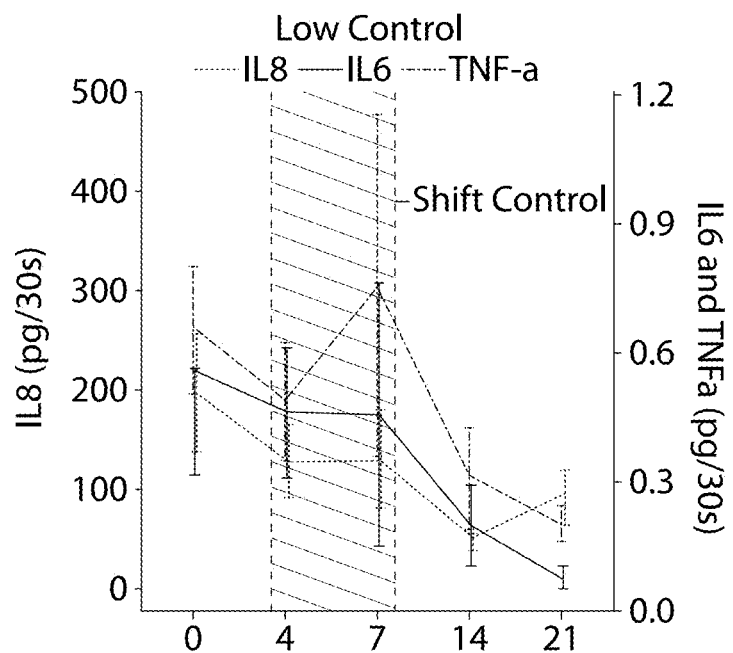
Figure 12F:
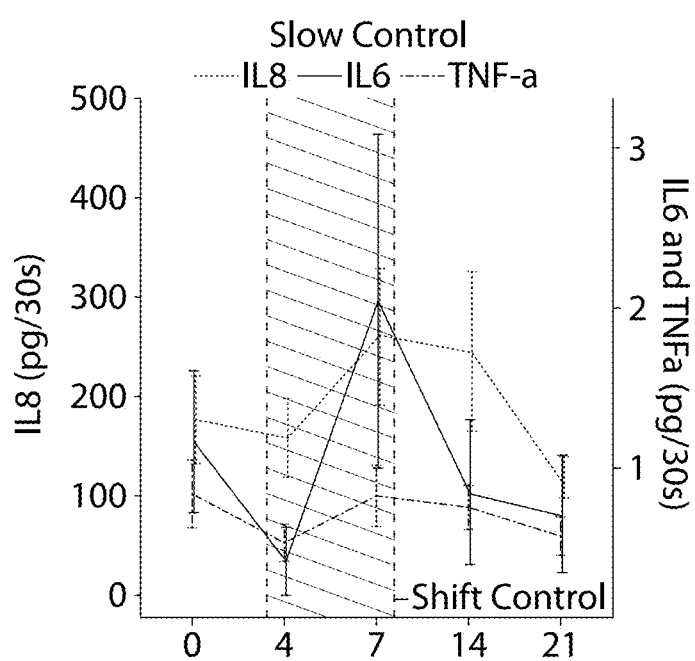

An examination of 37 host mediators associated with varying states of gingival and bone homeostasis within test and control sites was made. The mediators fell into a number of clusters with similar temporal dynamics during the 21 Day period of induced inflammation (FIG. 12B). Of particular interest was Cluster 5 as it contained multiple proinflammatory host mediators that are well established to increase during various stages of gingival inflammation associated with gingivitis and periodontitis, including: interleukin-6 (IL-6), interleukin-8 (IL-8), interleukin-1 beta (IL1-b), and tumor necrosis factor alpha (TNF-a). Focusing on these established proinflammatory biomarkers emphasized the presence of host mediator responses in the control sites and that these shifts were IRT-dependent (FIGS. 12A-12F). This analysis highlights the greatest fold-change in these proinflammatory markers was between Day 0 (baseline) and Day 4 for the High-IRT (FIG. 12A). Slow-IRT showed a similar pattern, although delayed until Day 7 (FIG. 12D). Notably, for both the High- and Low-IRT, the timing of these mediator changes corresponded with the timing of significant amount of plaque accumulation in the distant test sites, represented by plaque index (PI), and onset of clinically observed inflammation, represented by gingival index (GI) and bleeding on probing (BOP) (FIGS. 10A-10F and FIG. 12D). Interestingly, the Low-IRT seemed to have a lower propensity to affect distant, otherwise generally healthy, sites in comparison to the High- and Slow-IRT. Although unexpected, this observation was not uncharacteristic as the Low-IRT are able to modulate their immune response within test sites (FIGS. 10C-10F) and have the lowest levels of many host mediators measured in this study (FIG. 11A). The reduced effects within distant control sites located contralaterally in the mouth may be due to the lower levels of inflammation and host mediators during experimental gingivitis.

The temporal analysis of host mediator demonstrates that normal plaque accumulation and maturation occurring within test sites results in a major shift in host mediators. Unexpectedly these changes were simultaneously detected in distant healthy control sites, although in lower magnitude. The changes occurred in the absence of significant clinical inflammation or plaque accumulation due to maintained hygiene of control sites for the duration of the study. This suggests that these subclinical changes in host mediators, when coupled with a maturing biofilm elsewhere in the mouth, may facilitate a subgingival environment more favorable for Bacteroidetes members and may provide a mechanism in which localized periodontal inflammation can cause distant healthy tooth sites to become susceptible. Furthermore, this relationship varies by clinical Inflammatory Responder Type (IRT) and indicates that different IRTs may have different levels of risk associated with periodontal disease and/or disease progression.

The invention claimed is:

1. A method of identifying an individual who has been identified as having gingivitis as being a slow gingivitis responder or a high gingivitis responder and treating said individual comprising the steps of:
   a) obtaining a gingivitis-derived sample of gingival crevicular fluid from the individual;
   b) quantifying a cytokine consisting of IL-1β present in the gingivitis-derived sample to establish a gingivitis patient IL-1β level; and
   c) comparing the gingivitis patient IL-1β level with a pre-gingivitis IL-1β level that was established by obtaining a non-gingivitis-derived sample of gingival crevicular fluid from the individual prior to the development of gingivitis and quantifying IL-1β present in the non-gingivitis-derived sample to establish a pre-gingivitis IL-1β level, wherein if the gingivitis patient IL-1β level is significantly unchanged compared to the pre-gingivitis IL-1β level, the individual is a slow gingivitis responder and if the gingivitis patient IL-1β level is significantly elevated compared to the pre-gingivitis IL-1β level, the individual is a high gingivitis responder; and/or
   d) obtaining a distant healthy-derived sample of gingival crevicular fluid from the individual;
   e) quantifying one or both cytokines select from the group consisting of MIF and CCL-1 present in the distant healthy-derived sample to establish a distant healthy MIF level and/or a distant healthy CCL-1 level; and
   f) comparing the distant healthy MIF level and/or a distant healthy CCL-1 level with a pre-gingivitis MIF level or pre-gingivitis CCL-1 level, respectively, that was established by obtaining the non-gingivitis-derived sample of gingival crevicular fluid from the individual prior to the development of gingivitis and quantifying MIF and/or CCL-1 present in the non-gingivitis-derived sample to establish a pre-gingivitis MIF level or pre-gingivitis CCL-1 level, wherein if the distant healthy MIF level and/or a distant healthy CCL-1 level is significantly elevated compared to the pre-gingivitis MIF level or pre-gingivitis CCL-1 level, the individual is a slow gingivitis responder and if the distant healthy MIF level and/or a distant healthy CCL-1 level is not significantly elevated compared to the pre-gingivitis MIF level or pre-gingivitis CCL-1 level, the individual is a high gingivitis responder, the method further comprising applying to the oral cavity of the individual one or more oral care compositions comprising one or more ingredients having antimicrobial activity and free of additional ingredients that have anti-inflammatory activity if the individual is identified as a slow gingivitis responder, or applying to the oral cavity of the individual one or more oral care compositions comprising one or more ingredients having antimicrobial activity and one or more ingredients having anti-inflammatory activity if the individual is identified as a high gingivitis responder.

2. The method of claim 1 wherein the individual is identified as being a slow gingivitis responder or a high gingivitis responder by:

conducting steps a) to c) and wherein the non-gingivitis-derived sample is a gingival crevicular fluid not derived from gingivitis.

3. A method of identifying an individual as being a slow gingivitis responder or a high gingivitis responder and treating said individual comprising the steps of:

a) obtaining a non-gingivitis-derived sample of gingival crevicular fluid from the individual prior to the individual being identified as having gingivitis;

b) quantifying a cytokine consisting of IL-1β present in the non-gingivitis-derived sample to establish a pre-gingivitis IL-1β level;

c) obtaining a gingivitis-derived sample of gingival crevicular fluid from the individual after the individual has been identified as having gingivitis;

d) quantifying IL-1β present in the gingivitis-derived sample to establish a gingivitis patient IL-1β level; and e) comparing the gingivitis patient IL-1β level with the pre-gingivitis IL-1β level, wherein if the gingivitis patient IL-1β level is significantly unchanged compared to the pre-gingivitis IL-1β level, the individual is a slow gingivitis responder and if the gingivitis patient IL-1β level is significantly elevated compared to the pre-gingivitis IL-1β level, the individual is a high gingivitis responder, and/or f) obtaining a non-gingivitis-derived sample of gingival crevicular fluid from the individual prior to the individual being identified as having gingivitis;

g) quantifying one or both cytokines select from the group consisting of MIF and CCL-1 present in the non-gingivitis-derived sample to establish a pre-gingivitis MIF level and/or pre-gingivitis CCL-1 level;

h) obtaining a distant healthy-derived sample of gingival crevicular fluid from the individual after the individual has been identified as having gingivitis;

i) quantifying one or both cytokines selected from the group consisting of MIF and CCL-1 present in the distant healthy-derived sample to establish a distant healthy MIF level and/or a distant healthy CCL-1 level; and j) comparing the distant healthy MIF level and/or a distant healthy CCL-1 with the pre-gingivitis MIF level or pre-gingivitis CCL-1 level, respectively, wherein if the distant healthy MIF level and/or a distant healthy CCL-1 level is significantly elevated compared to the pre-gingivitis MIF level or pre-gingivitis CCL-1 level, the individual is a slow gingivitis responder and if the distant healthy MIF level and/or a distant healthy CCL-1 level is not significantly elevated compared to the pre-gingivitis MIF level or pre-gingivitis CCL-1 level, the individual is a high gingivitis responder, the method further comprising applying to the oral cavity of the individual one or more oral care compositions comprising one or more ingredients having antimicrobial activity and free of additional ingredients that have anti-inflammatory activity if the individual is identified as a slow gingivitis responder, or applying to the oral cavity of the individual one or more oral care compositions comprising one or more ingredients having antimicrobial activity and one or more ingredients having anti-inflammatory activity if the individual is identified as a high gingivitis responder.

4. The method of claim 3 wherein the individual is identified as being a slow gingivitis responder or a high gingivitis responder by:

conducting steps a) to e).

5. The method of claim 3 or 4, further comprising the steps of examining the individual and determining that the individual does not have gingivitis prior to obtaining the non-gingivitis-derived sample of gingival crevicular fluid from the individual; and examining the individual and determining that the individual has gingivitis prior to obtaining the gingivitis-derived sample of gingival crevicular fluid from the individual; and prior to obtaining a distant healthy-derived sample of gingival crevicular fluid from the individual.

6. The method of claim 1 wherein the one or more ingredients having antimicrobial activity is selected from the group consisting of: arginine, zinc phosphate, zinc oxide, zinc citrate, triclosan, digluconate, thymol, menthol, eucalyptol, methyl salicylate, saline, antibiotics and fluoride.

7. The method of claim 6 wherein the one or more ingredients having anti-inflammatory activity is selected from the group consisting of: chlorhexidine, DHA and vitamin D.

8. The method of claim 6 wherein the one or more oral care compositions is selected from the group consisting of: a toothpaste, an oral rinse and a mouthwash.

* * * * *